United States Patent [19]

Smith et al.

[11] 4,417,590
[45] Nov. 29, 1983

[54] ELECTROENCEPHALOGRAPH

[75] Inventors: Leland B. Smith, Englewood, Colo.; Robert A. McIntyre, Skokie, Ill.

[73] Assignee: Beckman Instruments, Inc., Fullerton, Calif.

[21] Appl. No.: 204,396

[22] Filed: Nov. 6, 1980

Related U.S. Application Data

[63] Continuation of Ser. No. 914,272, Jun. 9, 1978, abandoned.

[51] Int. Cl.³ .............................................. A61N 5/04
[52] U.S. Cl. .............................................. 128/731
[58] Field of Search .............. 128/696, 709, 710, 731, 128/901, 902, 903, 908

[56] References Cited

U.S. PATENT DOCUMENTS

| | | | |
|---|---|---|---|
| 3,721,230 | 3/1973 | Ziernicki | 128/902 |
| 3,868,948 | 3/1975 | Graetz | 128/709 |
| 4,037,586 | 7/1977 | Grichniic | 128/731 |

*Primary Examiner*—William E. Kamm
*Attorney, Agent, or Firm*—R. J. Steinmeyer; P. R. Harder; E. C. Jason

[57] ABSTRACT

A multi-channel instrumentation system is provided wherein signals from selected electrode pairs are sequentially connected to the isolated input of a common signal amplifying path. The electrode pair selecting means is included in a portable head box which may be placed adjacent to the patient to be tested. Included in the head box are facilities for testing the impedance of any selected one of the patient electrodes and providing a visual indication of the magnitude of such impedance. The head box also includes facilities for selecting a group of patient electrodes which are connected together and used as an average or reference potential for one input of the common signal path. Facilities are also provided for calibrating the common signal path by applying a d.c. calibration signal to the input thereof by means isolated from system ground. An improved circuit arrangement is provided for limiting the current which can be drawn from the patient ground electrode to a small value to provide for the safety of the patient in the event of malfunctioning of the electrode selecting means. Facilities are provided in the common signal path for removing the d.c. components of the electrode pair signal voltages, and for selectively varying the gain of the common signal path on an individual channel basis.

30 Claims, 40 Drawing Figures

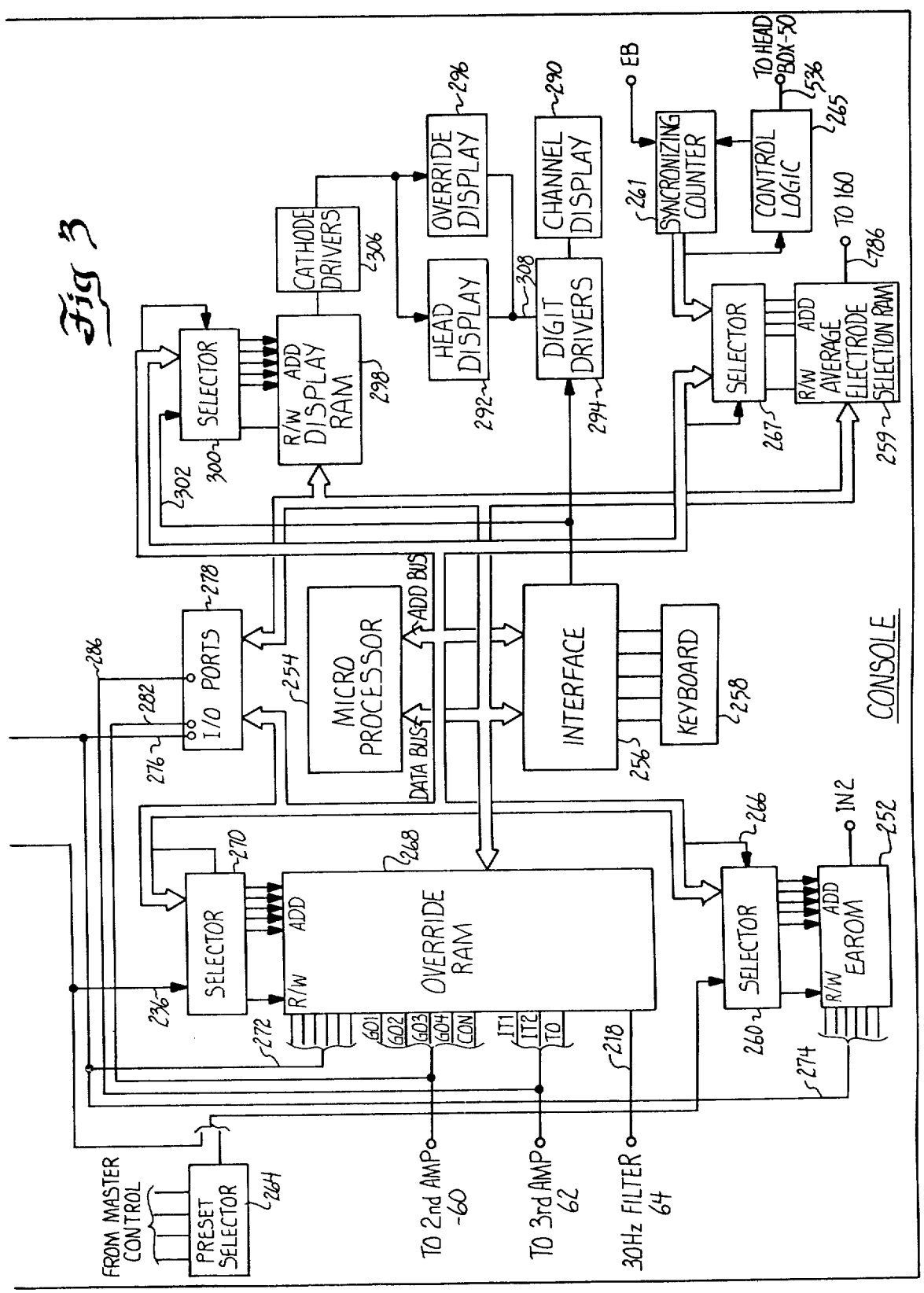

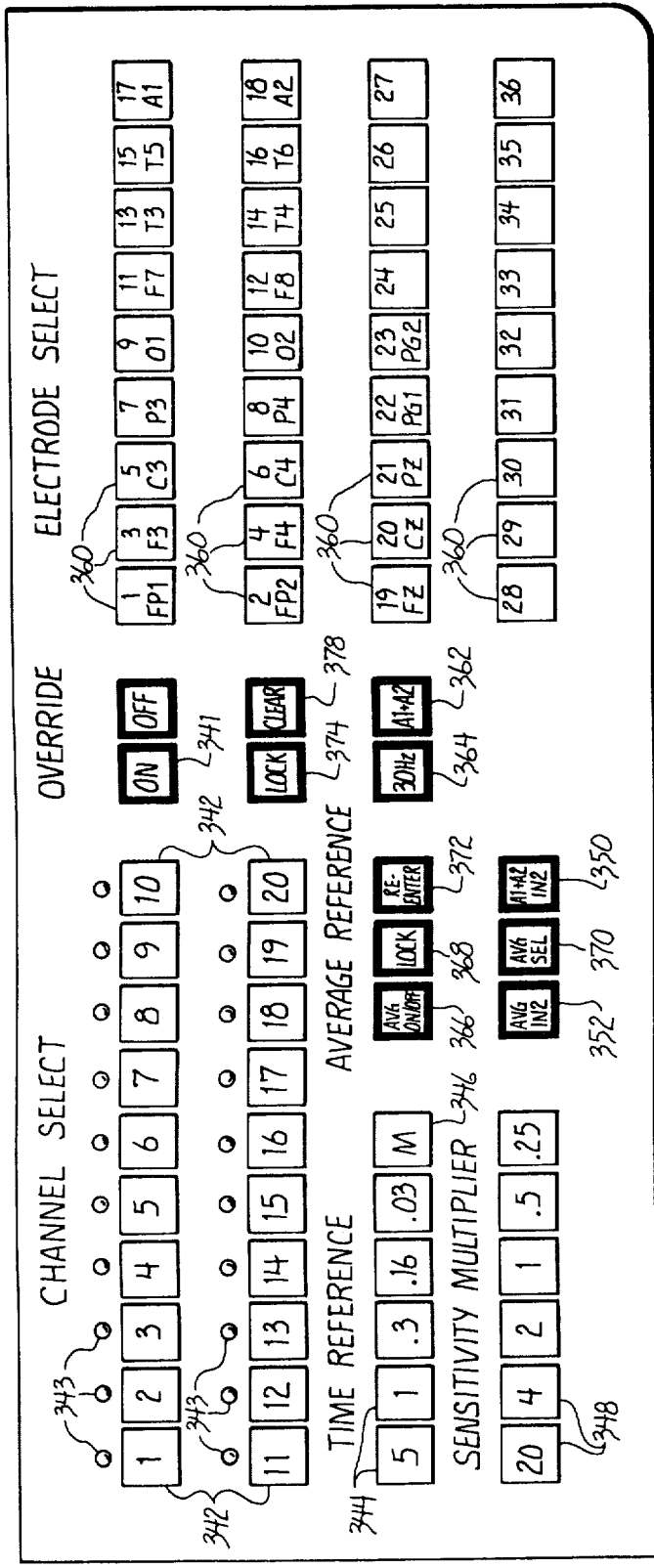

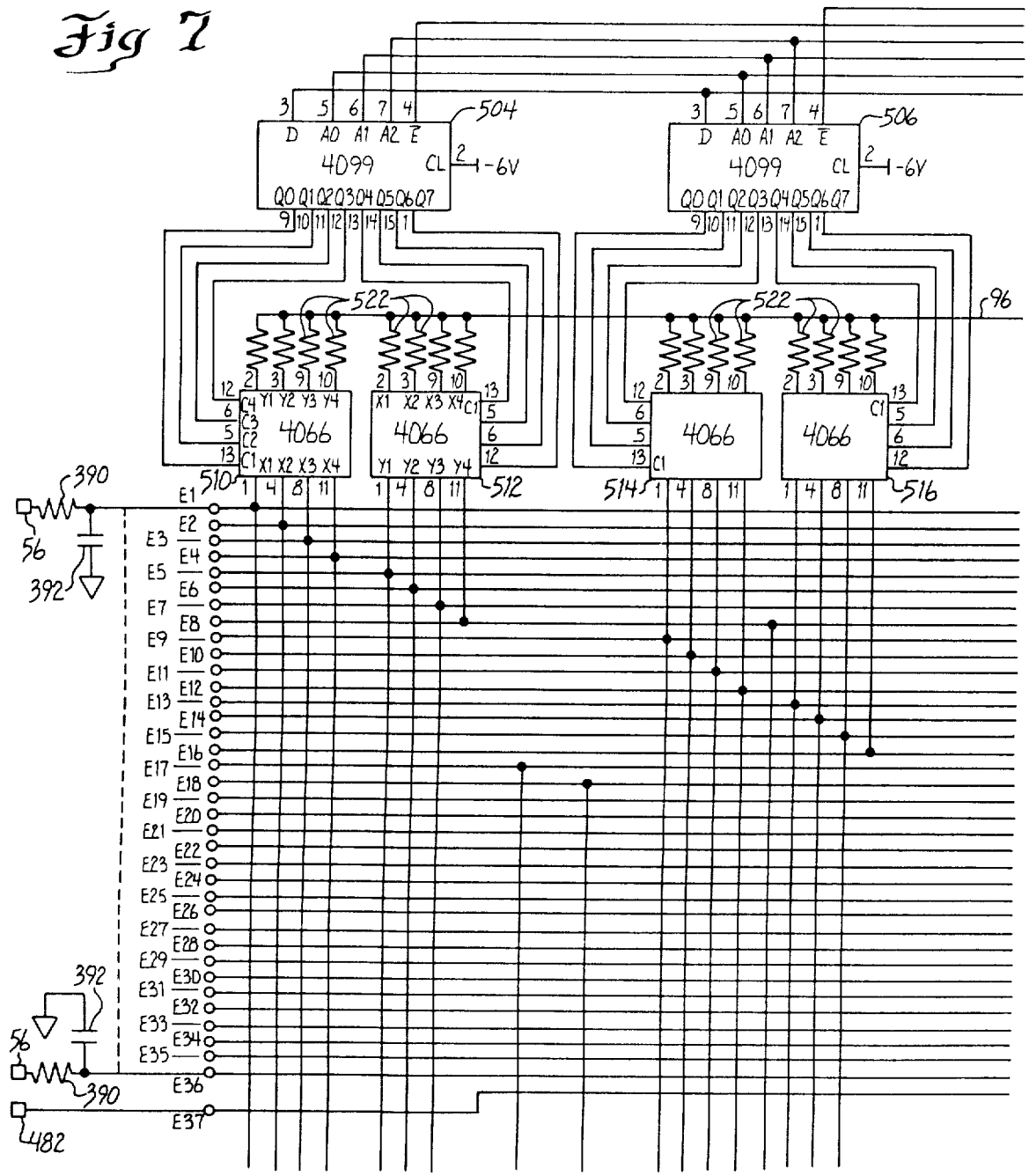

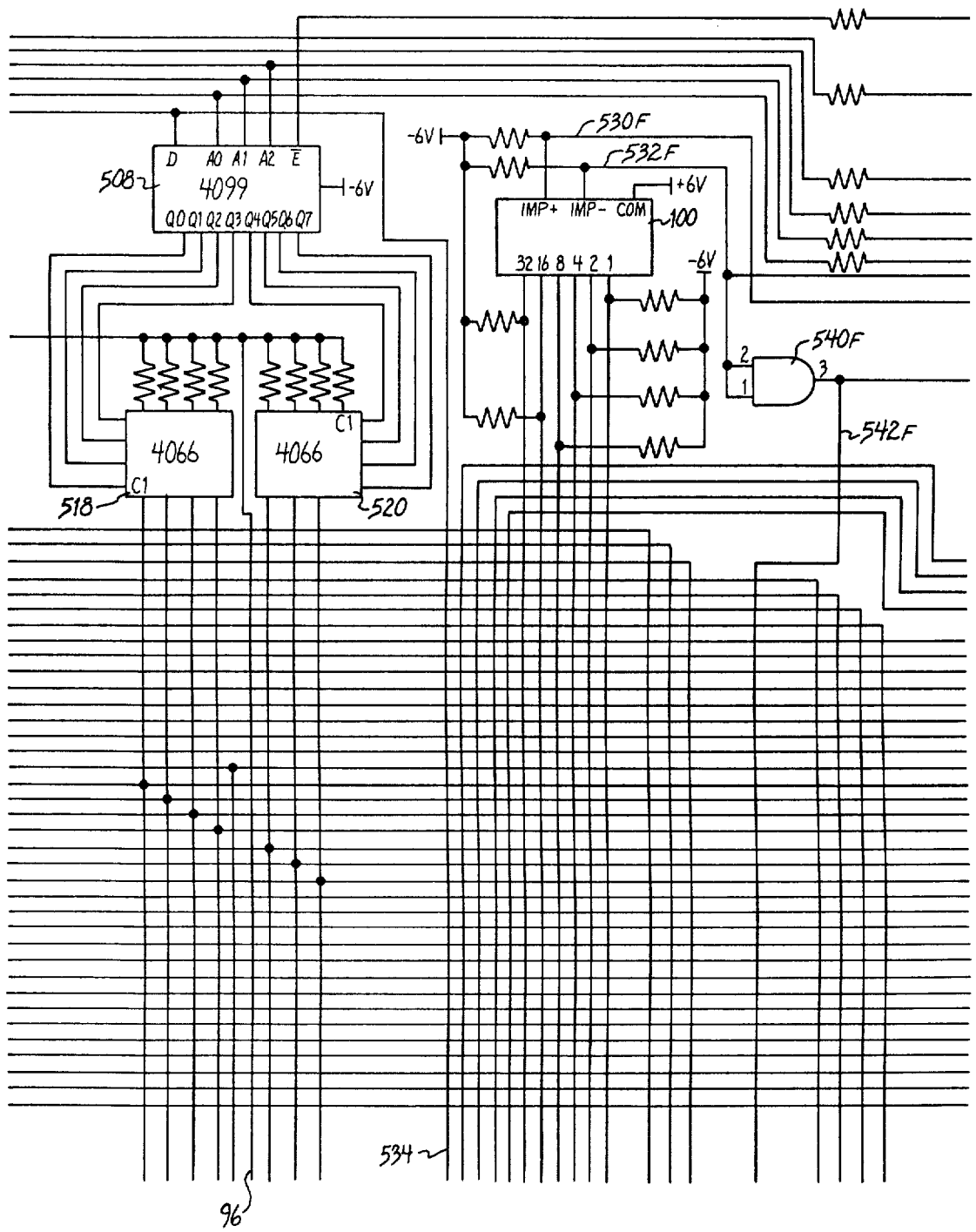

| Fig 7 | Fig 8 | Fig 9 | Fig 10 |
|---|---|---|---|
| Fig 11 | Fig 12 | Fig 13 | Fig 14 |

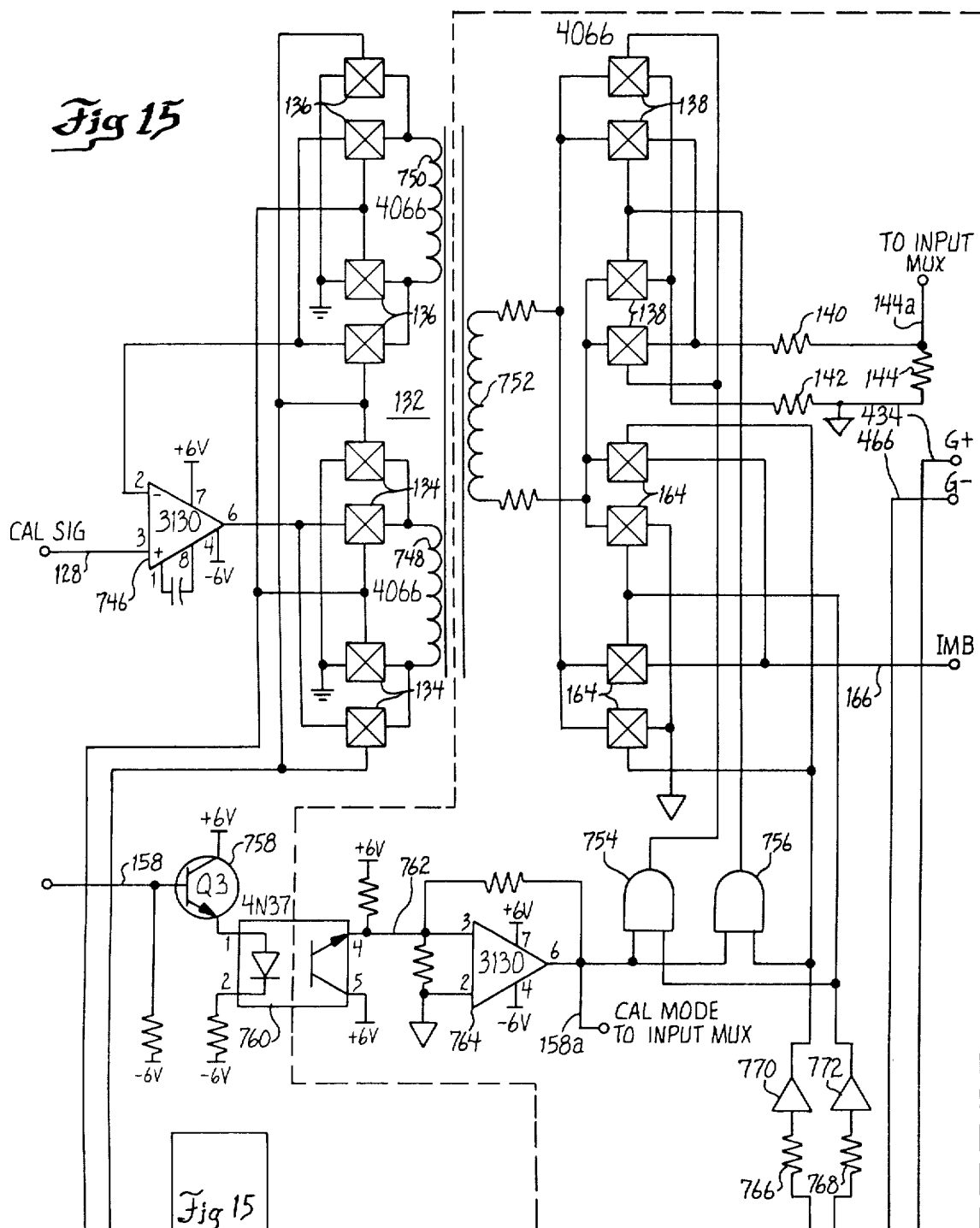

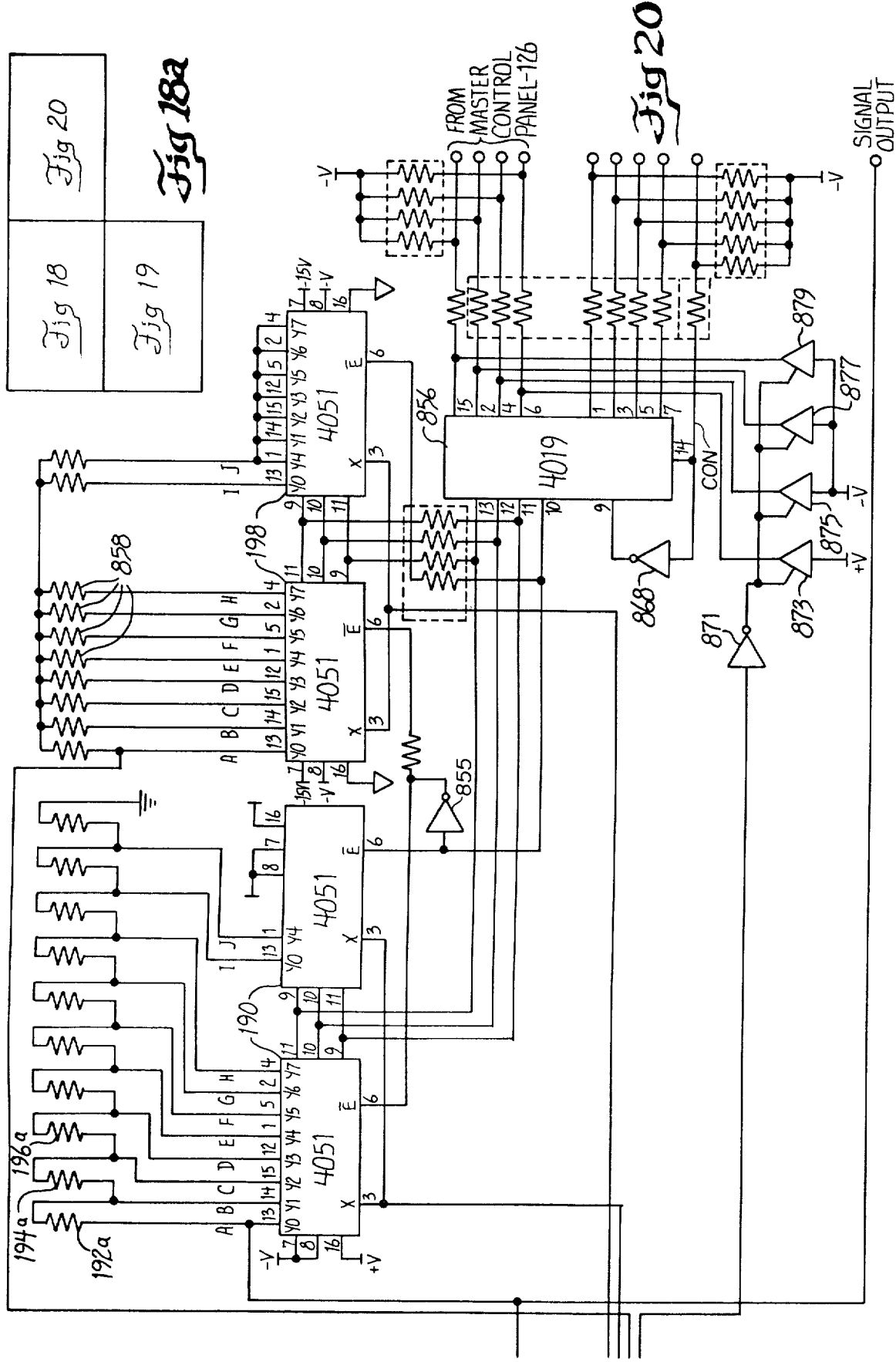

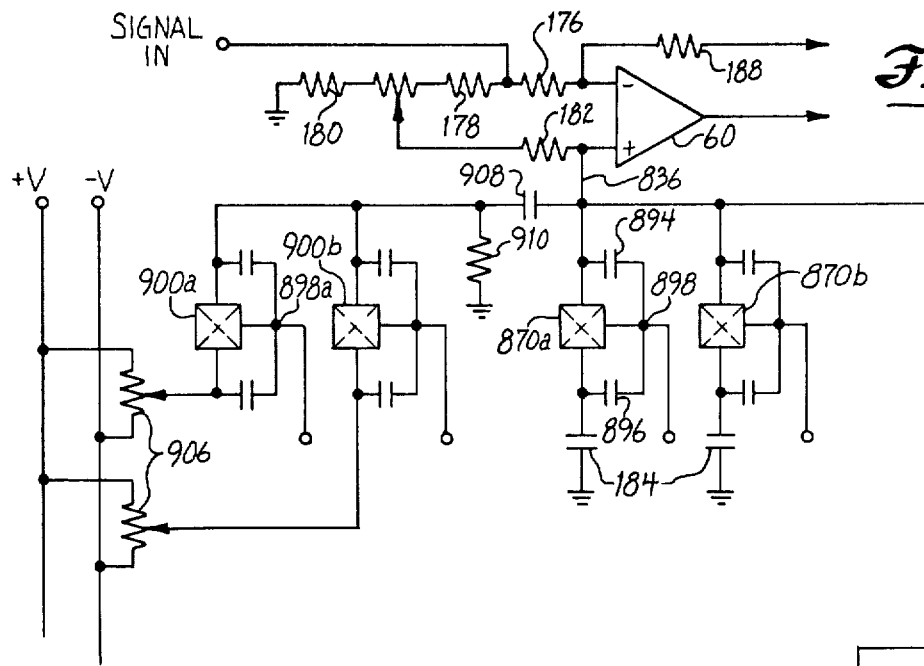
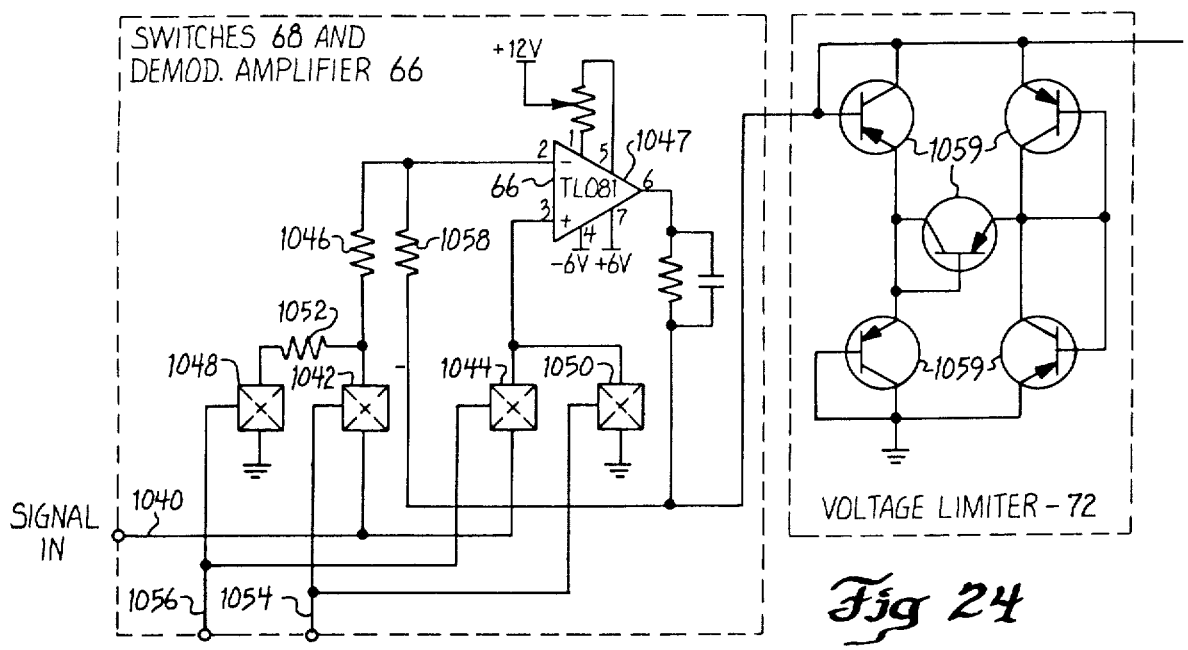

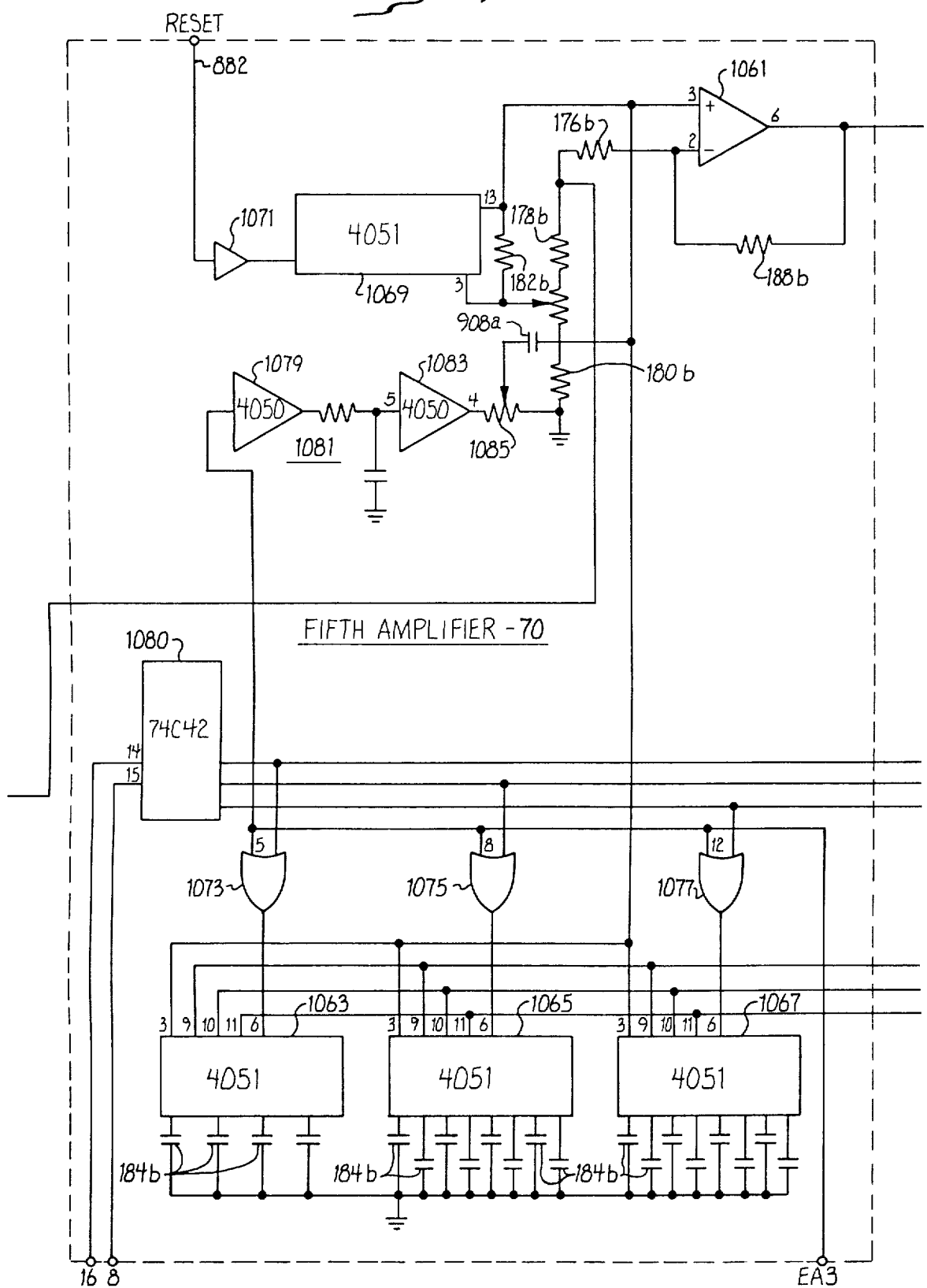

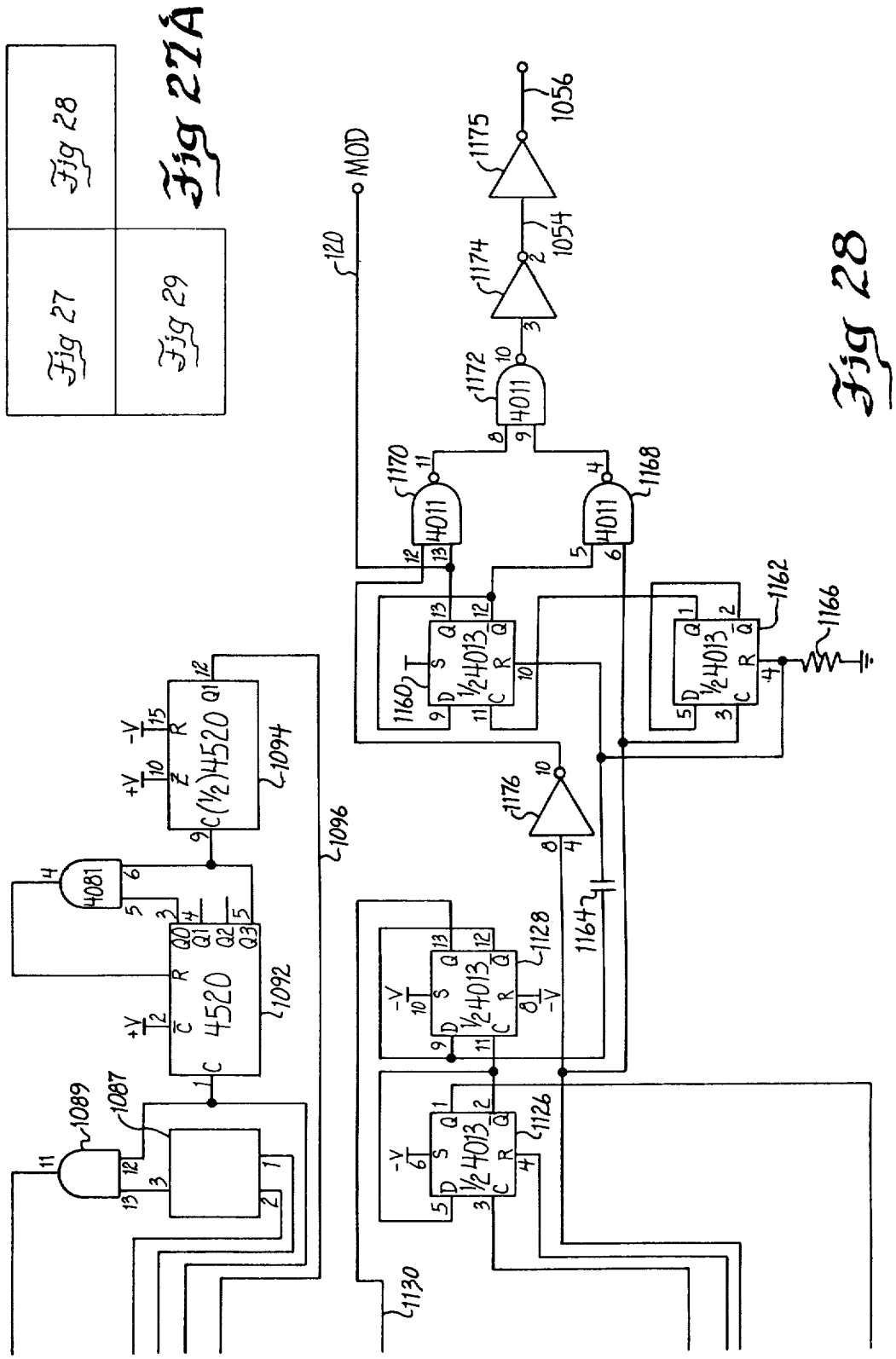

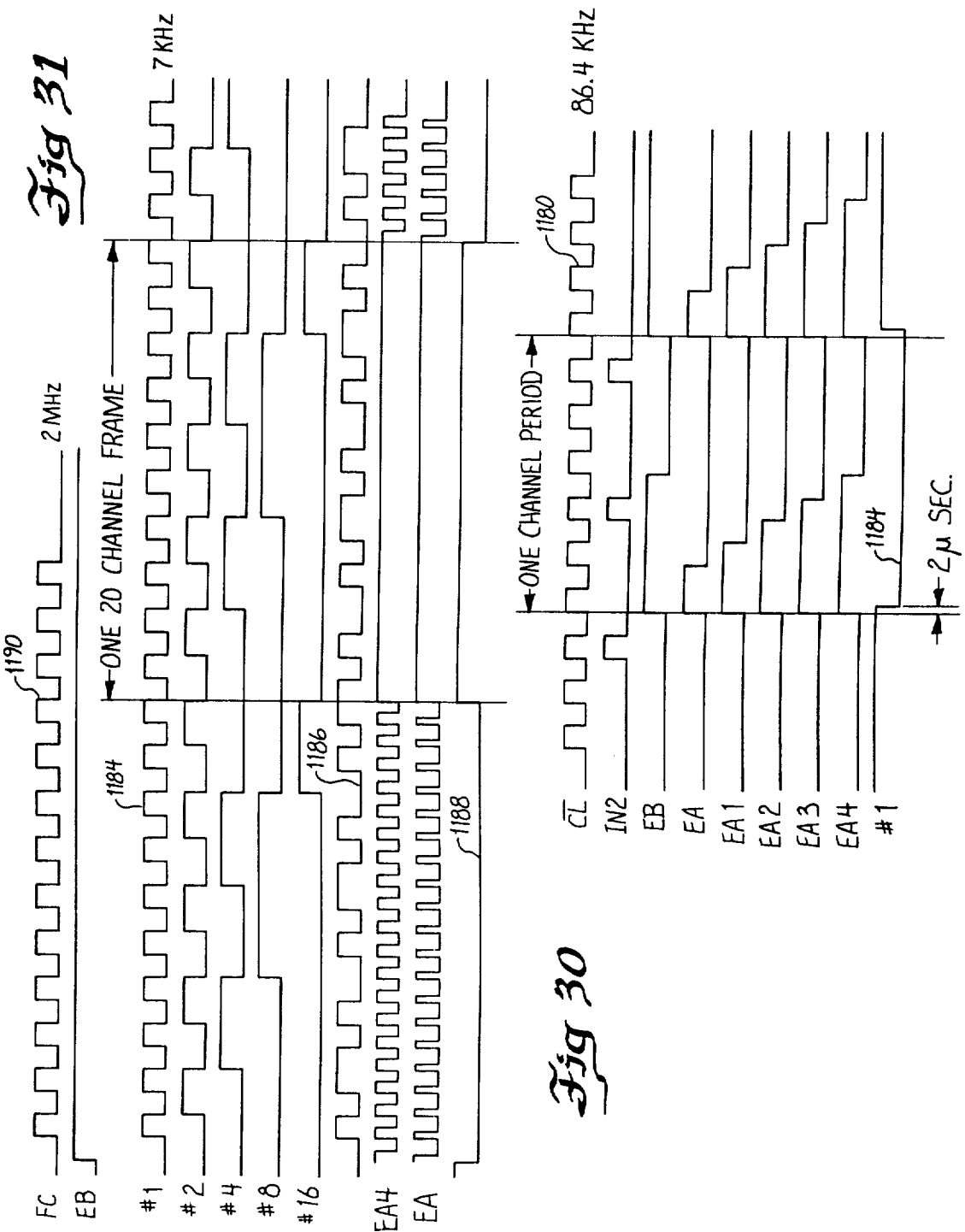

ELECTROENCEPHALOGRAPH

This is a continuation of application Ser. No. 914,272, filed June 9, 1978, now abandoned.

The present invention relates to electrical signal measurement and display apparatus and more particularly to electroencephalograph instruments.

An electroencephalograph (EEG) is a clinical multichannel instrument used to measure and display brain waves. In using such apparatus, a plurality of electrodes are attached to the scalp of the patient according to various patterns or "montages" well established in the art. The brain waves emanating from the brain of the subject are detected by the electrodes, amplified and displayed for viewing and interpretation by the operator. Typically, the display is in the form of a multi-channel recorder wherein each trace is made by a galvanometer type pen motor. Because of the type of analysis being made, there are a number of features which are either desirable or required in the design of an EEG instrument:

1. Because of the brain wave frequencies of interest, the signal processing portions of the instrument must have a band pass of from 0.16 to 70 Hz. However, the band pass characteristic for a particular electrode pair may have to be selectively altered to avoid interference from undesired signals due to muscle artifacts, tremors, or the like.

2. The amplitude of the brain wave signals varies greatly and in some instances may be extremely small. Accordingly, the signal processing portion of the instrument must have a gain of approximately 200,000 in order that an extremely small signal, in the order of ½ microvolt, may be amplified sufficiently to cause a deflection of the galvanometer of 1 mm. Furthermore, the amount of noise developed during amplification should be small enough to permit viewing of these extremely weak signals over the noise. In addition, since some channels may have stronger or weaker signals, the gain of the signal processing portion of the instrument must be variable on a channel to channel basis so that it can be reduced by a factor of approximately 20 when an extremely large amplitude brain wave signal is experienced, or increased by a factor of 4 for small signals.

3. Since the brain wave signals may vary greatly between different electrode pairs, and some electrode pairs may have more noise pickup than others, or interference due to artifact signals, etc. each signal processing channel should be independently controllable for selection of electrodes, adjustment of gain, and low frequency filtering. Such low frequency filtering is referred to in this specification as adjustment of the time constant of the channel to distinguish low frequency filtering from high frequency filtering which is also necessary.

4. To insure that the EEG instrument itself has no significant affect on the brain wave input signals, the instrument must have a high input impedance.

5. For the patient's safety, the instrument must have low leakage current. More particularly, in order to receive Underwriters Laboratory approval as an isolated patient connected instrument, the leakage current between instrument chassis ground and the patient must be less than twenty microamps with all electrodes tied together and with 160 volts peak to peak at 60 Hz applied.

6. The EEG instrument should be small in size and weight and be of readily maneuverable nature because of the typical mode of operation of an EEG operator. Quite often such apparatus is moved from room to room within a hospital and is often transported from hospital to hospital in order to take EEG measurement on widely scattered patients. Under such conditions ease of portability becomes very important.

7. Many EEG instruments are designed with a main frame having the bulk of the amplification and recording functions contained therein and a "head box" which is connected to the instrument main frame through a flexible cable. The head box may then be placed adjacent to the patient so that the electrodes which are connected to the head box can be attached to the patient's scalp. However, in typical EEG instruments of prior art design, the cable connecting the head box to the instrument main frame contains approximately forty wires and hence is quite bulky and hard to work with.

8. In most prior art EEG instruments the selection of electrodes and various other auxiliary functions has been accomplished by the use of mechanical switches. Such mechanical switches introduce noise which interferes with reception of the low level brain wave signals due to such things as dirty switch contacts, metal tarnishing and the like.

9. In taking an EEG from a patient, it is first necessary to a make a so-called impedance test to assure that the electrodes are making good electrical connection with the patient's scalp. In many prior art instruments this involves a manual function at the head box wherein the electrode to be measured is disconnected from its normal function and a measurement made between that electrode and all of the other electrodes in the system tied to ground. Each electrode is in turn selected by a manually actuatable switch and the impedance of each electrode measured. Furthermore, it is also desirable to provide a continuous measurement, during the taking of the EEG, to inform the operator whether or not one of the electrodes has dropped off of the patient's scalp. Such a test is commonly referred to as an open lead test and is shown for example in U.S. Pat. No. 3,859,988, which is assigned to the same assignee as the present invention.

10. There are also a number of other auxiliary functions which are normally employed in taking a conventional EEG. Thus, it is customary to select a number of electrodes the voltage of which is averaged in order to establish a desired "average reference" signal. This averaged potential is used as a reference for measurement with respect to one of the other electrodes. It is also customary to use two electrodes, such as the ear electrodes, and connect these electrodes together to form a reference which is then compared with the other electrodes in a selected montage.

11. Provision should also be made to eliminate the direct current component or slowly varying electrode drift component which may appear on the electrodes and interfere with the detection of the brain wave signals. Such interfering components may arise due to reactions with the skin of the patient, reaction to temperature changes, or an electrochemical reaction with the electrode which introduces slowly varying electrode drift components which must be removed. In prior art EEG instruments such components have typically been removed by inserting a high pass filter capacitor in series with the electrode lead. However, these capacitors may become charged during large voltage transients which introduce undesired frequencies into the input of the instrument. Additionally, the effect of a plurality of such capacitors in the system may have a cumulative effect which is undesirable. The d.c. or slowly varying voltage developed between different electrode pairs may be thousands of times greater than the brain wave signal which is to be detected. Furthermore, the d.c. components between different electrode pairs may have different polarities. For example, the voltage developed between a first electrode pair may consist of a plus one volt d.c. or slowly varying component on which is superimposed a brain wave signal of a few microvolts. The next electrode pair may have a d.c. or slowly varying component of minus one volt on which is superimposed the brain wave signal which is to be detected.

It would be desirable to employ a single signal path for amplification of the electrode pair signals and sequentially connect different electrodes to this signal path, rather than providing independent signal paths for each electrode pair. Such an arrangement would have the obvious advantages of a substantial reduction in the power, size and cost of the instrument. Prior art arrangements which propose this general type of operation are shown in Grichnik U.S. Pat. No. 4,037,586 and the references cited therein. However, when a common signal path is employed many problems arise if the above requirements of conventional EEG instruments are to be achieved. First, due to the nature of the signals which must be amplified extremely high gain may be required in the common signal path in the event that a very small amplitude brain wave signal is produced. However, this small brain wave signal may be superimposed on a relatively large d.c. or slowly varying component. If the signal is amplified without suppressing the d.c. component the voltage swing at the output of the common signal path must be enormous. For example, if a gain of 200,000 is required for the brain wave signal and a one-volt d.c. component is present on the electrode, the output of the common amplifier would have to swing plus or minus 200,000 volts. On the other hand, if the d.c. component is suppressed, such suppression must be on an individual channel basis because the d.c. components of adjacent channel signals may vary widely in either amplitude or polarity. For example, the d.c. component for one electrode pair may be plus one volt and the d.c. component for the next pair minus one volt. If a common reference capacitor is used to remove the d.c. these adjacent channels would sum to zero so that the d.c. component would be lost.

Secondly, the selective switching or sampling of the signal voltages produced at a number of electrode pairs renders the system susceptible to relatively high frequency signals which may be produced by low frequency radio stations or other transmitters of low frequency RF. This is because of the fact that the low frequency RF signal may heterodyne with the sampling frequency to produce a difference frequency component which will fall into the brain wave signal band, a condition commonly referred to as aliasing. Accordingly, some means must be provided to insure that a stray pickup signal which may come from a low frequency RF source will not heterodyne with the sampling frequency and yield a difference frequency which will be falsely interpreted as a brain wave signal in the EEG instrument.

Thirdly, when d.c. or base line suppression is performed on an individual channel basis the normal reset function whereby the effects of large undesired artifact signals are removed, introduces further problems. This is because electronic switches must be employed for selection of the individual channel time constants due to the relatively high sampling frequencies involved. However, it has been found that stray capacitances exist between the control line and the terminals of the electronic switches. Accordingly, when the original time constant is restored after reset, the control pulse which is supplied to the control line of each switch to control opening and closing of the switch actually charges the time constant capacitor through the stray capacitances and causes an undesired offset in each channel. Furthermore, this stray capacitance may vary as must as fifty percent from one electronic switch to another so that any compensation for such offset potentials must be done on an individual channel basis if additional gain is provided after the switch.

Fourthly, if a common signal path is used for all electrode pairs this path must have a band width that is much greater than conventional EEG instruments. For example, if twenty channels are provided the band width in the common signal path must be at least twenty times the band width of a signal channel. Furthermore, this extremely wide band width must be provided while maintaining high but variable gain through the amplifier and maintaining the common signal path isolated from system ground for patient isolation and protection. Also, since selection of electrode pairs must be done at the input of the common signal path and must be done by electronic switches, these switches and the control circuitry therefor must be isolated from system ground.

It is, therefore, an object of the present invention to provide a new and improved multi-channel instrumentation system wherein a common signal path is provided for a plurality of input signals and facilities are provided for electrically isolating the input of said common signal path from system ground.

It is another object of the present invention to provide a new and improved EEG system in which a common signal path is employed for amplifying a plurality of selected electrode pair signal voltages while electrically isolating the electrode pair selecting means from system ground.

It is a further object of the present invention to provide such a new and improved EEG system wherein the electrode pair selecting means is included in a portable head box which may be placed adjacent to the patient to be tested.

It is another object of the present invention to provide such a new and improved EEG system wherein facilities are included in the head box for testing the impedance of any selected one of the patient electrodes and providing a visual indication of the magnitude of such impedance.

It is a further object of the present invention to provide such a new and improved EEG system wherein facilities are provided for selecting a set of patient electrodes which are connected together and used as an average or reference potential for one input of the common signal path.

It is another object of the present invention to provide such a new and improved EEG system wherein facilities are provided for calibrating the common signal path by applying a d.c. calibration signal to the input thereof by means isolated from system ground.

It is a further object of the present invention to provide such a new and improved EEG system wherein facilities are provided within the head box for selectively connecting the designated averaging electrodes together to a common output which may be selected in the same manner as a patient electrode.

It is another object of the present invention to provide such a new and improved EEG system wherein facilities are provided for detecting electrode imbalance in any selected electrode pair.

It is a further object of the present invention to provide such a new and improved EEG system wherein the current which can be drawn from the patient ground electrode is limited to a small value to provide for the safety of the patient in the event of malfuncting of the electrode selecting means.

It is another object of the present invention to provide such a new and improved EEG system wherein facilities are provided in said common signal path for removing the d.c. components of the electrode pair signal voltages.

It is a further object of the present invention to provide such a new and improved EEG system wherein facilities are provided in said common signal path for selectively varying the gain thereof on an individual channel basis.

It is another object of the present invention to provide such a new and improved EEG system wherein low-pass filter means are employed in said common signal path to remove said d.c. components and means are provided for varying the characteristic of said low-pass filter means on an individual channel basis.

It is a further object of the present invention to provide such a new and improved EEG system wherein an electronically alterable ROM is employed to store selected patterns of electrode pairs and microprocessor means are provided for selectively altering the electrode pairs of any of said stored patterns.

It is another object of the present invention to provide such a new and improved EEG system wherein said microprocessor means may also be employed selectively to alter the gain of said common signal path on an individual channel basis.

It is a further object of the present invention to provide such a new and improved EEG system wherein said microprocessor means is employed to vary the time constant of said low-pass filter means on an individual channel basis.

It is another object of the present invention to provide such a new and improved EEG system wherein low-pass filter means are provided in said common signal path for selectively removing high frequency components from the individual channel signal paths.

It is a further object of the present invention to provide such a new and improved EEG system wherein said microprocessor means may be employed selectively to control said averaging electrode selecting means.

It is another object of the present invention to provide such a new and improved EEG system wherein patient electrode address data is transmitted to said head box in serial bit form to control connection of electrode pairs to said common signal path.

It is a further object of the present invention to provide such a new and improved EEG system wherein the data transmitted to said head box includes at least one bit which is employed selectively to control said averaging electrode connecting means.

Briefly, the EEG system of the present invention utilizes a common signal path for all channels of the instrument while employing a portable head box which may be placed next to the patient to be tested. All of the input selection equipment which is isolated from system ground is included in this head box, including the electronic switches for connecting selected electrode pairs to the input of the common signal path. An electrode averaging function is provided wherein a designated set of electrodes may be selectively connected together and used as a reference to compare with any one of the patient electrodes the electronic circuitry for selecting the electrodes to be included in the average and for connecting the selected electrodes together and to one input of the common signal path is also included in the head box and is isolated from system ground.

Facilities are provided for connecting two designated electrodes together, such as the ear electrodes, and using them as a reference input, the electronic circuitry for accomplishing this function cooperating with the circuitry for the selection of electrode pairs for other channels of the instrument. The circuitry for selecting the car electrodes as a reference is also isolated from system ground and is included in the head box. Additionally, electrode impedance testing facilities are provided, the electronic circuitry for selecting a particular electrode and connecting it to one input of the common signal path and for connecting all of the other electrodes together and to the other input being compatible with normal switching of electrode pairs to the input and also being isolated from system ground and included in the head box.

Electronic circuitry is provided for applying a calibration signal to the common signal amplifying path which does not interfere with electrode pair switching to the input and is also isolated from system ground and included in the head box. Also, an arrangement for detecting electrode imbalance is included which is isolated from system ground, does not interfere with electrode pair switching, and is included in the head box.

Since electronic switches are employed to connect the electrodes which are attached to the patient's head to the common signal path and these switches are controlled by large amplitude control pulses, facilities are provided for protecting the patient in the event a switch control line becomes shorted to a switch terminal so that a relatively large voltage is directly connected to a patient electrode and is hence applied to the patient's head.

The invention, both as to its organization and method of operation, together with further objects and advantages thereof, will best be understood by reference to the following specification taken in connection with the accompanying drawings in which:

FIGS. 1, 2 and 3 when positioned as shown in FIG. 3A comprise a block diagram of the EEG system of the present invention;

FIG. 3B is a pictorial diagram of the channel display of the system of FIGS. 1, 2 and 3;

FIG. 4 is a pictorial diagram of the keyboard layout of the system of FIGS. 1, 2 and 3;

Figure 1:
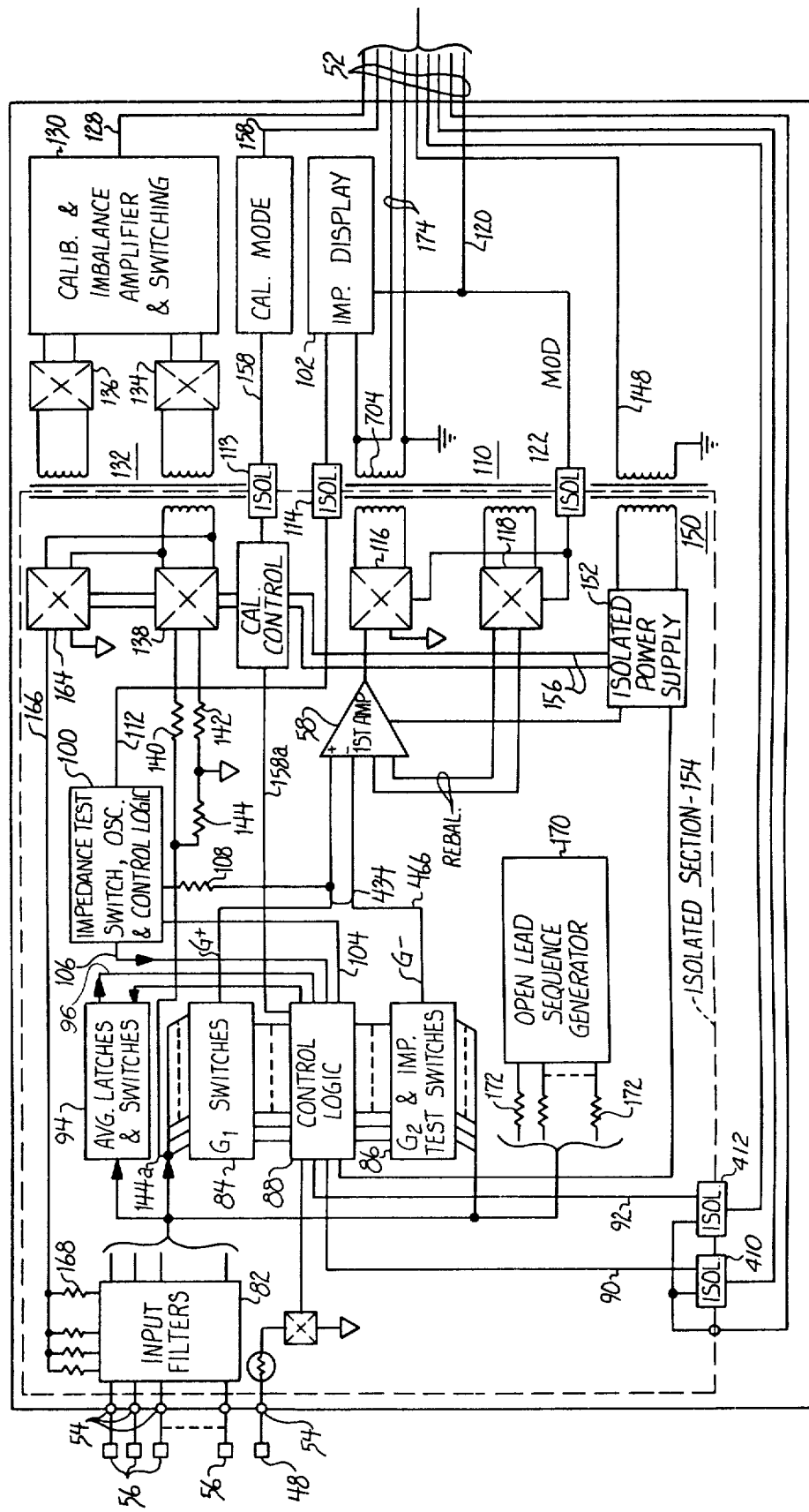
Figure 2:
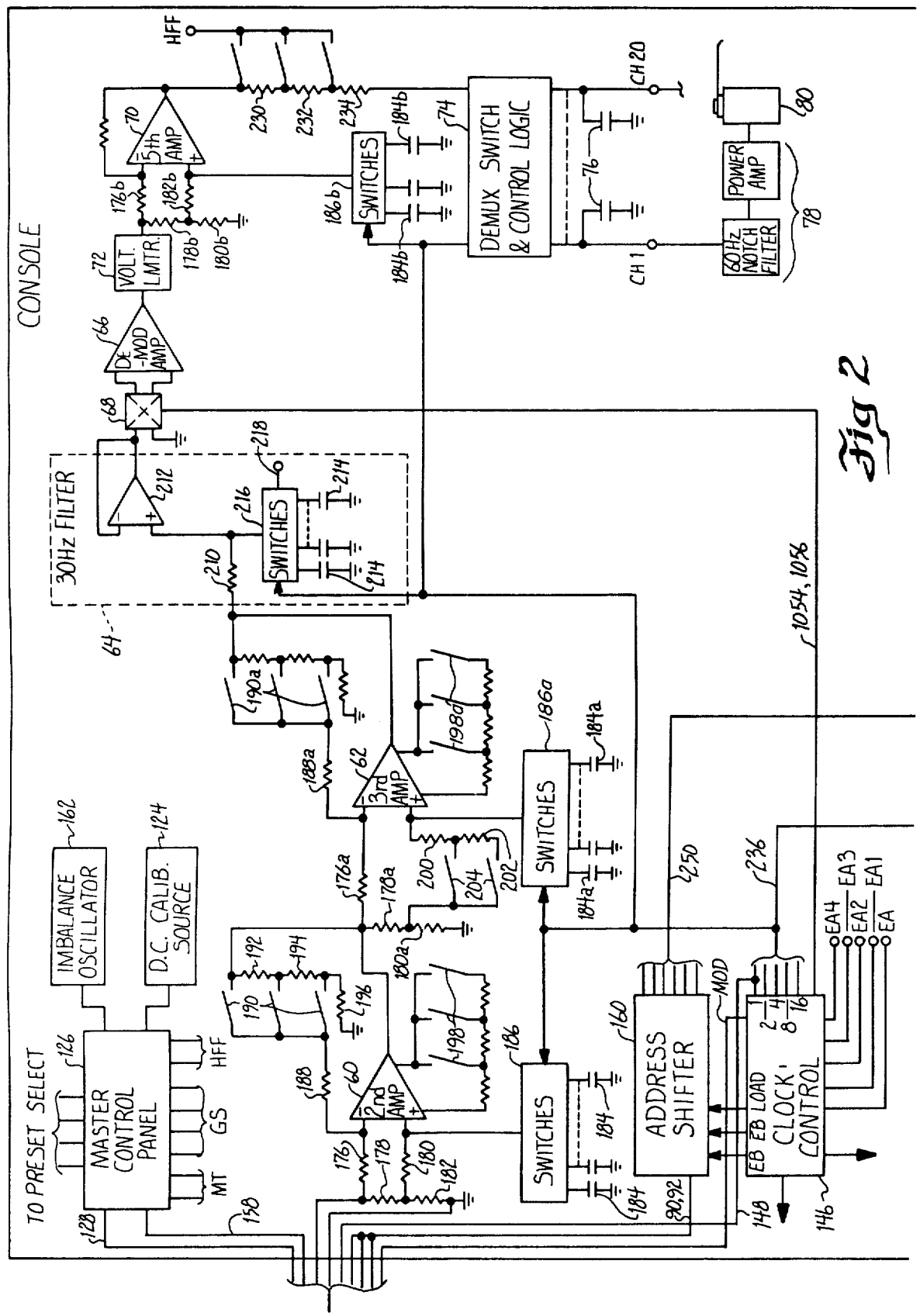
Figure 7A:
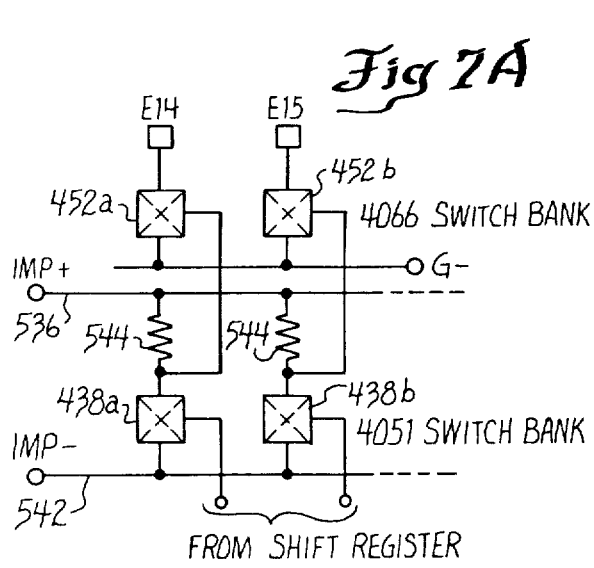
Figure 9:
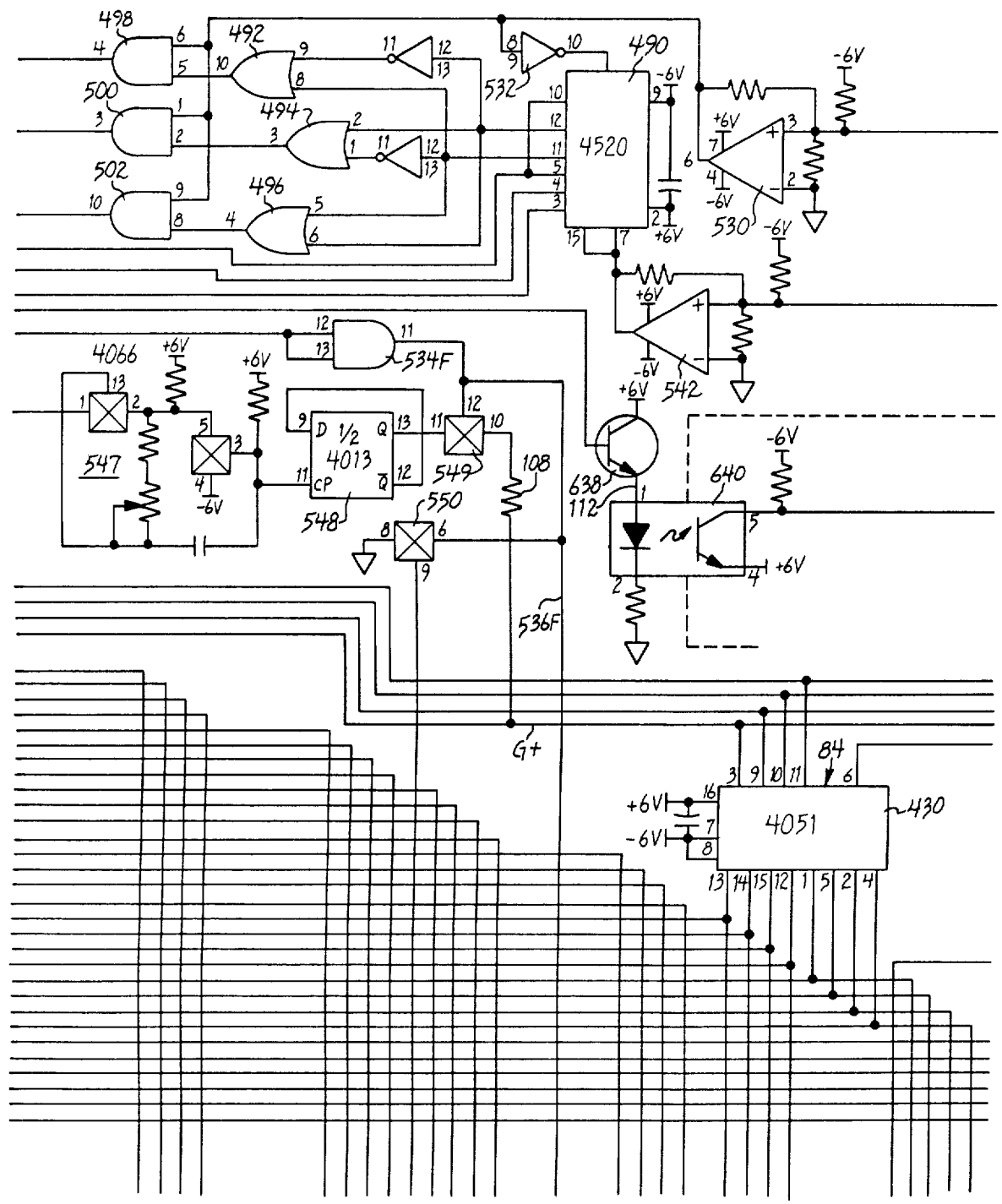
Figure 10:
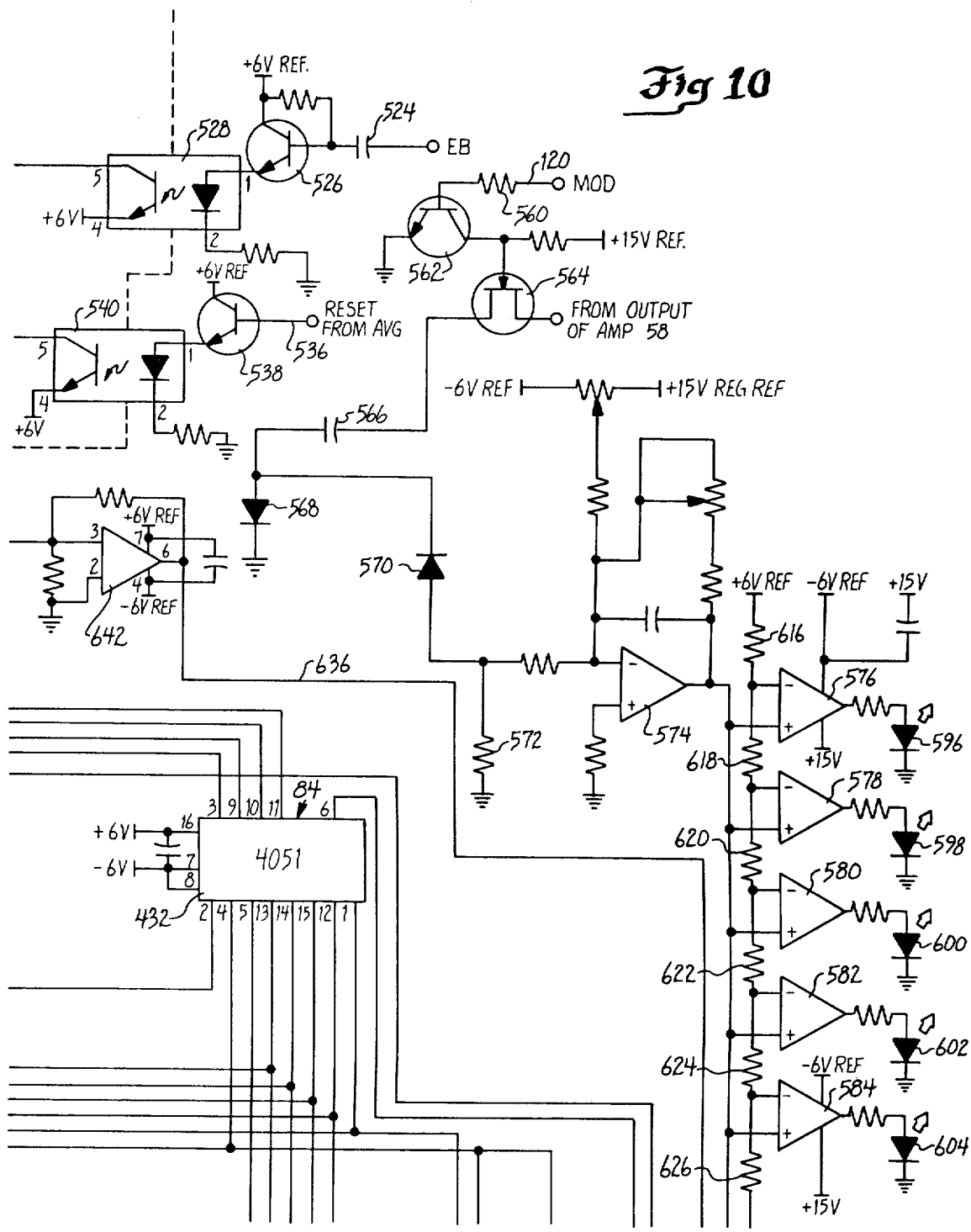
Figure 11:
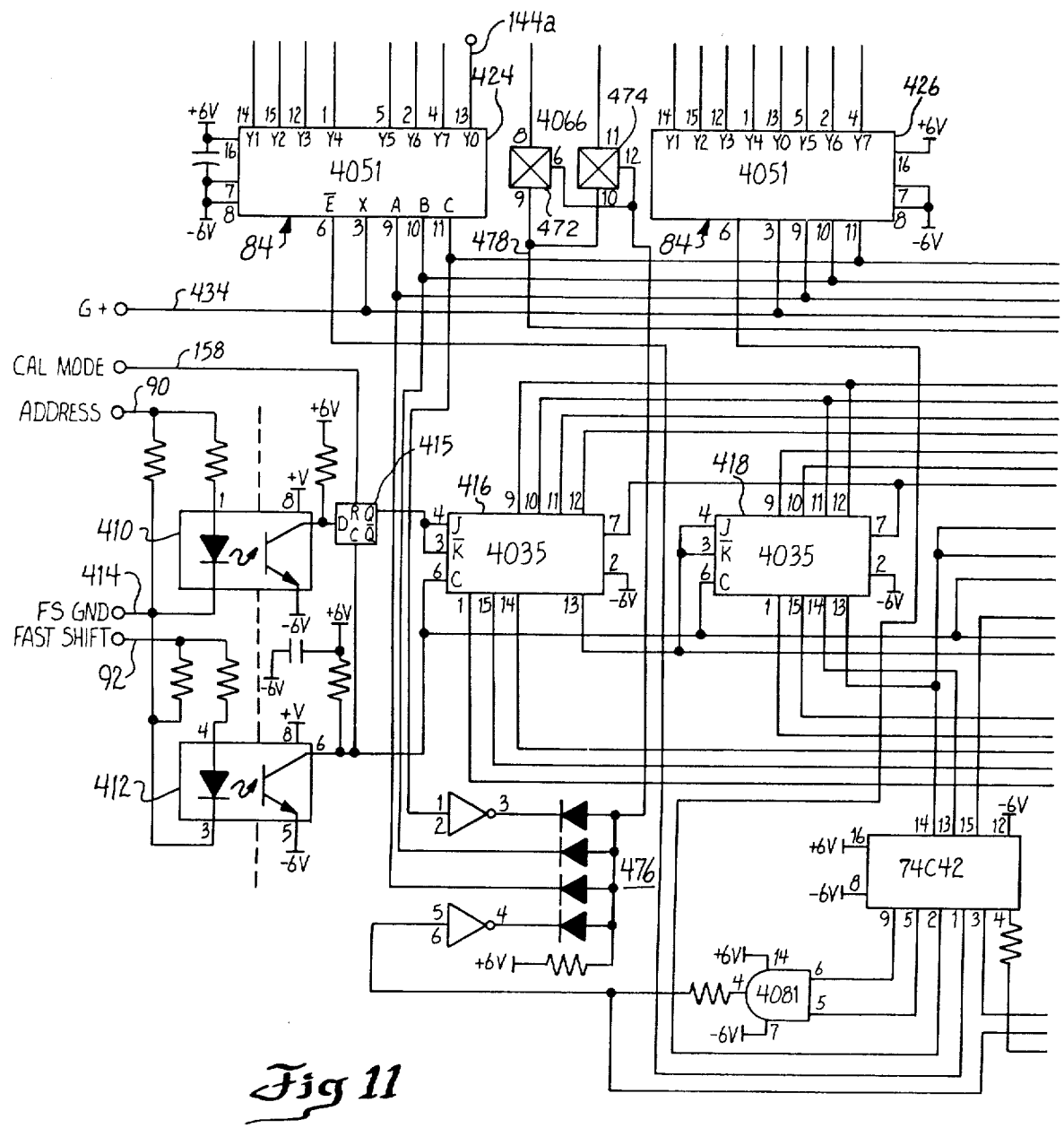
Figure 12:
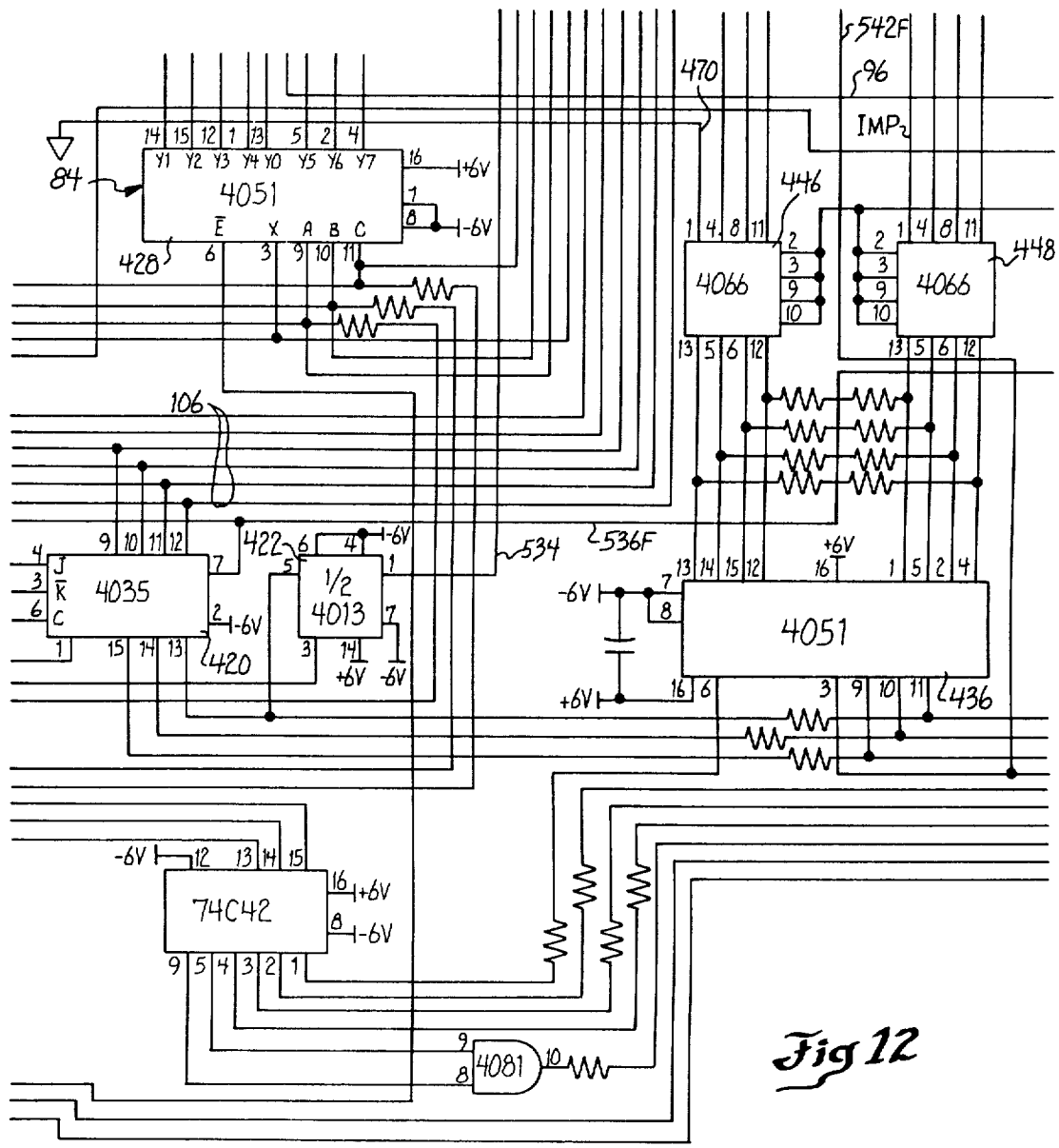
Figure 13:
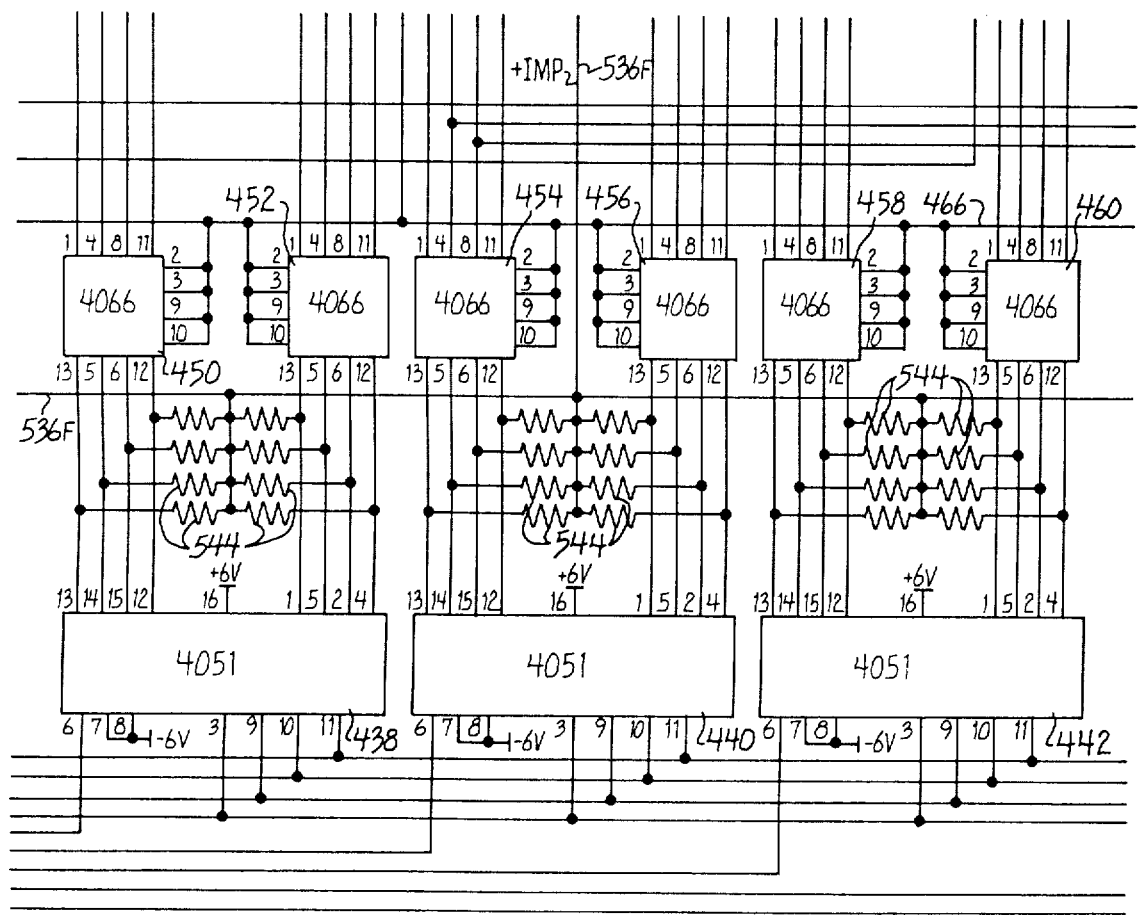
Figures 14, 14A:
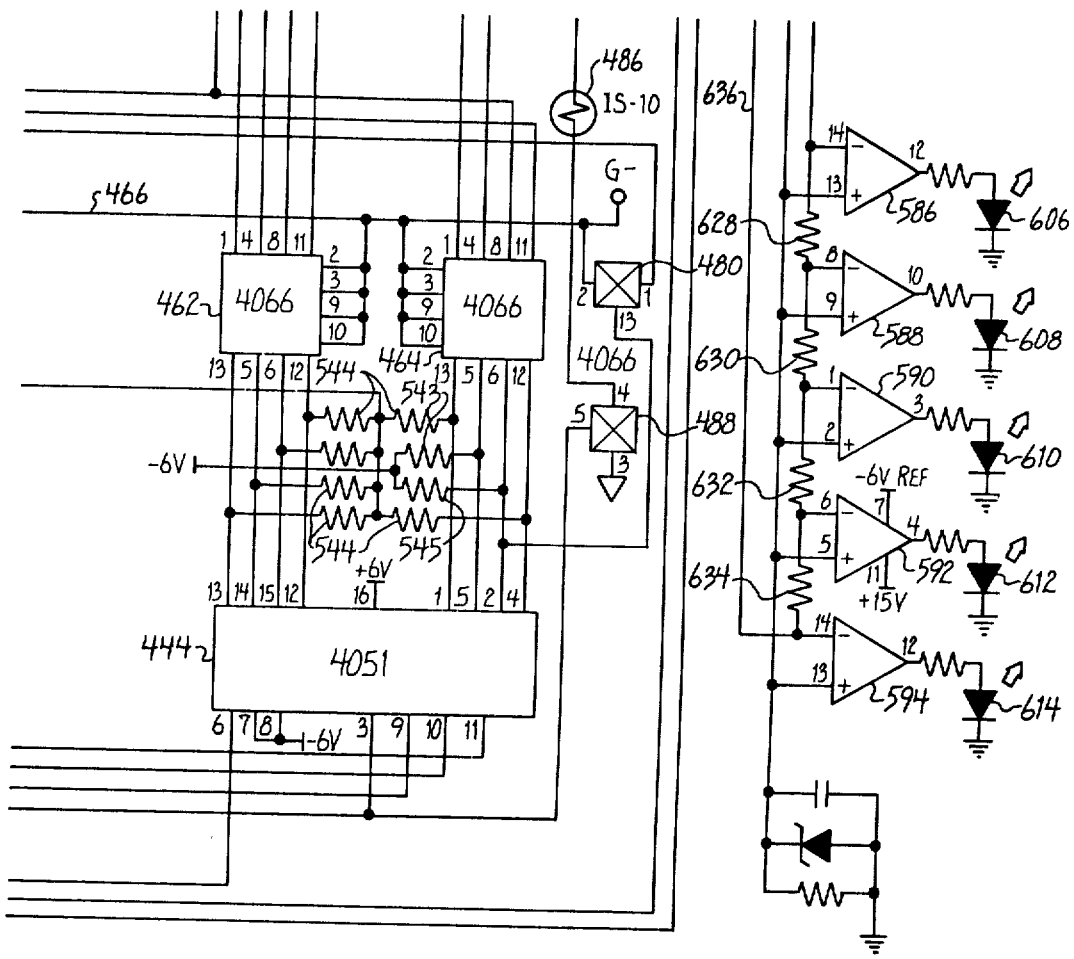
Figure 16:
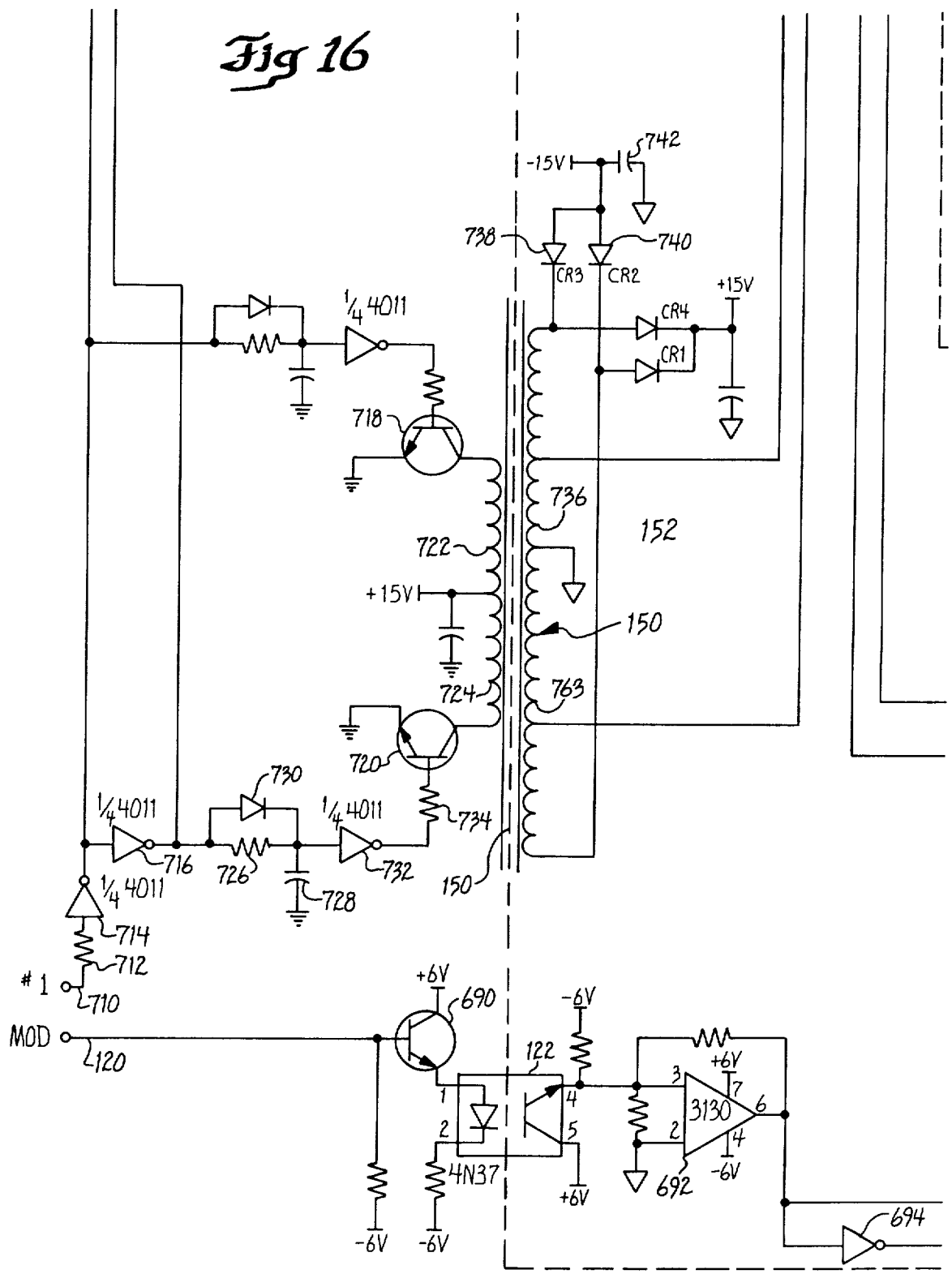
Figure 17:
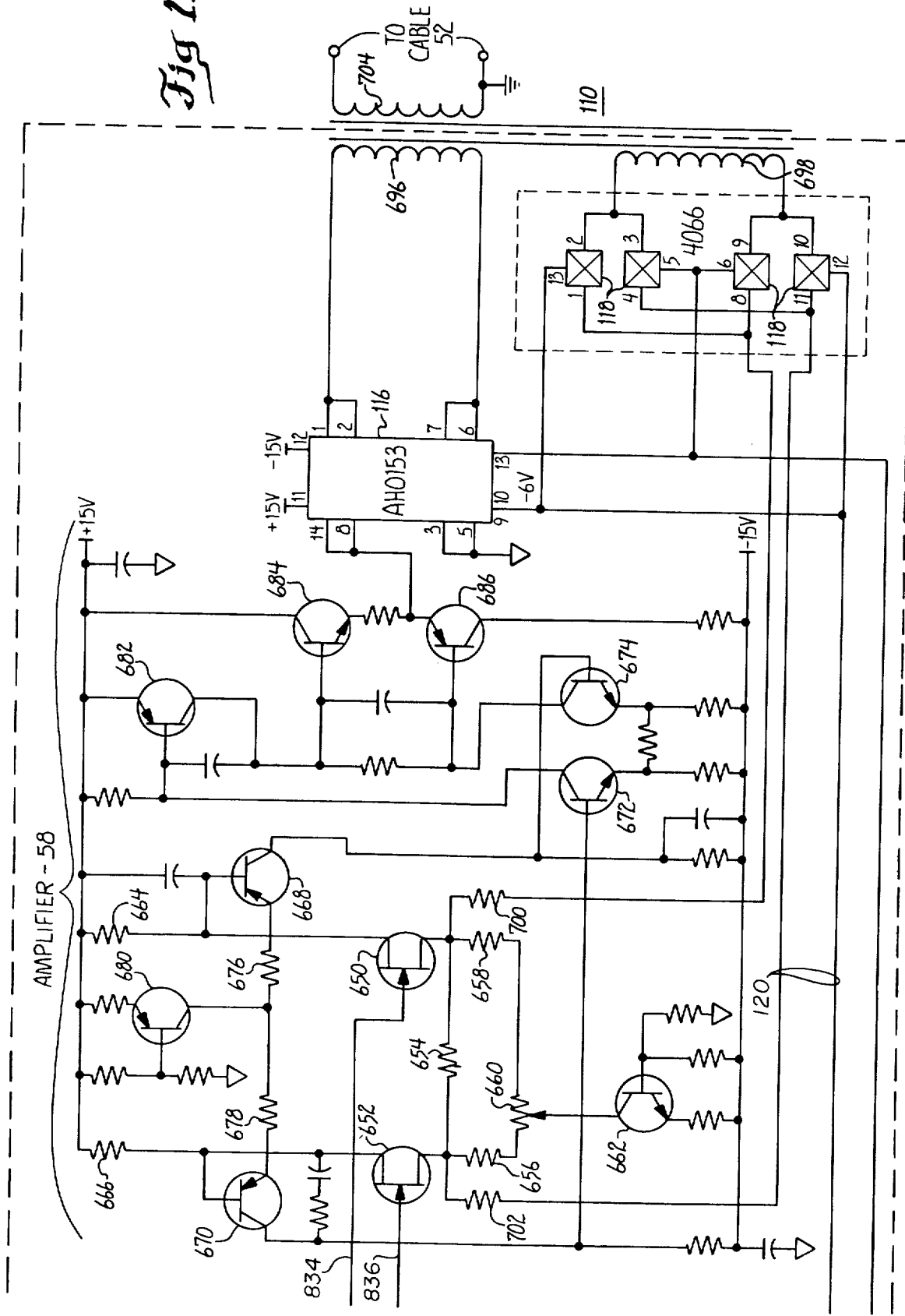
Figure 18:
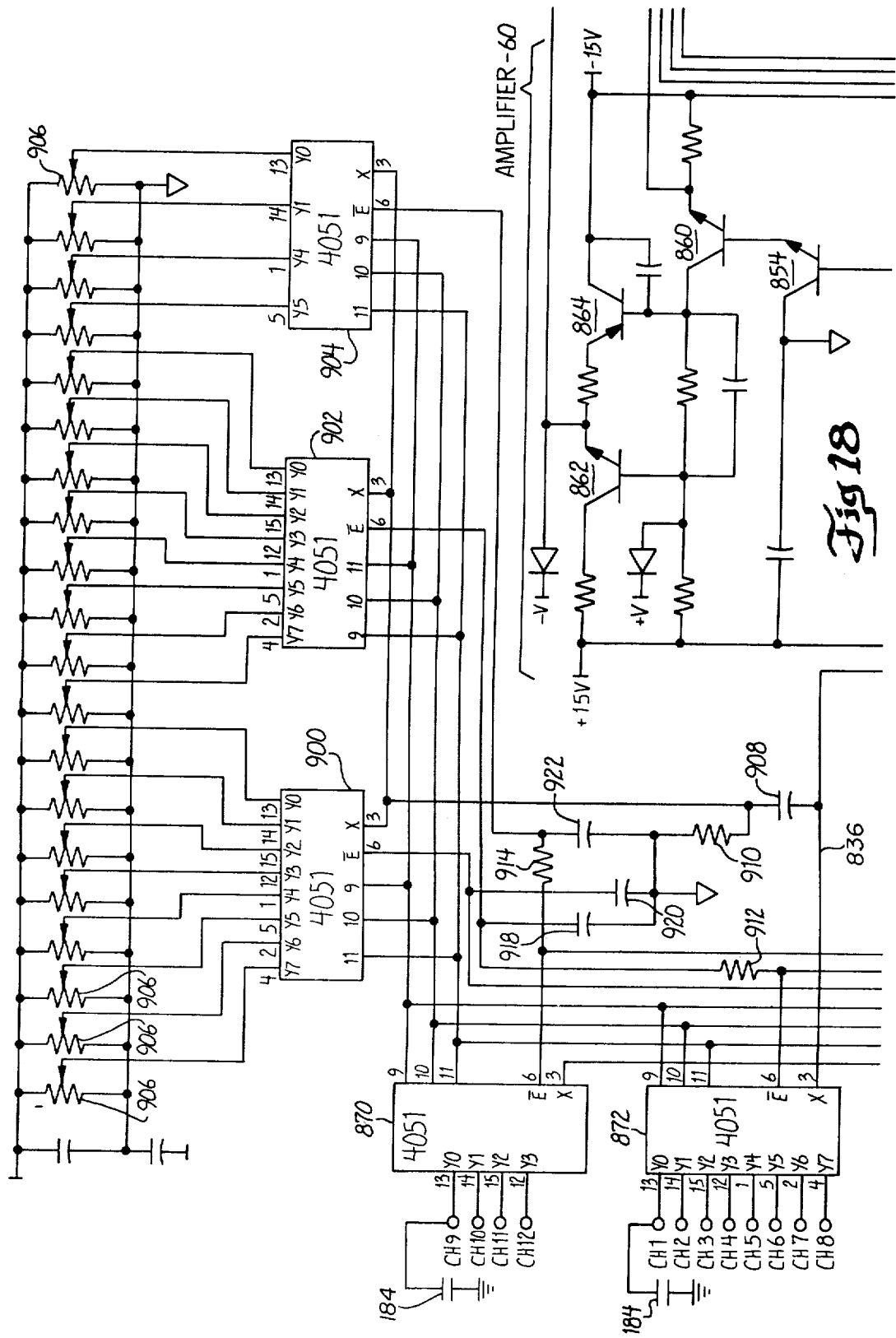
Figure 19:
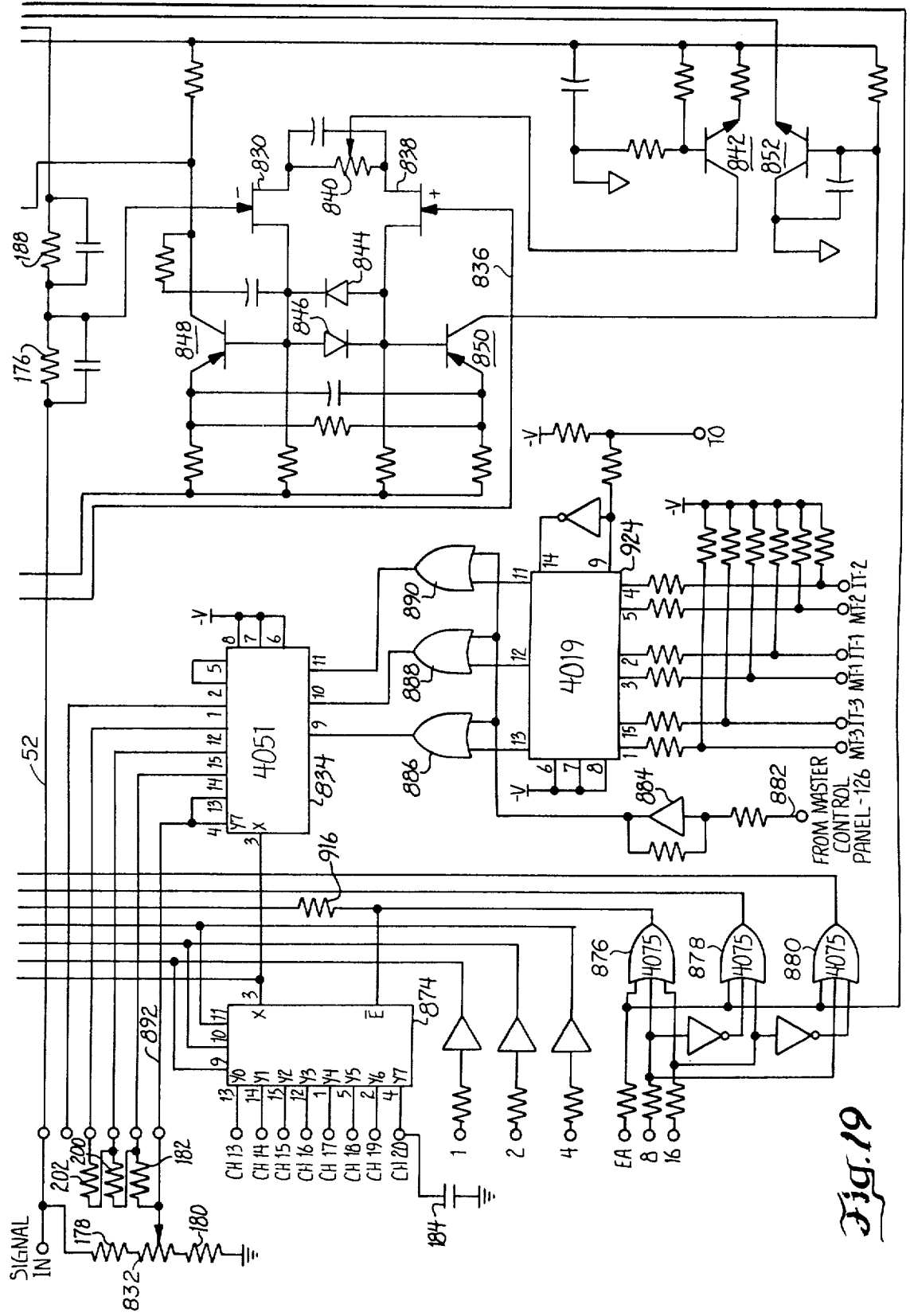
Figure 21:
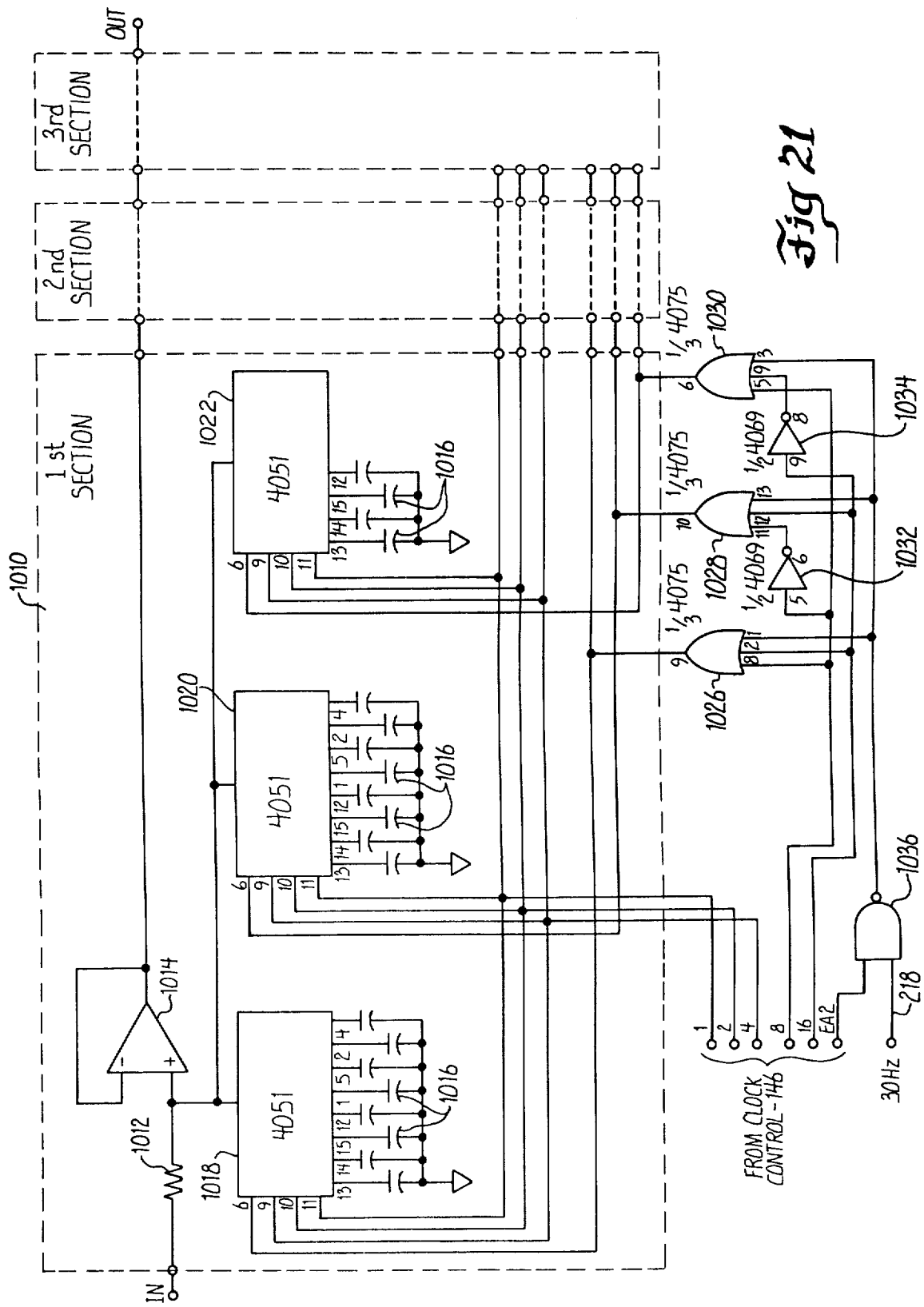
Figure 22:
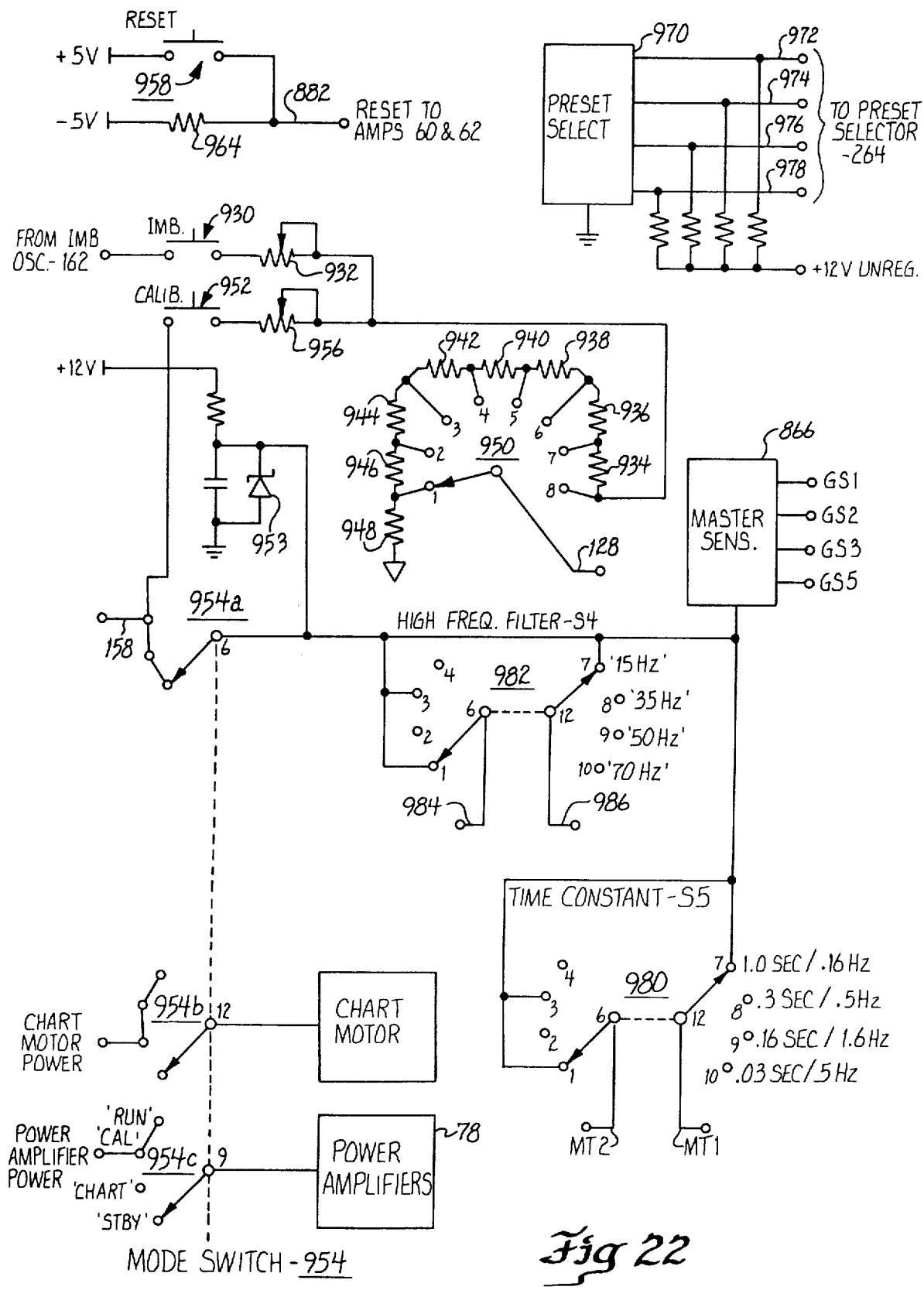
Figure 23:
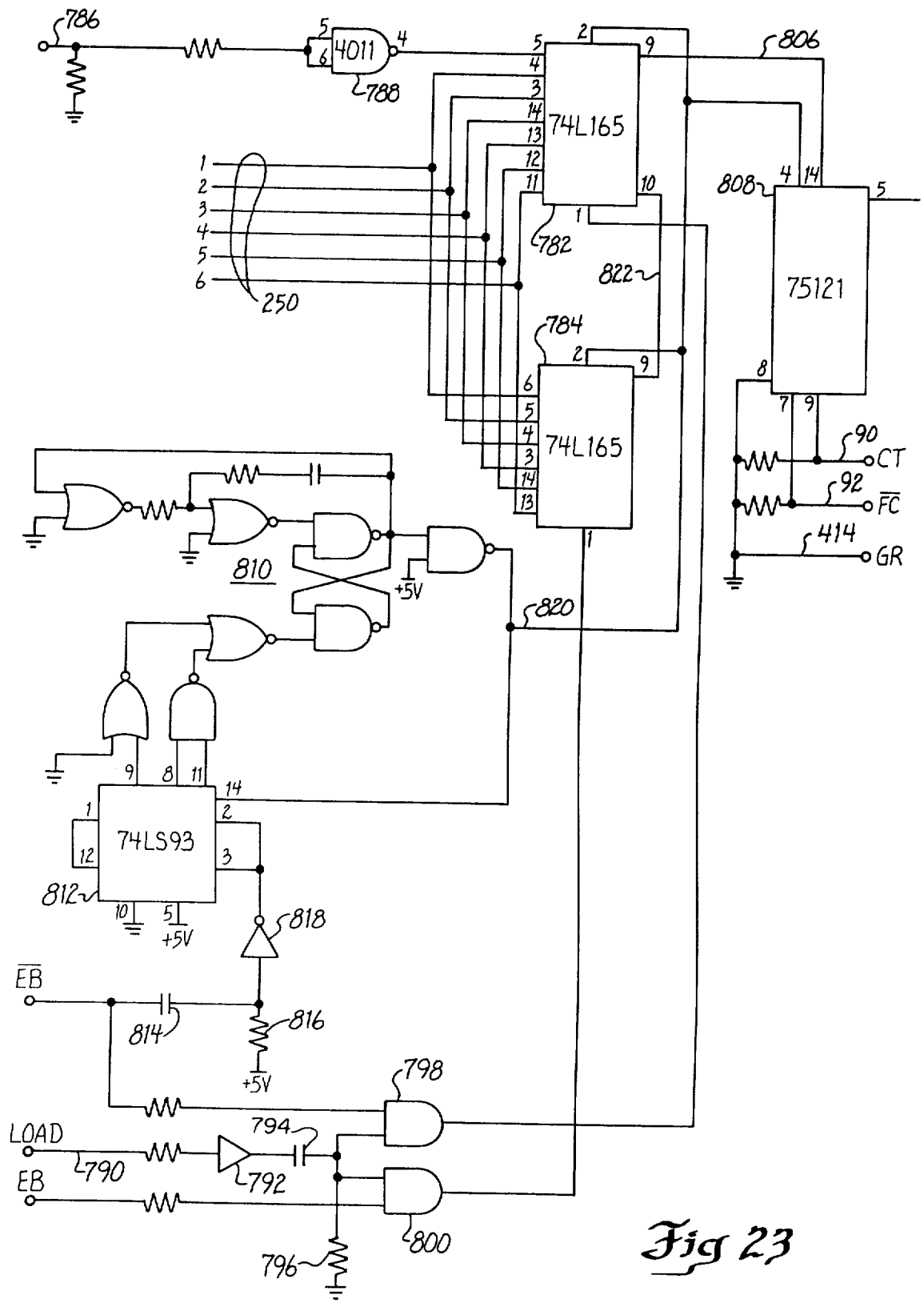
Figure 26:
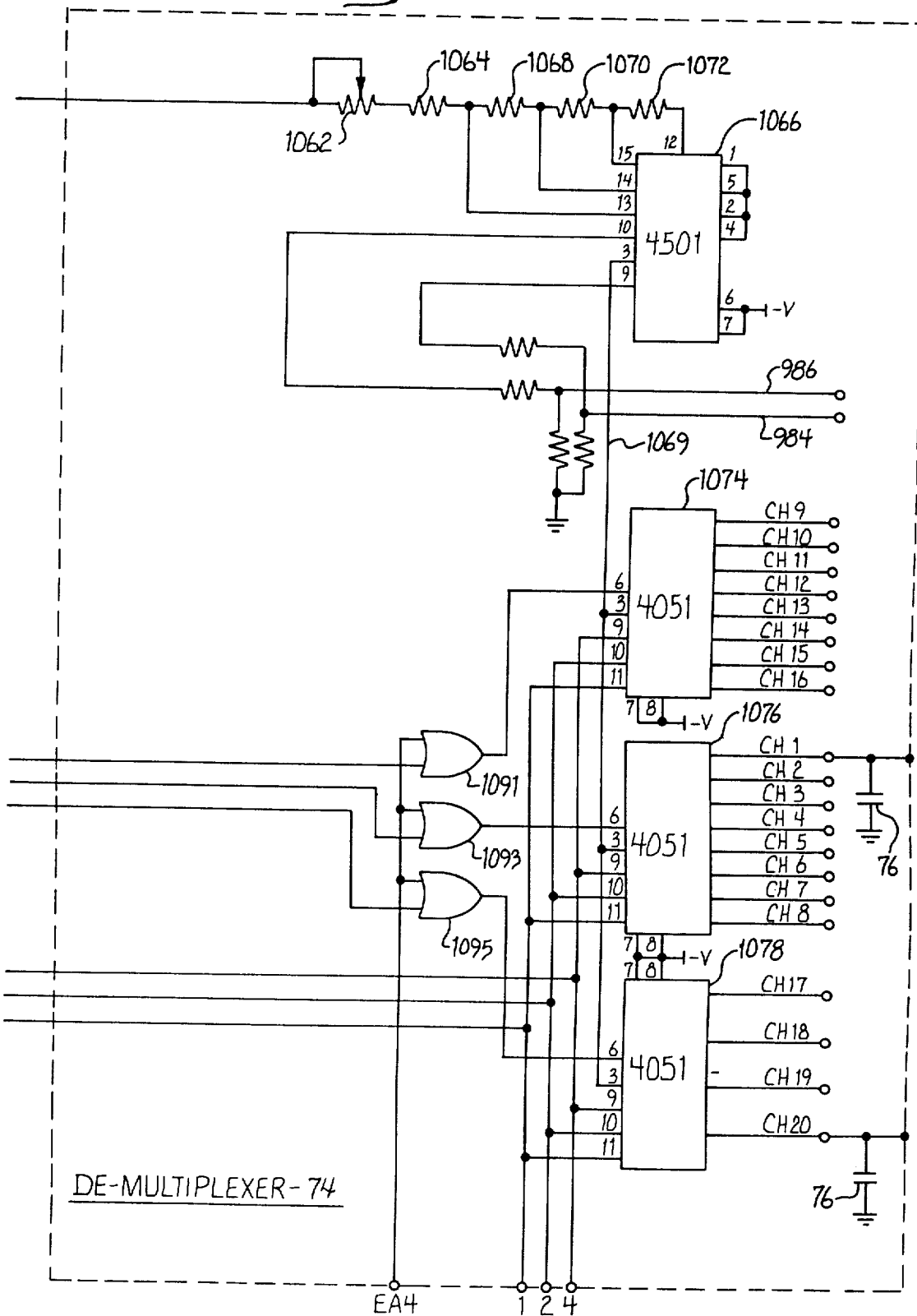
Figure 22:
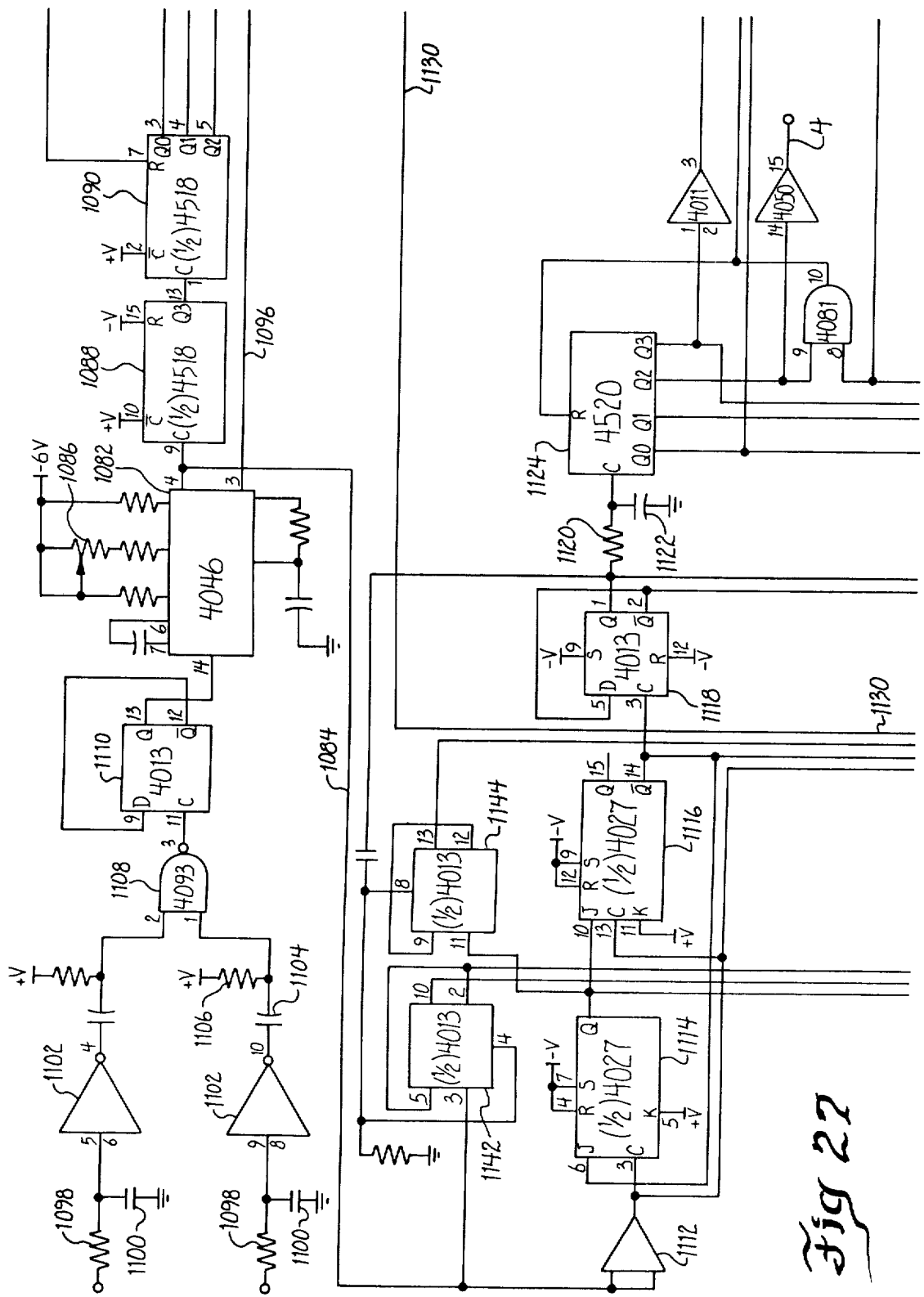
Figure 29:
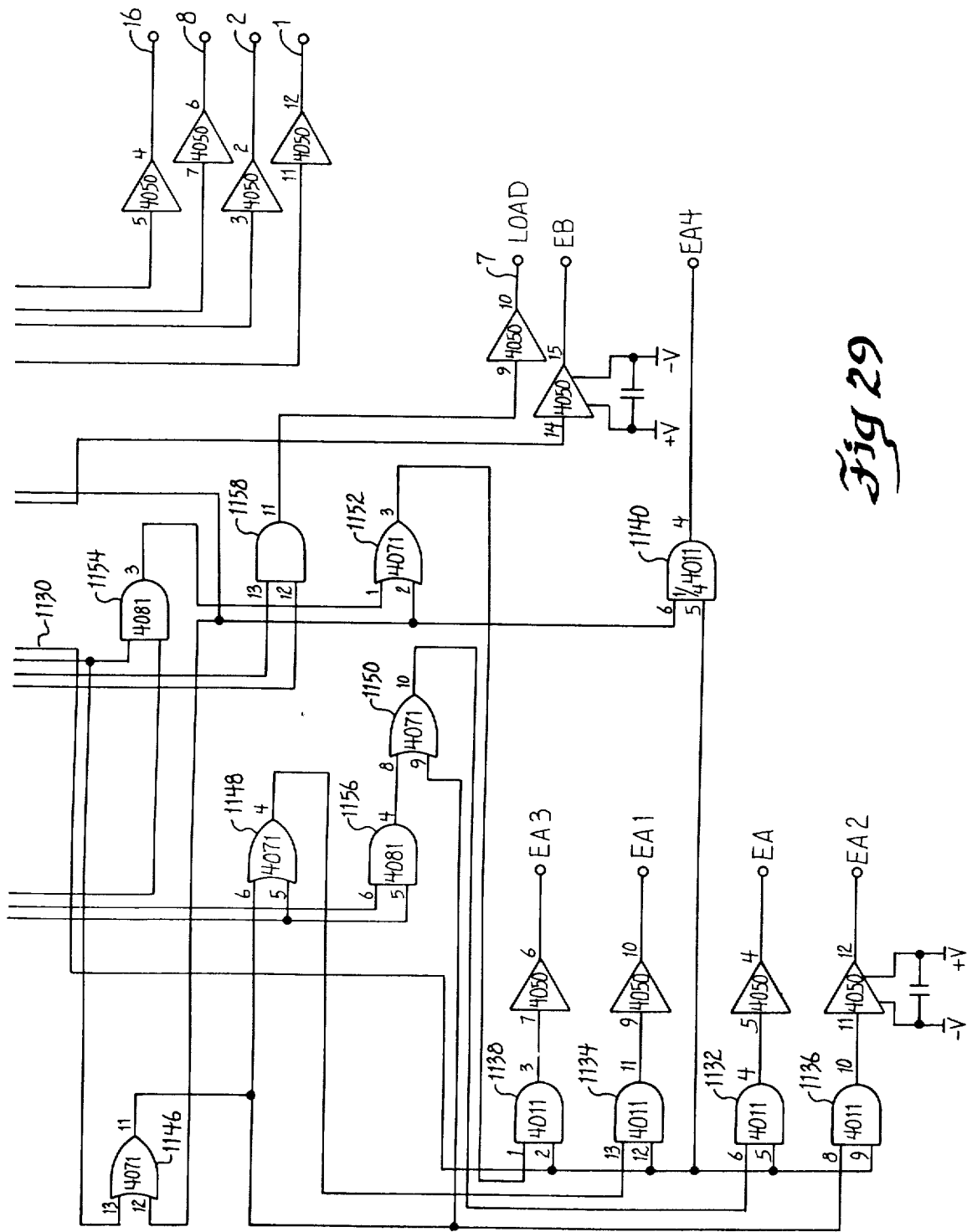

FIGS. 7 to 14, inclusive, when arranged in the manner shown in FIG. 14A, comrpise the schematic diagram of the electrode selection equipment included in the head box of the system of FIGS. 1, 2 and 3;

FIG. 7A is a schematic diagram illustrating the operation of the impedance test facilities of FIGS. 7 to 14;

FIGS. 15, 16 and 17, when arranged in the manner shown in FIG. 15A, comprise the schematic diagram of the input amplifier and other facilities included in the head box of the system of FIGS. 1, 2 and 3;

FIGS. 18, 19 and 20, when arranged in the manner shown in FIG. 18A comprise the schematic diagram of the second amplifier in the system of FIGS. 1, 2 and 3;

FIG. 19A is a schematic diagram illustrating the charge compensation system used in the second amplifier shown in FIGS. 18, 19 and 20;

FIG. 21 is a schematic diagram of the selectable 30-Hz filter in the system of FIGS. 1 2 and 3;

FIG. 22 is a schematic diagram of the master control panel in the system of FIGS. 1, 2 and 3;

FIG. 23 is a schematic diagram of the address shifter employed in the system of FIGS. 1, 2 and 3;

FIGS. 24, 25 and 26, when placed side by side comprise a schematic diagram of the demodulation amplifier, voltage limiter, fifth amplifier and demultiplexer portions of the system of FIGS. 1, 2 and 3;

FIGS. 27, 28 and 29, when arranged in the manner shown in FIG. 27A comprise the schematic diagram of the clock control facilities in the system of FIGS. 1, 2 and 3; and FIGS. 30 and 31 are timing diagrams illustrating the operation of certain portions of the systems of FIGS. 1, 2 and 3.

Referring now to the drawings, and more particularly to the system block diagram shown in FIGS. 1 and 2 thereof, the EEG system of the present invention is therein illustrated as comprising a head box 50 which is portable so that it may be placed next to the patient to be tested, the head box 50 being interconnected by means of a multi-conductor cable 52 with the main console of the EEG system. The head box 50 is provided with a plurality of input terminals 54 which are adapted to be connected to different patient electrodes 56, the electrodes 56 being secured to the scalp of the patient in a conventional manner.

Considered very generally, the EEG system of the present invention provides a common signal path for amplifying the signal voltages developed between selected pairs of the electrodes 56. The first amplifier 58 of this common signal path is located in the head box 50 and is isolated from the system ground of the main console by means to be described in more detail hereinafter. The common signal path also includes a second amplifier 60, a third amplifier 62, a 30-Hz filter 64 which is selectable on an individual channel basis, a demodulation amplifier 66 the input of which is switched in polarity by means of the reversing switches 68 to remove a frequency component introduced in the output of the first amplifier 58, a voltage limiter 72, a fifth amplifier 70 and a demultiplexer 74 which is provided with a number of output channels corresponding to the number of traces desired on the common recording medium of the EEG system.

In the illustrated embodiment, a series of twenty output channels are provided so that a demultiplexer 74 is provided with a series of twenty output capacitors 76 which are individually connected to the recording channels 78. Each recording channel 78 may include a 60-Hertz notch filter and a suitable power amplifier for driving a galvanometer type pen motor indicated generally at 80 so that a series of twenty traces are simultaneously produced on a common recording medium corresponding to different selected pairs of the electrodes 56.

Considering now in more detail the manner in which selected pairs of the electrodes 56 may be connected to the isolated input of the first amplifier 58, the input terminals 54 of the head box 50 are connected through individual input filters indicated generally at 82 to a first group of switches identified as the G1 or grid number one control switches 84. The filters 82 are also connected to a second set of switches identified as the G2 or grid number two switches 86. The G1 and G2 switches 84 and 86 are controlled by control logic 88 so that any one of the patient electrodes 56 may be connected through one of the G1 switches 84 to the G+ conductor input of the first amplifier 58 while at the same time any one of the electrodes 56 may be connected through one of the G2 switches 86 to the minus input of the amplifier 58. Accordingly, the brain wave signal voltages developed between selected pairs of the electodes 56 are successively supplied to the input of the first amplifier 58 during successive channel periods which recur in repetitive twenty-channel frames.

The control logic 88 includes a thirteen-bit shift register of the serial in to parallel out or parallel in to parallel out type. During the normal mode of operation of the EEG system, data is serially supplied over the address line 90 to the input of this shift register at the start of each channel period and rapidly shifted into this register by means of fast clock pulses supplied over the conductor 92. The first six bits of data registered in the control logic 88 control the switches 84 so as to connect a selected one of the patient electrodes 56 to the plus input of the amplifier 58. The next six bits of data supplied over the address line are employed to control the G2 switches so that one of the electrodes 56 is connected to the minus input of the amplifier 58.

In accordance with an important aspect of the present invention facilities are provided for connecting a selected group of the patient electrodes 56 together to provide an average or reference potential level which may be selectively connected to either input of the amplifier 58 during any desired channel period. Any one of the patient electrodes 56 may then be compared with this reference level by connecting that electrode through one of the switches 86 to the other input of the amplifier 58. More particularly, the outputs of the first twenty-three patient electrodes 56 are supplied to a series of twenty-three averaging latches and switches indicated generally at 94. The control logic 88 includes a counter which sequentially enables the latches 94 during twenty-three successive channel periods, and the thirteenth bit of data supplied over the address line 90 to the shift register in the control logic 88 is employed during successive channel periods to set different ones of the enabled latches so as to select the corresponding ones of the first twenty-three electrodes which are to be included in the average. The averaging latches control corresponding switches which are connected to a common output 96 which may be selected by one of the switches 84 or 86 during any desired channel period so that the average of the selected electrodes is supplied to one input of the amplifier 58 during this channel period. In this connection it will be understood that the latches 94 are first sequentially enabled and set during twenty-three successive channel periods, after which these latches remain set and provide the desired average output on the conductor 96 during the remainder of the test. However, the electrodes included in this average may be varied at any time, as will be described in more detail hereinafter.

In accordance with a further important aspect of the present invention impedance testing facilities indicated generally at 100 are included in the head box 50 so that after the electrodes 56 have been attached to the patient's head, the impedance of each electrode may be sequentially tested to be sure that a good, low impedance connection has been made to the scalp of the patient.

Furthermore, an impedance display unit 102 is also included in the head box 50 so that the operator can determine the approximate value of the impedance of each electrode without returning to the console.

The impedance test facilities 100 include a forty-position switch which may be manually adjusted to select any one of the thirty-six patient electrodes 56 on an individual basis. However, since the impedance test is not conducted on a multiplex basis, the impedance test facilities 100 provide a control signal over the conductor 104 which changes the shift register in the control logic 88 so that it will accept parallel data, supplied over the conductors 106 from the facilities 100, corresponding to the address of any one of the electrodes 56. The control logic 88 accepts the parallel data on the conductors 106 and selects one of the switches 84 corresponding to the setting of the impedance test switch so that a particular one of the electrodes is applied to the G plus input of the amplifier 58. At the same time the control logic 88 includes facilities responsive to the control signal on the conductor 104 for connecting all of the other patient electrodes together and to the G minus input of the amplifier 58. At the same time the shift register in the control logic 88 is rendered unresponsive to the address data on the address input 90.

The impedance test facilities 100 in the head box 50 also include an a.c. generator (not shown) which is connected through the resistor 108 to the G plus conductor when an impedance test is being made. Accordingly, an a.c. voltage is impressed across the series combination of the selected electrode whose impedance is being measured in series with all of the other electrodes connected in parallel to the other input of the amplifier 58. A signal is thus impressed upon the differential input of the amplifier 58 which is proportional to the impedance of the selected electrode referenced to all of the other electrodes in parallel. This signal is amplified through the amplifier 58 and is coupled through an isolating transformer 110 in the output of the amplifier 58 to the impedance display 102, the display 102 being operated at system ground rather than at the isolated ground at which the first amplifier is operated. The impedance test facilities 100 also operate to supply a control signal over the conductor 112 and through isolator 114 to control the impedance display 102 so that this display is only operative when an impedance test is being made by the impedance test facilities 100.

During normal operation of the EEG system when the amplifier 58 is successively measuring different electrode pair signal voltages, the output of the amplifier 58 is reversed in polarity by means of the polarity reversing switches 116, a similar set of polarity reversing switches 118 being employed in the feedback path of the amplifier 58. The switches 116 and 118 are controlled over the MOD conductor 120 from the main console, the conductor 120 being connected through the isolator 122 to the switches 116 and 118. During an impedance test it is necessary to remove the modulation of the output signal of the amplifier 58 effected by the switches 116. Accordingly, the MOD conductor 120 is supplied to the impedance display 102 so that a signal proportional only to the amplitude of the output of the amplifier 58 is provided. This output signal is then supplied to a series of comparators which are biased to different reference levels and actuate individual indicator lamps in the display 102 so that a number of lamps are lit proportional to the impedance of the selected electrode, as will be described in more detail hereinafter.

In accordance with a further important aspect of the present invention, a calibration arrangement is provided for calibrating the common signal path of the EEG system by supplying a d.c. calibration signal to the isolated input of the amplifier 58. To this end a d.c. calibration voltage is developed by the source 124 in the main console and is supplied to a master control panel 126 at which a suitable level of d.c. calibration signal is selected by means of a multi-position switch. The d.c. calibration signal thus selected is supplied over the conductor 128 of the cable 52 to the head box 50 wherein it is applied to calibration amplifier and switching arrangement 130. In order to couple the d.c. calibration signal to the input of the amplifier 58 an isolating transformer 132 is employed and the amplified d.c. calibration signal is supplied through the polarity reversing switches 134 to the primary of the transformer 132, a feedback signal being supplied through the polarity reversing switches 136 to the input of the calibration amplifier 130. The output winding of the transformer 132 is connected to the polarity reversing switches 138 which are operated in synchronism with the switches 134 and 136 so that a d.c. signal proportional to the original level of d.c. calibration established at the master control panel 126 is supplied through the symmetrical resistors 140 and 142 to a small resistor 144 which is connected to the first one of the switches 84 corresponding to a zero input on the address line 90.

Since all of the equipment associated with the amplifier 58 must also be operated at isolated ground, a clock signal derived from the clock control 146 in the main console is supplied over the #1 conductor 148 and through the cable 52 and through an isolating transformer 150 to an isolated power supply 152. The isloated power supply 152 provides the various d.c. voltages required for all of the equipment which is operated within the isolated section 154 in the head box 50. In addition, the #1 clock signal on the conductor 148, which is coupled through the power supply 152, is supplied over the conductors 156 to control the polarity reversing switches 138 for the calibration signal.

During calibration of the common signal path, it is necessary to select the cailbration signal which is developed across the resistor 144. More particularly, a calibrate mode signal is developed at the master control panel 126 when the operator desires to perform a calibration operation. This calibrate mode signal is supplied over the conductor 158 to an isolator 113 in the head box 50. The address shifter 160 is employed during normal operation of the EEG system to shift the data supplied thereto into serial form which is then supplied over the conductor 90 to the control logic 88 and is shifted into the shift register of control logic 88 under the control of the fast clock pulses on the conductor 92. However, when the control logic 88 receives a calibrate mode signal from the isolator 113 it disregards the data inputs normally supplied thereto and loads a string of all zeros in the address register in the head box 50. When the first one of the G1 switches 84 is set to zero it connects the calibration voltage developed across the resistor 114 to the plus input of the amplifier 58 while the minus input thereof is connected to isolated ground. The common signal path described above may then be calibrated by applying various levels of d.c. calibration voltage to the input of the amplifier 58 under the control of the selector switch on the master control panel 126.

In accordance with a further important aspect of the present invention facilities are provided for checking the imbalance between each of the selected electrode pair combinations prior to the making of a run. Considered generally, this procedure consists in supplying an a.c. imbalance signal to the isolated section 154 of the head box 50 through the same isolating transformer 132 which is employed to connect the calibration signal to the input of the first amplifier 58. More particularly, an imbalance oscillator 62 is provided in the main console which may be selectively connected to the conductor 128 in place of the calibration signal by means of an imbalance push botton on the master control panel 126. The a.c. imbalance signal is thus supplied over the conductor 128 to the calibration amplifier 130 wherein it is amplified and supplied through the isolating transformer 132 to the secondary winding thereof. A set of polarity reversing switches 164 are connected in parallel with the switches 138 to the secondary winding of the transformer 132 and are controlled by the signals on the conductors 156 so that an a.c. imbalance signal is supplied over the conductor 166 and through individual isolating resistors 168 to the input filter side of each patient electrode 56. Accordingly, when the imbalance push button is actuated on the master control panel 126 an a.c. imbalance signal is supplied through the isolating resistors 168 to each selected electrode pair during each successive channel period in each twenty-channel frame. If the impedance of the two electrodes in a given pair are approximately equal balanced voltages will be applied to the two inputs of the amplifier 58 so that no noticeable output signal is produced on the trace corresponding to that channel. However, if one of the electrodes does not have good contact to the patient's scalp its impedance will be relatively high compared to the other electrode of the selected pair so that there is an imbalance in the signals applied to the amplifier 58 which is amplified in the common signal path and produces a deflection in the corresponding channel at the frequency of the a.c. imbalance signal. Since the selected electrode pairs are sequentially applied to the input of the amplifier 58 during each twenty-channel frame, all of the selected electrode pairs may be tested for imbalance by simply depressing the imbalance push button on the master control 126 and noticing whether or not any of the twenty channels are producing a large a.c. imbalance signal component.

While the above-described imbalance test is important to make, this imbalance signal, of course, interferes with the brain wave signals normally being supplied to the input of the amplifier 58. Accordingly, it would be desirable to provide an arrangement for sequentially testing each of the electrodes while the EEG traces are being made. Such a system is shown, for example, in Lencioni U.S. Pat. No. 3,859,988 wherein separate signal paths are employed for each selected electrode pair.

In accordance with a further aspect of the present invention, an arrangement is provided for sequentially testing all of the patient electrodes during the taking of an EEG while cooperating with the above-described facilities for sequentially connecting selected electrode pairs to the common signal path. More particularly, an open lead sequence generator 170 is provided within the isolated section 154 in the head box 50 and sequentially supplies a short burst of low frequency a.c. voltage to the input filter side of each of the patient electrodes 56 through the individual isolating resistors 172. If the connection of each patient electrode to the patient's scalp is properly made, a relatively low impedance exists between that electrode and the other patient electrodes and isolated ground. Under these conditions the voltage divider action between the isolating resistor 172 and the electrode impedance is such that an extremely small level of sequence generator signal is applied to the input of the amplifier 58. However, if any one of the patient electrodes 56 becomes disconnected from the patient's scalp or does not have a low impedance connection to the scalp, a relatively high impedance exists between that electrode and isolated ground. Accordingly, a large amplitude burst of low frequency signal is then applied to the input of the amplifier 58 and is visible on the response recorded by energization of galvanometer type pen motor 80 due to the change in the voltage divider action between the isolating resistor 172 and the electrode impedance.

As discussed generally heretofore, the signal voltage developed between any selected pair of patient electrodes 56 may comprise a relatively large d.c. component on which is superimposed a very low amplitude brain wave signal. This large d.c. component may arise from various sources such as chemical reaction with the skin of the patient, or the like. Furthermore, this d.c. component may slowly vary over a period of time with conditions of the patient. In addition, the d.c. component for one selected pair of electrodes may be of the opposite polarity from the d.c. component for the next selected pair of electrodes in the next channel. On the other hand, the d.c. components in the respective channels must be removed at some point in the common signal path since otherwise they would cause overloading of the succeeding amplifiers and drive the pens of each precording channel off scale.

In accordance with an important aspect of the present invention, the d.c. component of the respective electrode pair signal voltages is preserved through the first amplifier 58 and is coupled through the isolating transformer 110 so that the secondary winding of the transformer 110 includes all of the original components of each electrode pair signal voltage. However, the gain of the first amplifier 58 is made relatively small so that this amplifier will not overload when an electrode pair signal voltage having a large d.c. component is applied to the input of this amplifier. Preferably, the amplifier 58 and the isolating transformer 110 have a combined gain of seven, the remaining relatively large gain, or approximately thirty thousand, being accomplished in the succeeding amplifiers 60 and 60 which are operated at system ground. Also, in order to preserve the d.c. component of each electrode pair signal voltage during an entire channel period while preventing the output of the amplifier 58 from slewing into saturation in an attempt to maintain the output of the amplifier stable, it is necessary to switch the polarity of the output of the amplifier 58 and the rebalancing feedback signal by means of the switches 116 and 118, as will be described in more detail hereinafter.

The relatively low amplitude output signal derived from the secondary of the isolating transformer 110 is supplied over the cabled shielded pair portion 174 of the cable 52 to the input of the second amplifier 60. In the second amplifier 60, a base line suppression arrangement is employed which is effective at least partially to remove the d.c. components of the respective electrode signal pair voltages applied during each channel period. More particularly, the modulated signal which is transmitted over the cable 52 is coupled through the resistor 176 to the minus input of the second amplifier 60. This signal is also applied through a voltage divider comprising the resistors 178 and 182 to system ground and the voltage appearing across the resistor 182 is connected through a series time constant resistor 180 to the plus input of the amplifier 60. A series of time constant capacitors 184 are provided one for each of the twenty channel periods, these capacitors being connected through sequentially operated switches 186 to the plus input of the amplifier 60 during each channel period. During any given channel period, if a d.c. signal is applied to both inputs of the differential amplifier 60 it will not appear in the output thereof. This is because the feedback resistor 188 which is connected between the output of the amplifier 60 and the minus input thereof is chosen so that the ratio of the resistor 188 to the resistor 176 is the same as the ratio of the resistor 178 to the resistor 180. However, an a.c. signal is applied directly to the minus imput of the amplifier 60 but is filtered out by the low frequency filter formed by the resistor 182 and one of the cpacitors 184 so that a differential a.c. signal is applied to the input of the amplifier 60 and hence appears in amplified form at the output thereof.

With this arrangement, when no capacitor 184 is connected to the plus input of the amplifier 60, the output of this amplifier is zero. Accordingly, during alternate channel period frames, when the switches 186 are disabled, neither d.c. nor a.c. components of the electrode pair signal voltages are passed by the amplifier 60. This disabling of the switches 186 on alternate frames is required because of the fourth-channel component of the MOD signal on the conductor 120, as will be described in more detail hereinafter.

Each of the capacitors 184 becomes charged to the level of the d.c. component of the electrode pair signal voltage during the corresponding channel period. Accordingly, the d.c. component, or baseline, of each electrode pair signal voltage is suppressed and does not appear in the output of the amplifier 60. However, the a.c. brain wave signal is amplified at high gain (up to 150) in the amplifier 60. It is pointed out that a single time constant capacitor cannot be used for all channels because each channel will have a different d.c. component.

In order to change the gain of the amplifier 60, a series of switches 190 are provided to selectively connect the feedback resistor 188 to various points on a voltage divider network comprising the resistors 192, 194 and 196 which is connected between the output of the amplifier 60 and ground. The switches 190 may be selectively actuated from the master control panel 126 so as to select a desired amount of gain through the amplifier 60.

In accordance with a further aspect of the invention, a series of switches 198 are also employed to vary the feed forward or open loop gain of the amplifier 60, the switches 188 also being controlled from the master control panel 126. Accordingly, as the closed loop gain is varied by actuation of the switches 190, the open loop gain is also varied by means of the switches 198 so that the band width and output impedance of the amplifier 60 remain essentially constant as the gain of this amplifier is varied. With this arrangement, the gain of the amplifier 60 may be varied from approximately a factor of two to a factor of 150 while maintaining the band width and output impedance of this amplifier essentially constant. In this connection it will be understood that each of the amplifiers 60 and 62 must have extremely wide band width to accommodate the relatively high frequency components of the signal voltages which are produced when switching from one channel to another with different d.c. components of large amplitude in the various channels.

The output of the amplifier 60 is supplied to the input of the amplifier 62. In general, the amplifier 62 is similar to the amplifier 60 and corresponding components have been given the suffix "$\mp$a". However, in the amplifier 62, different values of series time constant resistor may be connected to the plus input of the amplifier so as to provide a variable loss pass filter cutoff at the plus input of the amplifier 62. More particularly, the time constant resistors 200 and 202 may be selected by means of the switches 204 from the master control panel 126. In addition, these switches may be controlled on an individual channel basis, as will be described in more detail hereinafter.

The output of the third amplifier 62 is then supplied to a 30-Hertz low pass filter by means of which the high frequency components above thirty cycles may be selectively removed from any electrode pair signal voltage on an individual channel basis. More particularly, the filter 64 comprises a series resistor 210 which is connected to the plus input of a buffer amplifier 212 to the minus input of which is applied a feedback signal from the output of the amplifier 212. A series of capacitors 214, one for each channel period, may be selectively connected to the plus input of the amplifier 212 by means of the switches 216. The switches 216 are controlled on an individual channel basis by means of a 30-Hertz control signal which is applied to the terminal 218 from the data portion of the console, as will be described in more detail hereinafter.

Accordingly, by means of the filter 64 any particular electrode pair signal voltage may have the high frequency components thereof attenuated so that undesired interference from muscle artifact signals or the like, may be selectively removed from any particular channel, while employing only the single, common 30-Hz filter 64.

As discussed generally heretofore, the output of the first amplifier 58 in the head box 50 is reversed in polarity under the control of a modulation signal impressed upon the conductor 120 and supplied to the polarity reversing switches 116 and 118. This MOD signal is effective to reverse the output of the amplifier 58 in polarity every four channel periods.

Since in the illustrated embodiment there are twenty channels, it will be evident that during successive time position frames the polarity of each channel period is reversed, as will be described in more detail hereinafter. However, this fourth channel modulation signal must be removed before the demultiplexer 74. To this end, the output of the 30-Hertz filter 64 is supplied to the input of a demodulation amplifier 66 through the polarity reversing switches 68. The switches 68 are controlled by signals from the clock control 146 which are effective to remove the four-channel MOD signal. At the same time, these signals are effective to reverse the output of the amplifier 66 in polarity every other channel period. This modulation of the composite signal in the common signal path is provided so that the polarity of the output signals developed on adjacent ones of the individual channel sampling capacitors 76 are of opposite polarity. This is done so that the individual galvanometer pen motors 80 for adjacent channels may be arranged so that their fields are physically in opposite direction to eliminate long flux paths between adjacent galvanometer field structures. With such an arrangement, the input signals for adjacent channels must be oppositely polarized signals, otherwise the recording pens for all of the galvanometers will not be deflected in the same direction for a positive going input signal. The amplifier 66 is provided with an effective gain of two and the gain of the amplifier 66 is not adjustable in the manner of the amplifiers 60 and 62.

The output of the demodulation amplifier 66 is supplied to a voltage limiter 72 which functions to limit the maximum amplitude of voltage which is transmitted during any five channel period so that this voltage does not exceed the limits of the power amplifiers in the individual recording channel 78 or the associated pen motors 80. It will be noted that by limiting all signal voltages in the common signal path, only a single voltage limiter is required for all of the twenty individual recording channels.

The output of the voltage limiter 72 is supplied to a fifth amplifier 70 which provides an additional baseline suppression but has a fixed gain of one. Since the input circuit of the amplifier 70 is similar to that of the amplifier 60, the same reference numerals with the suffix "b" have been used. The additional baseline suppression provided by the amplifier 70 is needed to remove any d.c. components which may be amplified in the amplifier 62, as will be described in more detail hereinafter.

The output of the amplifier 70 is supplied through one or more of a series of series connected resistors 230, 232 and 234 to the input of the demultiplexer 74. The demultiplexer 74 includes a series of twenty switches which are controlled from the scan lines generated in the clock control 146 so that the resistor 234 is sequentially connected to different ones of the channel sampling capacitors 76 during the twenty successive channel periods in each time position frame.

In accordance with an important aspect of the invention, the series resistors 230, 232 and 234 which form a part of the common signal path of the equipment, form a high frequency filter with each of the individual channel capacitors 76 so as to remove high frequency components from the individual channels at the same time that the signal voltage for that channel is being demultiplexed. With such an arrangement, the cut-off frequency of this filter may be much lower than if filtering is done at earlier stages in the common signal path where the high frequency components of the switched electrode pair signals would have to be preserved. The resistors 230, 232 and 234 may be selectively switched into the circuit to vary the common high frequency filtering characteristic provided for all channels. More particularly, the switches 238 may be selectively controlled by means of control signals supplied from the master control panel 126, as will be described in more detail hereinafter.

When a sampling rate of 700 samples/sec./channel is employed, an error is introduced due to the fact that the signal voltage may change between samples. For example, a full scale 70-Hz signal would cause a maximum change between samples which, without filtering after the demultiplexer, would cause a 4 mm. step in the recording trace. However, each galvanometer 80 has a two-pole filter effect starting at 70 Hz which at a sampling frequency of 700 Hz reduces the signal by 40 db or a factor of 100. The deflection for a full-scale 70-Hz signal will then be reduced to 0.04 mm. which is not objectionable. Accordingly, no post demultiplex filtering for the sampling frequency other than that provided by the galvanometer 80, is required. However, if a 60-Hz component needs to be attenuated, a 60-Hz notch filter may be employed in each channel. As described above, the common 30-Hz filter 64 provides selective attenuation for signals above 30 Hz, as desired.

As discussed generally heretofore, the address shifter 160 receives data on the input lines 250 and converts each thirteen bit address signal into serial bit form which is then supplied over the address line 90 to the control logic 88 in the head box 50. The clock control 146 controls the address shifter over the lines EB and $\overline{EB}$ so that the thirteen-bit address is serially supplied to the control logic 88 at the start of each channel period, as will be described in more detail hereinafter.

In accordance with an important aspect of the present invention, a number of selected patterns of electrode pairs, which are commonly referred to as montages, are stored in an EAROM 252. The EAROM 252 is electronically addressable and reprogrammable so that the electrode pairs which go to make up any particular montage may be changed by the operator of the EEG system. To this end, a microprocessor 254 is provided which is addressable through a microprocessor interface board 256 from a keyboard 258. The address bus of the microprocessor 254 is connected to one set of inputs of an AND/OR selector 260 the output of which is supplied to the read write line and address lines of the EAROM 252. The other input lines of the AND/OR selector 260 are provided from the clock control 146 and the higher order bit lines are generated at the master control panel 126 and are supplied to a preset selector 264.

In one mode of operation of the EEG system of the present invention, any one of the eleven montages stored in the EAROM 252 may be selected by means of the control signal supplied to the preset selector 264 from the master control board 126, the AND/OR selector 260 being arranged in this mode of operation to supply this information to the address lines of the EAROM 252. However, in accordance with an important phase of the present invention, the microprocessor 254 may be employed to change the selection of electrode pairs of any particular montage stored in the EAROM 252. To this end, the higher order bits on the address bus of the microprocessor 254 are supplied to the control input 266 of the AND/OR selector 260 so that addressing the read/write control of the EAROM is shifted to the microprocessor 254. The operator may then enter a desired modification of the electrode pairs making up any particular montage through the keyboard 258 and the interface board 256. The modified montages which are then stored in the EAROM 252 semi-permanently and may thereafter be selected by the operator through the preset selector 264.

The EAROM 252 is employed only to store selected montages of electrode pairs. Accordingly, it is necessary to provide control signals which will control the time constant switches 186, 186a and 186b, the feedback gain control switches 190, 190a, the forward gain control switches 198 and 198a and the time constant resistor switches 204, for a particular EEG run. Normally, the above-identified switches are controlled by manually adjustable controls on the master control panel 126. However, in accordance with an important aspect of the present invention, control of these switches may be shifted to the microprocessor 254 which is then employed to address an override RAM 268, through the keyboard 258 and interface 256, so that the operator may change the master control setting on an individual channel basis in the event that he decides a particular channel requires a different gain setting or time constant than the master control settings. More particularly, an AND/OR selector 270 is provided for shifting control of the read/write and address lines of the override RAM 268 from the normal clock scan cycle, provided by the clock control 146 on the conductors 236, to the address bus of the microprocessor 254, the higher order address lines of the address bus being employed to control the AND/OR selector 270. The override RAM 268 also includes additional addresses for electrode selection which enables the operator to temporarily alter the electrode selection of a particular montage which is normally selected from the EAROM 252, such override being accomplished through the keyboard 258 and interface 256. These override electrode selector addresses are supplied over the output conductors 272 in parallel with the output conductors from the EAROM on the conductors 274 to the address data input 250 of the address shifter 160. In addition, these parallel outputs are supplied over the conductors 276 to one of the input ports of the I/O PORTS board 278 which is interconnected with the microprocessor 254 through the data bus and address buses thereof, as will be readily understood by those skilled in the art. In addition, the output control lines 280 of the override RAM 268 which are employed to control the feedback and feed forward switches in the second amplifier 60 are supplied to a second input port 282 of the input port board 278. Also, the output conductors 284 of the override RAM 268 which are employed to control the time constant switches 204 in the third amplifier 62, are supplied to a third input port 286.

Since the EEG system of the present invention employs a common signal path for all channels and the individual electrode pairs which are examined during each channel period are selected by address data on the lines 250, there are no mechanical switches the setting of which can inform the operator of the particular electrode pairs which are being employed for a particular EEG run. In accordance with an important aspect of the present invention, two types of displays are employed to inform the operator of the particular montage of electrode pairs which is being used for a particular EEG run. More particularly, a channel display 290 is provided which consists of a series of seven-segment display units which provide the operator with numerical display information concerning any particular one of the twenty channels. In addition, a head display indicated generally at 292 is provided which consists of an outline of a human head with indicator lamps corresponding to each of the twenty-four patient electrodes which may be selected to establish a desired average reference level, as will be described in more detail hereinafter.

The channel display 290 is controlled from the microprocessor 254 through the interface 256 and the digit drivers 294 which control energization of each seven-segment unit in the channel display 290. In order to provide an indication that an override selection has been made in connection with any particular channel, an override display indicated generally at 296 is provided, this override display being associated with the keyboard 258, as will be described in more detail hereinafter. A display RAM 298 is provided which may be selectively addressed through the AND/OR selector 300 from either the address bus of the microprocessor 254 or from the output of the interface 256 over the conductors 302. The higher order address lines of the address bus of the microprocessor 254 are employed to control the AND/OR selector 200 over the leads 304. The display RAM 298 functions to control selection of individual LED's in the head display 292 and to control the override display 296 through the cathode drivers 306, which drive the cathodes of the respective LED's in each of the displays 292 and 296. The anodes of these displays are driven from the digit drivers 294 over the conductor 308.

Considering first the channel display 290, shown in FIG. 3B, the first two seven-segment displays 310 and 312 are employed to digitally display to the operator the channel number of any one of the twenty channels selected on the keyboard 258. The next three seven-segment displays 314, 316 and 318 identify the electrode which is applied to Grid No. 1, i.e. the G plus conductor 434 which is connected to the plus input of the first amplifier 58. The reason three seven-segment displays are employed is to permit designation of the electrodes in either a digital system or the 10–20 International system of electrode designation which latter system requires three digits of an alpha numeric display, for example, FP2. The next three seven-segment displays 320, 322 and 324 are employed to display the designation of the electrode connected to the G minus input of the amplifier 58. The use of three seven-segment display devices for Grid No. 2 also permits the visual display of the designation AVG on these devices when an electrode average reference is applied to this input, as described in more detail hereinafter. The next two seven-segment displays 326 and 328 provide digital information of the time constant which has been selected by the operator, either on the master control panel 126 or through the keyboard 258 for the particular channel shown in units 310 and 312. The final two seven-segment displays 329 and 330 digitally display the sensitivity multiplier which is selected by the operator, for the channel shown by display units 310 and 312. The channel display 290 also includes an LED 332 which is energized whenever a 30-Hertz filter is selected by the operator, through the keyboard 258, for that particular channel. The decimal point indicators associated with the units 326 and 329 are used in a conventional manner to indicate the time constant or gain setting selected.

Referring now to FIG. 4, the keyboard 258 is shown therein as including an OVERRIDE ON button 341. As soon as the button 341 is depressed, the contents of the override RAM 268 or EAROM 252 will be displayed on the channel display 290. If nothing is stored in the RAM 268 the operator may proceed to override any of the settings for any one or more of the channels. To do this, the operator presses one of a series of twenty channel select keys 342 to select a particular channel for override. As soon as one of the keys 342 is pressed, the corresponding channel number is shown in display units 310 and 312.

A series of time constant keys 344 are provided on the keyboard 258 which permit the operator to select one of the resistors 200, 202 in the input of the third amplifier 62 so that a time constant of 5.0, 1.0, 0.3, 0.16 or 0.03 seconds can be selected. A key 346 is also provided which when depressed provides whatever time constant is then called for on the master control board 126. A series of keys 348 permit the operator to select the sensitivity multiplier to be used with a particular channel, the keys 348 providing gain multipliers of 20, 4, 2, 1, 0.5 and 0.25, respectively. A key 350 is provided which when depressed connects electrodes 17 and 18, commonly designated as the ear electrodes, to Grid 2, i.e. the G minus input of the amplifier 58. Also, a key 352 is provided which when depressed provides the average electrode output from the unit 94 in the head box 50 to be applied to Grid 2, i.e. the G minus conductor.

The keyboard 258 also includes a series of thirty-six electrode select keys 360, any one of which may be depressed by the operator to select a particular electrode which is to be applied to the G plus input of the amplifier 58 for that channel. In a similar manner, the next one of the buttons 360 which is depressed selects the other electrode to be included in the electrode pair connected to the input of the amplifier 58 for that channel. As each electrode is selected, its designation appears on the channel display 290. If it is desired to select electrodes 17 and 18, the ear electrodes, and connect these electrodes together to one of the inputs of the amplifier 58, the key 362 is depressed. If it is desired to provide a 30 Hz filter characteristic for that channel the operator depresses the 30 Hz key 364.

If it is desired to connect the electrode average to one input of the amplifier 58 the average select button 370 may be depressed. After the operator has selected all items for a particular channel, he presses the lock button 374 which stores the selected data in the RAM 268 and renders it nonresponsive to further input from the keyboard until another channel select button 342 is depressed. In order to remind the operator that no further changes can be made for that particular channel, all of the units 310-330 in the channel display are controlled to show the number "8" when the lock button 374 is depressed. If there is data stored in the RAM 268 when the ON button 341 is depressed, the operator may clear the RAM 268 by depressing the clear button 378.

In accordance with an important aspect of the invention, the electrode select buttons 360 may also be used to select a group of electrodes within the first twenty-three patient electrodes 56 which are to be designated as the averaging electrodes. To accomplish this, an average on/off button 366 is depressed which initially places all of the first twenty-three electrodes in the average. The operator may then delete any one or more of the first twenty-three electrodes from this average by depressing the corresponding ones of the keys 360. After all of the desired electrodes have been deleted from the average, the average lock button 368 is depressed which then prevents subsequent depression of any of the keys 360 from affecting the average. This selection of electrodes to be included in the average is usually done before any override functions are accomplished in any particular channel. Accordingly, after the average has been designated, as described above, if the operator desires to use the average as one of the inputs to the amplifier 58, he depresses the average select key 370 which functions to provide the output of the averaging latches and switches 94 to the particular grid which is being programmed. If the operator wishes to change the number of electrodes included in the average he may depress the RE-ENTER button 372 which re-opens the keys 360 for further average electrode selection. The keys 350 and 352 are active for all channels and are included for convenience so that the operator does not have to push the average select button 370 or the A1 plus A2 select button 362 for each channel. When the key 370 is depressed, either the display devices 314, 316, 318 or the display devices 320, 322, 324 are controlled to display the designation AVG, depending upon whether the key 370 is depressed to apply the average reference to Grid No. 1 or Grid No. 2. When the key 352 is depressed the display devices 320, 322, 324 are controlled to display AVG for each channel. When the key 350 is depressed the display devices 320, 322 and 324 are controlled to display A/A, thereby to inform the operator that the ear electrodes are being employed as an average reference for Grid No. 2.

Figure 5:
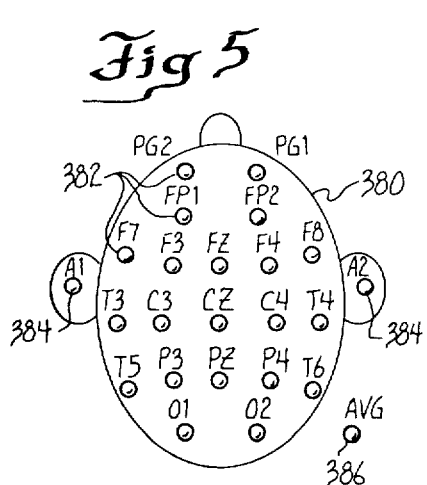
FIG. 5 is a pictorial diagram of the head display of the system of FIGS. 1, 2 and 3.

The head display 292, shown in FIG. 5, comprises an indicator panel which bears the outline of a human head 380, as viewed from the top, and includes a number of LED indicator lamps 382 which are spatially distributed with respect to the outline 380 so that they bear the same physical relationship to the outline 380 as the actual electrodes attached to a patient's head. The LED's also include a pair of LED's 384 corresponding to the ear electrodes. In addition, an LED 386 is provided outside the head outline 380 and is lit whenever the averaging electrodes are selected for a particular channel. When the operator initially selects the electrodes to be included in successive electrode pairs for the twenty channels, the particular ones of the lamps 382, 384 and 386 are lit to visually display to the operator the particular electrodes he has selected. Thus, if the operator is programming channel 1 and he selects the F3 electrode to be applied to the G plus input of the amplifier 58, the appropriate one of the lamps 382 within the outline 380 will be lit. If he also selects the average to be applied to G minus, the lamp 386 will be lit. In addition, when the operator has made all the desired changes for a particular channel and has depressed the lock button 374 all of the indicator lamps 382 which are included in the average, are simultaneously illuminated so that the operator can immediately determine by visual inspection what electrodes are included in the average.

The override display 296 comprises the decimal point indicator lamp portions of the display units 314 and 320 and a series of LED's 343 which are included in the keyboard 258 above each one of the twenty channel select buttons 342. Whenever an override is made and the electrode assigned to a particular grid for a particular channel is changed by the operator, as described above, the decimal point indicator of the corresponding unit 314 or 320 is lit to remind the operator that he has overriden the program stored in the EAROM 252. At the same time, the LED 343 which is over the corresponding channel button 342 is lit to provide a further indication to the operator that he has overriden a previously programmed item. The LED 343 is also lit whenever the operator changes the time constant or gain setting for a particular channel by depressing one of the keys 344, 346 or 348.

In order to store a designation of the particular patient electrodes which are to make up the average group of electrodes for any particular run, an averaging RAM 259 is provided. An average counter 261, which is controlled over the EB line from the clock control 146, produces control pulses on the output conductor 263 thereof until it has counted twenty-three successive channel periods at which time the counter 261 is reset through the encoding logic 265 the output of which supplied to the reset terminal of the counter 261. The logic 265 also provides a reset signal on the conductor 536 which is supplied to the head box 50 to control the synchronous operation of a similar counter in the head box 50 as will be described in more detail hereinafter. The output of the counter 261 is supplied as one input to an AND/OR selector 267 the other input of which comprises the address bus of the microprocessor 254, the higher order lines of this address also being employed to control the selector 267. The microprocessor data bus is connected to the input of the averaging RAM 259 and the output of this RAM which is supplied to the address shifter 160, comprises a single bit of data during each of the twenty-three successive channel periods. These data bits are employed in the head box to control selection of the particular ones of the twenty-three patient electrodes which are to be included in the averaging group. Accordingly, when the averaging button 366 on the keyboard 258 is depressed the 259 may be addressed through the AND/OR selector 267 over the microprocessor address lines corresponding to the particular ones of the electrode select buttons 360 which have been selected by the operator to be in the averaging group. This information, once stored in the 259, is repeatedly read out, during twenty-three sucessive channel periods, to the address shifter 160 so as to permit selection of the designated electrodes within the head box 50.

Figure 6:
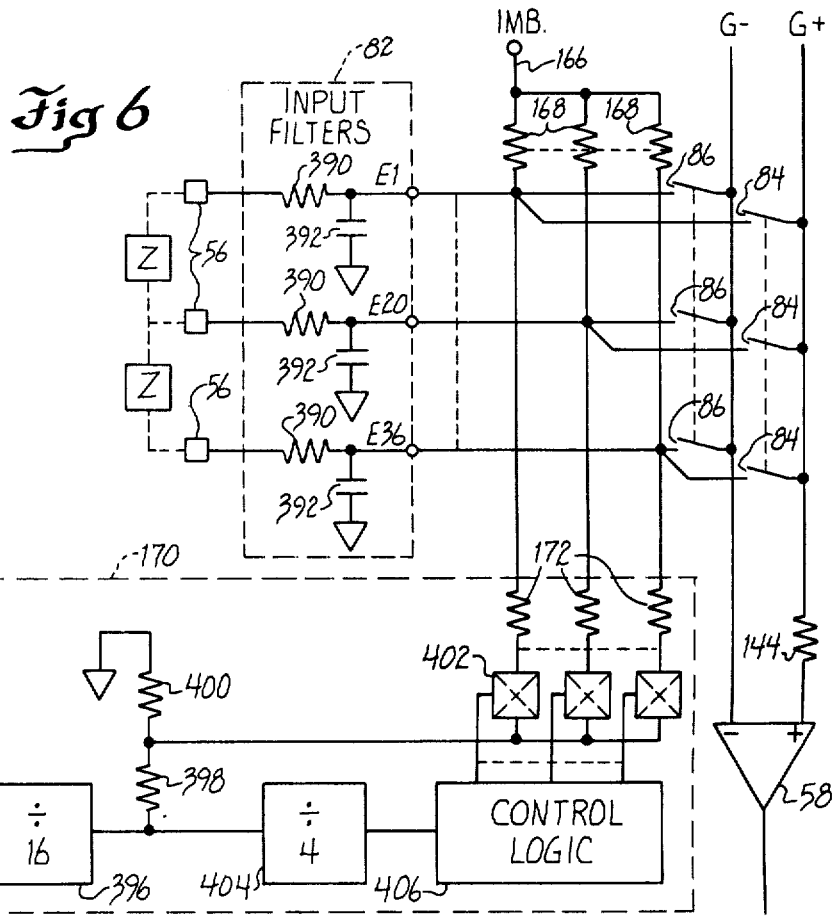
FIG. 6 is a schematic diagram of the input filter portion of the system of FIGS. 1, 2 and 3.

Referring now to FIG. 6, the details of the input filters 82 and the opening lead sequencing circuit 170 are shown therein. More particularly, each of the input filters comprises a series resistor 390 and a shunt capacitor 392, these elements each comprising a low-pass filter for each of the patient electrodes 56. Preferably, the resistor 390 has a value of 5,000 ohms and the capacitor 392 a value of 0.02 microfarads. These input filters are connected to the isolated ground of the isolated section 154 in the head box 50 which is also connected to the common terminal of the first amplifier 58 so that pickup due to extraneous noise voltage, and the like, are minimized. When an electrode has a very high impedance in the order of 50,000 ohms the input filter 82 has a high frequency breakpoint of approximately 150 Hz. As the electrode impedance approaches zero, the break point of the input filter 82 approaches 1.6 kHz due to the series resistor 390. The capacitors 392 also lower the Johnson noise of the filter resistors and other input resistors associated with each input to the amplifier 58.

The sequencing generator and switching 170 comprises a 48 Hz oscillator 394 which is continuously running. The output of the oscillator 394 is supplied to a divide by sixteen divider 396 the output of which is supplied to a voltage divider comprising the resistors 398 and 400.

Accordingly, a 3 Hz signal of relatively low amplitude is applied to one input of a series of semi-conductor analog switches 402 which are provided for each of the patient electrodes 56. The switches 402 are controlled through a divide by four stage 404 by means of control logic 406 which functions to sequentially connect each of the switches 402 to the corresponding isolating resistor 172 for a burst of four cycles of the 3 Hz signal developed across the resistor 400. Accordingly, a four-cycle burst of 3 Hz signal is sequentially applied to each of the patient electrodes 56. If a proper connection has been made between a patient electrode and the patient's scalp a relatively low impedance will exist between that electrode and the other patient electrodes.

The resistors 172 may have a value of 10 megohms and a properly connected patient electrode may have an impedance of 10,000 ohms nominally. Accordingly, under normal conditions an insignificant amount of the 3 Hz signal appears at each of the patient's electrodes so that when a pair of electrodes 56 are selected and applied to the input of the amplifier 58 an insufficient amount of the 3 Hz signal is supplied to be detected in one of the recording channels 80. However, if a patient electrode 56 becomes disconnected from the patient's head, it will have substantially infinite impedance so that a substantial amplitude of 3 Hz signal is supplied through one of the G1 switches 84 or the G2 switches 86 to the input of the amplifier 58 and hence may be detected in the corresponding recording channel. It will be noted that this sequential open lead test is performed without in any way interfering with the selection of different electrode pair signal voltages during successive channel periods through selective activation of the switches 84 and 86. It will also be noted that the open lead sequencing test does not interfere with the imbalance test in which an a.c. imbalance signal is developed on the conductor 166 and is impressed through the isolating resistors 168 to the switch side of each of the input filters 82. The resistors 168 also preferably have a value of ten megohms so that the imbalance a.c. signal does not interfere with the open lead sequencing test. In this connection it will be understood that only three patient electrodes 56 are shown in FIG. 6 whereas the complete system may employ up to thirty-six patient electrodes.

Referring now to FIGS. 7 to 14, inclusive, wherein the circuit details of elements 84, 86, 88, 94, 100 and 102 described heretofore in connection with FIG. 1 are shown, the serial address data which is supplied to the head box 50 over the conductor 90 is connected to an optoisolator 410 and the fast-shift clock pulses applied to the conductor 92 are impressed upon an optoisolator 412. Both of these inputs are connected to the fast shift ground 414 so that the only inputs to the data registering circuits in the head box 50 are through the ground 414. The optoisolators 410 and 412 isolate the lines 90 and 92, respectively, from the system ground of the console.

The output of the optoisolator 410 is supplied to a serial-in-to-parallel-out or parallel-in-to-parallel-out shift register which employs the 4035 type IC's 416, 418 and 420 and a type 4013 IC 422. In the normal operating mode, this shift register is operated in the serial-in-to-parallel-out mode and the fast shift clock pulses on the line 92 are supplied through the isolator 412 to the clock inputs of the IC's 416, 418, 420 and 422. These fast shift clock pulses have a repetition rate much higher than the 700 Hz sampling rate which establishes the twenty-channel periods. Accordingly, shortly after the start of each channel period the serial address data on the line 90 is shifted into this thirteen-bit shift register. The shift register 416–422 controls the G1 switches 84 which consist of a series of five 4051 type IC's 424, 426, 428, 430 and 432. Each of the 4051s comprises a series of eight semiconductor analog switches so that any one of the thirty-six patient electrodes may be connected to the G plus conductor 434 in accordance with the first six bits of address data registered in the IC 416 and the first half of the IC 418. The next six bits of data, which are registered in the last half of the IC 418 and the IC 420 are employed to control a series of five 4051 type IC's 436, 438, 440, 442 and 444. These 4051 type IC's in turn control a series of ten 4066 type IC's, identified as 446 to 464, inclusive, the 4066 switches functioning to connect any one of the thirty-six electrodes 56 to the G minus conductor 466 in accordance with the second six bits of data registered in the shift register. The thirteenth bit of data registered in the IC 422 is employed during selection of the electrodes making up the average electrode pattern, as will be described in more detail hereinafter.

The four analog switches in each forty switch bank which are not required to connect one of the thirty-six electrodes to the G plus or G minus conductors are employed for other auxiliary functions. As discussed generally heretofore, when the calibration mode line 158 is high the calibration inputs are to be selected for calibration purposes. To this end a D flip-flop 415 is connected between the output of the isolator 410 and the input of the first shift register stage 416. The calibration mode line 158 is connected to the reset lead of the flip-flop 415 and the fast shift clock pulse output of the isolator 412 is connected to the clock input of the flip-flop 415. When the line 158 is high the flip-flop is continuously reset to zero so that as successive bits appear in the address line 90 a string of zeroes is shifted into the shift register 416–422. When a zero is registered for the first one of the 4051 switches in the IC 424, the analog calibration mode signal on the conductor 144a is supplied through this switch to the G+ conductor 434 and hence to the G+ input of the amplifier 58. At the same time the first switch in the 4066 IC 446 is connected to isolated ground so that G− input of the amplifier 58 is connected to isolated ground. The calibration voltage across the resistor 144 is thus applied to the input of the amplifier 58 while all electrode voltages are excluded therefrom.

As discussed generally heretofore, the ear electrodes E17 and E18 may be selectively connected together and may be connected to either the conductor 434 or the conductor 466 in the same manner as any one of the thirty-six patient electrodes. To this end a pair of semiconductor analog switches 472 and 474 are controlled by the network 476 when the number 38 is stored in the first six bits of the shift register so that the electrodes E17 and E18 are connected together to the conductor 478. The conductor 478 is then connected to the G plus conductor through one of the semiconductor analog switches on the IC 432. When the number 38 is registered in the second six bits of data in the shift register, the E17 electrode is connected through one of the switches on the IC 464 to the G minus conductor and the E18 electrode is connected through a separate semiconductor analog switch 480 to the G minus conductor 466. The switch 480 is controlled by the corresponding switch on the IC 44 so that both the E17 and the E18 electrodes are connected together and to the G minus conductor.

As discussed generally heretofore, the group of electrodes selected as the averaging electrodes may also be selectively connected to either the G plus or the G minus conductor in the same manner as any one of the thirty-six patient electrodes. Accordingly, when the number thirty-nine is registered in the first six bits of data in the shift register, the averaging output conductor 96 is connected through one of the switches on the IC 432 to the G plus conductor. Similarly, when the number thirty-nine is registered in the second six bits of data in the shift register, the conductor 96 is connected through one of the switches on the IC 464 to the G minus conductor.

In the EEG system of the present invention the patient ground electrode 482 (E37) may be selectively connected to either the G plus or G minus conductors in the same manner as any one of the thirty-six patient electrodes. More particularly, when the number 40 is registered in the first six bits of data in the shift register, the patient ground electrode is connected through one of the switches in the IC 432 to the G plus conductor. When the number 40 is registered in the second six bits of data in the shift register the patient ground electrode 482 is connected to the G minus conductor through one of the switches on the IC 464.

In accordance with an important phase of the present invention, the patient ground electrode is connected to isolated ground through a current limiting device so that the maximum current which can be drawn through any of the patient electrodes is limited to ten microamperes. This is particularly important in the system of the present invention wherein any one of the semiconductor analog switches which are employed to connect the patient electrodes to the G plus and G minus conductors are controlled by control lines having relatively large voltages on them to control conduction of the associated semiconductor switch. If any of these semiconductor analog switches shorts the control line to one of the switch terminals, a large voltage can be applied directly through the shorted switch and the patient electrode to the patient's head. However, protection for all thirty-six electrodes is provided in accordance with the present invention by providing a single current limiter in series with the patient ground electrode. More particularly, a current limiter 486 is connected from the patient ground electrode terminal E37 through an analog switch 488 to isolated ground. The current limiter may be of the type IS-10 and limits the total current drawn through the device to ten microamperes. The switch 488 connects the current limiter 486 to isolated ground during normal operation of the EEG system. However, in accordance with a further aspect of the present invention, when an impedance test is to be made, the impedance of the patient ground electrode may also be measured. During this impedance test the switch 488 is opened, as will be described in more detail hereinafter. It should be noted that by connecting the patient ground electrode 482 to isolated ground through the current limiter 486, any stray pickup voltages on any of the electrodes including the patient ground electrode, with respect to system ground, are effectively isolated from the input of the amplifier 58. The isolated ground point in the isolated section 154 may have a capacitance to the housing and system ground portion of the equipment of approximately 400 picofarads. Accordingly, even though the current limiter 486 has an impedance of approximately 40,000 ohms, a relatively small common mode voltage is developed at the common terminal of the amplifier 58. However, the resistance of the current limiter 486 is in series with the isolated ground connection to the common terminal of the amplifier 58 so that a low pass filter effect is produced due to the shunt 400 picofarad stray capacitance to system ground, this filter being effective to remove all but the highest frequency signals picked up on the patient electrodes and the patient ground electrode 482.

Considering now the facilities provided for selecting the particular ones of the first twenty-three patient electrodes which are to be included in the averaging group and the connection of the averaged output to the averaging output conductor 96, a counter 490 is provided the output lines of which are employed to control, through logic which includes the OR-gates 492, 494, and 496, and the AND-gates 498, 500 and 502, a series of three eight-bit addressable latches 504, 506 and 508, each of these latches being type 4099 IC's. These addressable latches in turn control the 4066 type semiconductor analog switches 510–520 so that when any one of the addressable latches is set it closes a corresponding one of the 4066 switches so that the corresponding patient electrode is connected through one of the averaging resistors 522 to the averaging output conductor 96. The counter 490 is controlled from the EB line in the clock control 146, this signal being differentiated in the capacitor 524 so that a differentiated pulse is applied to the base of a transistor 526 in the emitter of which is connected the LED of an optoisolator 528. The optoisolator 528 isolates the clock line EB, which is at system ground, from the counter 490, the output of the optoisolator 528 being supplied through the squaring amplifier 530 and the inverter 532 to the input of the counter 490. The counter 490 is thus driven at channel rate and sequentially enables the addressable latches 504, 506 and 508.

As discussed generally heretofore, the thirteenth address bit in the register 422 is employed to set the enabled one of the addressable latches 504, 506 and 508 if the corresponding patient electrode is to be included in the average group. This means that the addressable latches can only be set one at a time during twenty-three successive channel periods in accordance with the value of the thirteenth bit in the address data supplied over the line 90 during these twenty-three successive channel periods. Thus, assuming that the counter 490 has an output of one, the first addressable latch in the IC 504 will be enabled and during this same channel period address data is supplied over the line 90. If the thirteenth bit of this address data is a one, the first addressable latch in the IC 504 is set so that the switch on the IC 510 is closed to connect the first electrode through its resistor 522 to the averaging output conductor 96. However, if the thirteenth bit of address data during this channel period is a zero the enabled latch will not be set and the first electrode will not be connected to the conductor 96. During the next channel period the second latch in the IC 504 is enabled and is either set or not depending upon the thirteenth data bit which is supplied over the conductor 534 to the D lines of all of the addressable latches 504, 506 and 508. In a similar manner the remaining ones of the twenty-three patient electrodes which may be included in the average are selectively connected to the conductor 96. After the addressable latches have been sequenced, a reset pulse is supplied over the conductor 536 from the anoding logic 265 and through the transistor 538 to an optoisolator 540. The output of the optoisolator 540 is supplied through the squaring amplifier 542 to the reset line of the counter 490 so that this counter is reset to zero after all of the addressable latches 504, 506 and 508 have been sequentially enabled. The group of patient electrodes which have thus been selected to include in the average are thus connected through the closed ones of the 4066 switches 510–520 and through the averaging resistors 522 to the conductor 96. The conductor 96 may then be selected in the manner described heretofore and be connected to either the G plus or G minus conductor during any particular channel period. Furthermore, it is possible to use the averaged output on the conductor 96 as one of the inputs to the amplifier 58 even though one of these same electrodes in the average group is connected to the other input of this amplifier since the averaging electrodes are isolated from one another through the resistors 522.

Considering now the facilities which are provided in accordance with the present invention to perform an impedance test on any one of the thirty-six patient electrodes or the patient electrode ground 482, it will be recalled from the preceding general description that the electrode whose impedance is to be tested is connected to the G plus conductor and all of the other patient electrodes are connected together and to the G minus conductor. The impedance test facilities include a forty-position rotary switch which is effective during the impedance test mode to supply parallel data on the output conductors 106 which designates any one of the thirty-seven electrodes to be tested. In addition, the facilities 100 include a normal-impedance mode switch which is effective in the normal mode of operation of the system to provide a negative voltage on the IMP+ conductor and a positive voltage on the IMP− conductor 492. When this switch is in the impedance test mode, the potential on the conductors 490 and 492 is reversed so that the potential on the conductor 490 is plus and the potential on the conductor 492 is minus.

As discussed generally heretofore it is necessary to adapt the shift register 416, 418 and 420 to accept the parallel data which is supplied over the conductors 106 during the impedance test operation. When the potential on the impedance plus conductor 490 is positive, this signal is applied through the inverter 494 and over the conductor 496 to the pin 7 terminals of the shift registers 416, 418 and 420 and adapts these registers to accept parallel data from the conductors 106 while preventing these registers from responding to serial data appearing on the address line 90. Accordingly, depending upon the setting of the forty-position rotary switch in the facilities 100, a particular one of the thirty-seven electrodes is connected through one of the 4051 switch 424–432 to the G plus conductor 434. When the normal-impedance mode switch in the facilities 100 is in the normal position the potential on the conductor 536 is minus so that the shift registers 416–422 are conditioned to received serial data over the address line 90 rather than parallel data over the conductors 106.

Considering now the manner in which the remaining ones of the patient electrodes, other than the selected electrode which is connected to the G plus conductor, are connected together and to the G minus conductor, the forty-position rotary switch in the facilities 100 is arranged to provide the same number for both the first six bits of information and the second six bits of information supplied to the shift registers 416, 418 and 420 over the conductors 106. Accordingly, during an impedance test operation the same electrode is selected in the bank of 4051 switches 436–444, which normally control connection of an electrode to the G minus conductor, and in the bank of 4051 switches 424–432 which connect an electrode to the G plus conductor, due to the fact that the same number is supplied by both the first six bits of data and the second six bits of data during an impedance test. However, in accordance with an important aspect of the present invention, the 4051 switches 436–444 are interconnected with the IMP+ line 530F and the IMP− line 532F so that during an impedance test the selected one of the 4051 switches 436–444 disconnects the corresponding electrode from the G minus conductor and all of the other electrodes are connected to the G minus conductor. More particularly, the IMP− conductor 532F is supplied through a buffer 540F to the conductor 542F which is connected to the pin 3 terminal of the 4051 switches 436–444 and hence to one side of all of these semiconductor analog switches.

In order to illustrate the interconnection of the 4051 switches 436–444 with the 4066 switches 446–464, reference may be had to FIG. 7A wherein the last two 4051 switches on the IC 438 are shown in conjunction with the last two 4066 switches on the IC 452, these latter switches being connected to the electrodes E14 and E15. The IMP+ conductor 536F is connected through the individual resistors 544 to the other side of each of the 4051 switches. The control lines of these 4051 switches are controlled from the last half of the shift register 418 and the shift register 420 as described heretofore. The output of each one of the 4051 switches is employed as the control line for the corresponding 4066 switch. Thus, each of the switches in the IC 438 are connected over a conductor 546F to the control line of the corresponding 4066 switch.

Considering first the operation of the 4051 switches and the 4066 switches during the normal mode of operation of the EEG system during this normal mode of operation the conductor 536F is low and the conductor 542F is high. Accordingly, when one of the 4051 switches is selected, for example, the switch 438, a positive potential is supplied through this switch and over the conductor 546 to control the corresponding 4066 switch 452 so that the electrode E14 is connected to the G minus conductor 466. None of the other 466 switches are connected to the conductor 466 during the normal mode of operation. In the impedance test mode of operation, the conductor 536F is high and the conductor 542 is low. Accordingly, as soon as the normal-impedance mode switch in the facilities 100 is turned to the test position a high potential is applied through the individual resistors 544 to the control inputs of the 4066 switches so that all of the 4066 switches are closed and all of the electrodes are connected to the G minus conductor 466. However, as soon as a particular electrode is selected by the forty-position rotary switch and the data corresponding thereto supplied over the lines 106 and registered in the last half of the register 418 and the register 420, a corresponding one of the 4051 switches is supplied with a control pulse to close the switch. Assuming that the switch 438A is selected, when this switch is closed the low potential on the conductor 542F is connected through the switch 438A and over the conductor 546 so as to open the switch 552A while all of the other 4066 switches remain closed. Accordingly, all of the patient electrodes, except the selected one which is connected to the G plus conductor, are connected to the G minus conductor 466 in the impedance mode test of operation. The rotary switch may then be moved to each different position to check the impedance of a particular electrode with respect to all of the other electrodes of the system connected in parallel. The 4066 switches in the IC 464 which control selection of the average conductor 96 and the ear electrodes are connected through resistors 543 and 545 respectively to minus six volts rather than to the IMP+ conductor 536F as with the other switches. This is to prevent shorting of electrodes in the event that an impedance test is made of one of the electrodes in the ear reference.

During the impedance test operation an a.c. impedance test signal is developed within the head box 50 and is applied to the G plus conductor through the resistor 108. Also the G minus conductor 466 is connected to isolated ground so that the a.c. voltage developed by the series combination of the selected electrode and all of the other electrodes connected in parallel is applied to the input of the amplifier 58. More particularly, during the impedance test mode of operation, an a.c. oscillator indicated generally at 547 is enabled and supplies an a.c. signal of approximately 10 Hz to the flip-flop 548. A switch 549, which is open during the normal mode of operation, is closed by the potential impressed upon the conductor 536F during the impedance test operation so that the a.c. impedance test signal is supplied through the resistor 108 to the G plus conductor. The positive signal on the conductor 536F during the impedance test operation also functions to close a switch 550 which connects the G minus conductor to isolated ground.

In order to provide a visual impedance display at the head box 50 so that the operator who actuates the rotary switch in the facilities 100 may readily determine the impedance of the selected electrode, the output of the first amplifier 58, which is also located in the head box 50, is supplied to the impedance test display 102.

More particularly, the output of the amplifier 58 is supplied to the drain terminal of an n-channel JFET 564. The mod signal on the conductor 120 is supplied through a resistor 560 to a PNP transistor 562 the collector o which is connected to the gate of the JFET 564. By applying the mod signal on the conductor 120 to the gate of the JFET 564 modulation that was superimposed on the output of the amplifier 58 by the polarity reversing switches 116 is removed so that an amplified signal corresponding to the a.c. impedance test signal is produced at the source terminal of the JFET 564. This a.c. signal is coupled through a capacitor 566 to the rectifiers 568 and 570 so that a d.c. signal is developed across the resistor 572 which is applied to the input of a d.c. amplifier 574. The output of the amplifier 574 is applied to the plus terminals of a series of comparators 576–594 the outputs of which are employed to control individual LED's 596–614, inclusive. The minus inputs of the comparators 576–594 are connected to a voltage divider network comprising the resistors 616–634 which are connected in series between a plus six-volt reference source and a conductor 636. During the normal mode of operation of the EEG system the conductor 636 is at a plus potential so that the outputs of the comparators 576–594 are all zero and none of the LED's 596–614 are lit. However, in the impedance test mode of operation the d.c. potential on the IMP-conductor 542 is supplied through a transistor 638 and over the conductor 112 to an opto-isolator 640 is necessary because the impedance display facilities including the comparators 576–594 and LED's 596–614 are all operated at system ground within the lead box 50, whereas the above-described switching facilities which are controlled by the potential on the conductors 536 and the 542 and all operated with respect to isolated ground. The output of the opto-isolator 640 is supplied through an amplifier 642 to the conductor 636 so as to control the comparators 576-594, as described above. During the impedance test operation the potential on the conductor 636 is low and hence a potential is applied to the voltage divider 616-634. A number of the LED's 596-614 will thus be lit depending upon the d.c. level of the output from the amplifier 574 which is applied in parallel to the plus inputs of the comparators. Accordingly, the operator has an immediate visual indication of the impedance level of the electrodes being tested.

Preferably, the comparator 594 energizes the LED 614 when the impedance circuit is operating. The amplitude of the signal from the amplifiers 592 corresponds to an electrode impedance of at least 1000 ohms. The comparator 590 is set to respond to an impedance of at least 3000 ohms, the comparator 588 at least 5000 ohms, the comparator 586 to at least 2000 ohms, the comparator 584 to at least 10,000 ohms, the comparator 582 to at least 15,000 ohms, the comparator 580 to at least 20,000 ohms and the comparator 578 to at least 50,000 ohms, and the comparator 576 to at least 100,000 ohms.

Referring now to FIGS. 15 to 17 wherein the details of the amplifier 58 and its associated calibration, imbalance and power supply components are shown, the G plus conductor 434 is connected to the gate electrode of an n-channel JFET 560 and the G minus conductor 466 is connected to the gate electrode of an n-channel JFET 652, these elements forming the input stage of a differential amplifier of the rebalancing type which is provided to maintain a high input impedance at the input of the amplifier 58 while maintaining a constant gain through amplifier 58. The sources of the JFET 650 and 652 are connected together through the rebalancing resistor 654 and a symmetrical constant current network, comprising the resistors 656 and 658 and the potentiometer 660 is connected through the constant current transistor 662 to the minus 15 volt supply, the transistor 662 acting as a current source for the differential input stage. Since the amplifier 58 must have a high signal to noise ratio, the value of the rebalancing resistor 654 is preferably quite low so that its noise contribution is minimized. Preferably, the resistor 654 has a value of 1000 ohms which is low enough to minimize noise without drawing excessive current from the rebalance circuit.

The outputs of the JFET's 650 and 652 derived across the resistors 664 and 666 are applied to the base electrodes of the second stage transistors 668 and 670, respectively. The collectors of the transistors 668 and 670 are direct coupled to the next transistor differential stage comprising the transistors 672 and 674. The emitters of the transistors 668 and 670 are connected through the small parasitic suppression resistors 676 and 678 and through the constant current transistor 680 to the plus 15 volt supply. The output of the transistor stage 672, to 674 is coupled through a current mirror transistor 682 to the common emitter differential output stage comprising the transistors 684 and 686, the common emitter connection of this stage forming the output of the amplifier 58.

As discussed generally heretofore, the output of amplifier 58 is reversed in polarity by means of the reversing switches 116 which are controlled by the mod signal on the conductor 120. More particularly, the signal on the conductor 120 is coupled through a driving transistor 690 to the LED of the opto-isolator 122 the output of which is coupled to a squaring amplifier 692. The output of the amplifier 692 controls the switches 116 directly and through the inverter 694, so that symmetrical switching of the output of the amplifier 58 with respect to isolated ground is provided. The switched output is supplied to the winding 696 of the isolating transformer 110.

Preferably, the switches 116 comprise a type AHO153 IC which provides a very low resistance when the switches are closed, a very high resistance when the switches are off, and provides a wide analog signal range when the switches are closed.

As discussed generally heretofore, a feedback signal is derived from the isolating transformer 110 to rebalance the input of the amplifier 58. More particularly, the feedback winding 698 of the transformer 110 is coupled through the polarity reversing switches 118 and through the symmetrical resistors 700 and 702 to the rebalancing resistor 654. With this arrangement the current through each input JFET 650 and 652 is maintained virtually constant over a wide range of amplitude and frequency.

As discussed generally heretofore the isolating transformer 110 is provided to isolate the switched output of the amplifier 58 from system ground. Transformer isolation is preferable over capacitive coupling because of the fact that capacitive coupling would increase the parasitic capacitance between isolated ground and system ground too much. On the other hand, optical coupling from the output of the amplifier 58 to the system ground level would introduce too much noise in the input of the common signal path and prevent the detection of relatively small brain wave signals in the order of a few micro-volts in the presence of such a high noise level.

While transformer coupling is thus desirable, it will be recalled that the electrode pair signal voltages amplified by the amplifier 58 may contain relatively large d.c. components of opposite polarity during successive channel periods. These d.c. components must be transmitted through the isolating transformer 110 to the input of the second amplifier 60 wherein base line suppression and elimination of these d.c. components is partially accomplished. The polarity reversing switches 116 and 118 are controlled by the mod signal on the conductor 120. Since the output of the amplifier 58 which is coupled to the winding 696 may include a large d.c. component of one polarity for several adjacent channel periods, it is necessary to preserve this d.c. component by means of the feedback winding 698 on the transformer 110. With such an arrangement the output of the amplifier 58 will slew to correct for the L/R decay of the transformer 110. Accordingly, the L/R decay of the transformer 110 will be decreased by the loop gain of the amplifier. However, if the output of the amplifier 58 were applied to the winding 696 without switching the polarity thereof, and a number of adjacent channels have large d.c. components of the same polarity, the amplifier 58 would slew into saturation in an attempt to maintain the output level thereof constant over several channel periods. By reversing the output of the amplifier 58 every four channel periods by means of the switches 116, the amplifier 58 is prevented from slewing into saturation under such conditions.

Also, in accordance with an important aspect of the invention the mod signal reverses in phase every four adjacent channels, so that during successive channel period frames the polarity of any particular channel period will be reversed from its polarity during the preceding channel period frame. Since there are twenty channel periods and the output of the amplifier 58 is reversed every four channels by the mod signal, a series of five reversals will occur during each channel period frame so that during successive frames the polarity of any one channel will be reversed with respect to its polarity during the preceding frame.

Preferably, the feedback winding 698 is bifilar wound with respect to the winding 696 so as to minimize the leakage inductance between these windings and hence maximize the band width of the amplifier. However, the output winding 704 of the isolating transformer 110 is positioned relatively far from the bifilar wound windings 696 and 698 to avoid capacitance feedthrough to the output winding 704 which is connected to system ground. Any capacitance feedthrough between the output winding 704 and the bifilar windings 696 and 698 will add to the parasitic capacitance of the isolated ground system with respect to system ground. Because of its spacing, the winding 704 has greater leakage capacitance and inductance and its high frequency break point is also less. However, the high frequency break point of both secondaries 704 and 698 is extremely high because it has been expanded by the loop gain of the amplifier 58. Accordingly, the transformer output of the present invention is an extremely broad band system. Furthermore, since the d.c. component is preserved through the isolating transformer to the winding 704, any voltage offset in the first amplifier can be observed as a square wave at the output winding 704. This may be used in the testing of the common amplifier path and for other purposes.

As discussed generally heretofore, an isolated power supply 152 is provided in the head box 50 to supply operating voltages to the amplifier 58 and other isolated circuitry within the head box 50. More particularly, the signal appearing on the #1 clock line 710, from clock control 146 is supplied through a resistor 712, and inverter 714, and a second inverter 716 so as to provide a pair of oppositely polarized input channels for the switching transistors 718 and 720. The emitters of the transistors 718 and 720 are connected to system ground and the collectors thereof are connected to the windings 722 and 724 respectively of the isolating transformer 150. Each input channel for the transistors 718 and 720 comprises a filter circuit comprising a series resistor 726 and a shunt capacitor 728, a diode 730 being connected across the resistor 726 to form a dead time between switching periods of 718 and 720. This insures that the transistors 718 and 720 are not on at the same time. The output of this filter is supplied through an inverter 732 and the resistor 734 to the base of the switching transistors 718 and 720.

The transformer 150 is provided with a secondary winding 736 which is isolated from system ground and may be employed to develop the necessary plus and minus d.c. operating voltages for the amplifier 58 and other isolated circuitry within the head box 50. One such circuit is shown as comprising the diodes 738 and 740 and filter capacitor 742 which are employed to develop a minus fifteen volt supply voltage. A similar circuit is employed to develop plus fifteen volts. Other voltages of different levels are also developed from the winding 736 as required for the various circuitry within the head box 50.

By employing the signal on the clock line 710 which is synchronous with the channel period switching as the input of the amplifier 58, rather than the conventional sixty-cycle power supply, the d.c. voltages required with the isolated section 154 may be developed without undesirable signal pickup due to sixty-cycle components which would be within the frequency range of the brain wave signals being measured. At higher frequencies the power transformer is also more efficient and hence can be smaller. Also, no switching takes place during the sample period, thereby reducing undesirable switching pick-up.

As discussed generally heretofore, a d.c. calibration voltage is developed at the master control panel 126 and is supplied over the conductor 128 to the head box 50 when it is desired to calibrate the common signal head of the EEG system of the present invention. More particularly, the d.c. calibration signal which is supplied to the conductor 128 is coupled to an amplifier 746 the output of which is connected to a winding 748 on the isolation transformer 132 by means of the polarity reversing switches 134. The oppositely polarized #1 line signals developed across the input and output of the inverter 716 are employed as input signals to control the switches 134 so that the d.c. output of the amplifier 746 is reversed in polarity at the channel frequency and is applied to the winding 748. A feedback winding 750 is provided on the transformer 132 which is coupled through the polarity reversing switches 136 to the minus input of the amplifier 746. The switches 136 are also controlled by the oppositely polarized #1 line signals so that the feedback to the minus input of the amplifier 746 is a d.c. calibration signal. The output winding 752 of the transformer 132 is coupled through the polarity reversing switches 138 and the symmetrical resistors 140 and 142 to the calibration resistor 144.

The switches 138 are controlled by the outputs of a pair of AND-gates 754 and 756 to one input of which is applied a control signal when the calibrate mode switch is depressed on the master control panel 126. More particularly, when the calibrate mode control signal is supplied to the conductor 158 this signal is coupled through a driving transistor 758 to the opto-isolator 760 so that the output signal developed on the output lead 746 of the opto-isolator 760 is isolated from system ground. This calibration control signal is then applied through the squaring amplifier 746 to one input of the AND-gates 754 and 756. The other input of these AND-gates is supplied from the transformer winding 736 through the isolating resistors 766 and 768 and the buffer amplifiers 770 and 772. The polarity reversing switches 138 are thus controlled by the AND-gates 754 and 756 so that the switches 138 are not operative during the normal mode of operation of the system and hence do not normally apply a switched d.c. calibration signal to the resistor 144. However, when a calibrate mode control signal is received on the conductor 158 the switches 138 are controlled through the enabled AND-gates 754 and 756 so that they are switched in synchronism with the primary winding switches 134 so as to reconstruct the original d.c. calibration voltage on the conductor 128, which is then applied to the calibration resistor 144 through the resistors 140,142.

As discussed generally heretofore, the same amplifier 746 and isolation transformer 132 are employed when an imbalance test is to be made rather than a d.c. calibration test. More particularly, when an imbalance test is to be made an a.c. imbalance signal is supplied over the conductor 128 in place of the d.c. calibration signal. This signal is applied to the amplifier 746 wherein it is amplified, modulated by the switches 134 and applied to the winding 748. The corresponding voltage appearing on the secondary winding 752 is then controlled by means of the polarity reversing switches 164 and supplied to the inbalance output conductor 166.

The switches 164 are controlled directly from the a.c. signal developed across the winding 736 through the buffer amplifier 770 and 722 and hence are reversed at channel frequency. Since the switches 164 are not disabled during a d.c. calibration operation, these switches, which are connected in parallel with the switches 138 across the winding 752, will function to supply a d.c. calibration signal to the imbalance conductor 166 during the d.c. calibration test. However, as discussed generally heretofore, during a d.c. calibration test the G plus and G minus conductors 434 and 466 are connected to the calibration input so that the application of a d.c. signal to a patient electrode through the imbalance resistors 168 will have no effect upon calibration of the amplifier 58. Of course, once the d.c. calibration signal is removed from the conductor 128, no signal will be impressed upon the imbalance conductor 166 to interfere with normal patient electrode measurements.

Referring now to FIG. 23 wherein the details of the address shifter 160 are shown, the six data lines 250 which may be supplied either from the EAROM 252 or the override RAM 268, provide two sequential sets of data during each channel period. The first six bits of data during the first half of each channel period corresponds to the address of the electrode which is to be connected to the GI conductor. The second six bits of data which is present on the conductor 250 during the last half of each channel period corresponds to the electrode address to be connected to the G minus conductor. The data lines 250 are supplied through a buffer, which may comprise a type 4050 IC, to a pair of parallel in to serial out shift registers 782 and 784. These shift registers may be type 74L165 IC's.

As described generally heretofore, a thirteenth bit of data is supplied from the averaging RAM 259 under control of the average counter 261 which is synchronized with the counter 490 in the head box 50, so that during successive channel periods the different patient electrodes which are to make up the average may be selected. This thirteenth bit of data is supplied over the conductor 786 and through an inverter 788 to the thirteenth bit input of the register 782. The data supplied through the buffer 780 is loaded into either the register 782 or the register 784 under the control load pulses which are applied to the conductor 790 near the end of each half channel period. More particularly, these reset pulses are supplied through the buffer 792 to a differentiation circuit comprising the capacitor 794 and the resistor 796 the output of which is supplied to one input of the AND-gates 798 and 800. The output of the AND-gate 798 is supplied to control loading of the register 782 and the output of the AND-gate 800 is supplied to control loading of the register 784. It will thus be seen that the registers 782 and 784 are loaded near the end of each half channel period.

The thirteen bits of data stored in the registers 782 and 784 are read out serially on the output conductor 806 of the register 782 to a line driver 808 which drives the address line 90. The driver 808 may be a type 75121 IC. More particularly, a high speed oscillator 810 is provided, which operates at a frequency of approximately 2 MHz and is controlled by a counter 812. The counter 812 may comprise a 74LS93 type IC. A differentiation circuit comprising the series capacitor 814 and the resistor 816 is connected from the $\overline{EB}$ line supplied from the clock control 146 so that a sharp pulse is produced at the start of each channel period which is supplied through the inverter 818 to reset the counter 812. The counter 812 then enables the oscillator 810 until it has counted to thirteen and stops until it is again reset by a pulse supplied through the inverter 818 at the start of the next channel period. Accordingly, a series of thirteen pulses, occurring at a two megacycle rate, are supplied over the conductor 820 to shift the data stored in registers 782 and 784 onto the address line 90. To accomplish this the data stored in the register 784 is first shifted into the register 782, over the conductor 822, as the data in the register 782 is being shifted out of this register onto the conductor 806. As a result, the thirteen bits of data are serially supplied to the address line 90 at the beginning of each channel period. As discussed heretofore, the first six bits of data represent the electrode to be connected to the G plus conductor, the second six bits of data represents the electrode to be connected to the G minus conductor and the thirteenth bit represents a particular electrode to be included in the average.

Referring now to FIGS. 18, 19 and 20, wherein the details of the second amplifier 60 are shown, the signal from the output of the amplifier 54 which appears across the winding 704 and is at system ground, is transmitted over the cable 52 and through the resistor 176 to the gate electrode of an n-channel JFET 830. As discussed generally heretofore, the input signal is also supplied to the plus input of the amplifier 60 and one of the capacitors 184 is selectively connected to this plus input during each of the twenty successive channel periods. More particularly, the input signal is applied through the resistor 178 to one side of a potentiometer 832 the other end of which is connected through the resistor 180 to system ground. The arm of the potentiometer is connected through the series time-constant resistor 182 to a series of 4051 type semiconductor analog switches 834. The common output of 870, 872 and 874 switches on conductor 836 is supplied to the gate electrode of an n-channel JFET 838 which forms the other input of the differential amplifier 60.

Considering first the manner in which a signal is amplified through the amplifier 60, the source electrodes of the JFETS 830, 838 are supplied from the arm of a potentiometer 840 and through a constant current transistor 842 to the minus fifteen volt supply. A pair of oppositely polarized diodes 844, 846 are connected across the drain electrodes of the JFETS 830, 838 to limit the maximum amplitude of signal which may be transmitted to the succeeding stage so as to remove relatively long transient signals which may be applied to the input of the amplifier 60.

The outputs of the JFETS 830, 838 are applied to the bases of the transistors 848 and 850 which form the second differential stage of the amplifier 60. The collector of the transistor 850 is supplied to the base of an emitter follower transistor 852 and the collector of the transistor 848 is connected to the base of an emitter follower transistor 854. As discussed generally heretofore, the feed forward gain of both the amplifiers 60 and the amplifier 62 is varied at the same time that the closed loop gain is varied by varying the amount of feedback signals supplied to the feedback resistor 188. The open loop or feed forward gain is varied by means of the semiconductor analog switches 198 which may comprise type 4041 IC's which receive control signals, one directly and one through inverter 855 through an AND/OR selector 856 from either the master control panel 126 or from the microprocessor 254 through the override RAM 268. More particularly, the master control panel 126 provides a digital signal on the output leads GS1, GS2, GS3 and GS5 which is effective to select one of the switches 198 and connect one of the resistors 858 between the emitter of the transistor 852 and the emitter of an amplifier transistor 860. The signal from the emitter of the transistor 854 is applied to the base of the transistor 860 so that a difference signal is developed in the collector circuit of the transistor 860 which is supplied to the push pull output transistors 862 and 864, the output of the amplifier 60 being derived from the common emitter circuit of the transistors 862, 864. The open loop gain of the amplifier 60 may thus be varied by the setting of the master sensitivity switch 866 on the master control panel 126.

In the alternative, and in accordance with an important aspect of the present invention, the resistors 858 may be selected from the microprocessor 254 through the override RAM 268 which provides an appropriate digital signal on the conductors GO1, GO2, GO3 and GO4, together with a control signal on the conductor CON which is supplied to the pin 14 terminal of the IC 856 and through an inverter 868 to pin 9 of the IC 856. Accordingly, the open loop gain of the amplifier 60 may be varied on an individual channel basis through the microprocessor 254 by applying an appropriate control signal and switch selection signal to the selector 856 during any particular one of the twenty channel periods so that one of the resistors 858 is selected during this channel period.

In order to selectively control the feedback signal which is supplied to the input of the JFET 830 on an individual channel basis, the semiconductor analog switches 190 are provided which may comprise type 4051 IC's. The output of the amplifier 60 is supplied through a series of series connected resistors 192a, 194a, 196a, etc., to ground system, different points on the voltage divider formed by these resistors being selected by means of the switches 190. The switches 190 receive control signals, one directly and one through inverter 855 through the AND/OR selector 856 from either the master control panel 126 or through the microprocessor, as discussed in detail heretofore. Accordingly, a variable portion of the output signal appearing at the output of the amplifier 60 is supplied to one end of the feedback resistor 188 through the switches 190 on an individual channel basis, or through the master control panel 126.

As discussed heretofore, the capacitors 184 are selectively connected to the plus input of the JFET 838 on an individual channel basis to remove the d.c. component of each of the electrode pair signal voltages which may be of large amplitude and may in fact be of the opposite polarity for adjacent channels. To this end, the semiconductor analog switches 870, 872 and 874, which may comprise type 4051 IC's, are provided for each of the twenty capacitors 184, these capacitors being connected from one terminal of these switches to system ground. The low order control lines 1, 2 and 4 from the clock control 146 are employed to select one of the switches within each of the IC's 870, 872 and 874 and selection between these IC's 870, 872 and 874 and selection between these IC's is made by means of the control lines 8, 16 from the clock control 146 through the OR-gates 876, 878 and 880, these OR-gates having as one input the control signal EA from the clock control 146. It will be recalled from the previous general description that the MOD signal on the conductor 120 includes a four-channel term which introduces a modulation component in the signal supplied to the amplifier 60 which is reversed in polarity every other channel frame. Accordingly, it is necessary to disable the switch in 870, 872 and 874, by means of the EA signal, during every alternate channel period frame so that the capacitors 184 will not be charged in opposite directions during successive frames and hence lose the offset voltage which is to be established across each of these capacitors proportional to the d.c. or slowly varying component of each channel. Furthermore, the EA signal closes each one of the switches 870, 872 and 874 at a relatively early point in each channel period so that switching transients may die down before a corresponding switching operation is made in the succeeding amplifier 62, as will be described in more detail hereinafter.

The common output of the switches 870, 872 and 874 is connected over the conductor 836 to the gate electrode of the JFET 838 so that different ones of the capacitors 184 are selectively connected to this input during the twenty successive channel periods which comprise one channel frame. By way of illustration only, the resistor 178 may have a value of 374 ohms, the potentiometer 832 a value of 20 ohms, the resistor 180 a value of 750 ohms, the resistor 176a a value of 6,490 ohms and the resistor 188 a value of 13,000 ohms. The series time constant resistor 200 may have a value of 13,000 ohms and each of the capacitors 184 may have a value of 4 microfarads.

As discussed generally heretofore, for an a.c. input signal the negative input of the amplifier 60 follows input signals directly and the positive side of this amplifier is filtered in accordance with the time constant of the resistor 182 and one of the capacitors 184 applied to the positive input. The voltage divider action of the series resistors 178 and 180 is provided so that when a relatively high input voltage from the amplifier 58 is supplied the switches 870, 872 and 874 are not called upon to switch as large an amplitude of signal. Also, the voltage divider ratio between the resistor 178 and 180 is made the same as the feedback ratio between the resistors 188 and 176 so that the DC gain of the amplifier is zero, with a low frequency break point equal to the time constant formed by the capacitance at the positive input and the time constant resistor.

If a series of twenty channels are provided, and twenty capacitors are sequentially connected to the plus input of the amplifier 60, the effective time constant of each time constant circuit is increased by a factor of twenty so that relatively small capacitors 184 may be employed while providing relatively low frequency filtering action at the input of the amplifier 60. Furthermore, this time constant is increased by the time during which the capacitor is not connected into the circuit, i.e. its duty cycle.

Specifically, the time constant of each channel is given by the formula $TC = NRC/DC$ where N is the number of channels, RC is the time constant of the resistor 182 and the capacitor 184 and DC is the duty cycle or percent of time a capacitor is switched into the system. As discussed generally heretofore, the switches 870, 872 and 874 are all disabled during alternate frames by means of the EA signal applied to the OR-gates 876, 878 and 880 so that the effective time constant for each channel is further increased by this reduction in duty cycle.

In accordance with an important aspect of the invention, the gain of the amplifier 60 is automatically reduced during the off period of the EA signal so that the amplifier 60 will not amplify the switching voltages produced as a result of the switching in the head box 50 so that large transients will not build up. A similar arrangement is employed in the third amplifier 62 which is controlled by the EA1 wave form. More particularly, the EA signal is supplied through an inverter 871 to a series of tri-state buffers 873, 875, 877 and 879 which may comprise type 4503 IC's. The output of the inverter 871 is supplied to the buffers 873, 875, 877 and 879 which connect the lowest order bit line GS5 to a plus voltage and the other lines GS1, GS2 and GS3 to a minus voltage. The switches 190 are thus controlled through the and/or selector 856, so that the amplifier 60 is setting to its minimum gain setting during the off periods of the EA signal irrespective of the gain setting on the master control panel 126.

While various precautions are taken in connection with the common signal path of the present invention, to prevent overload of the signal path and off-scale deflection of the pens 80, it may happen that a large input signal due to a muscle artifact, or the like, may cause overloading of one or more of the channels and off-scale deflection of the recording pens. In accordance with a further important aspect of the present invention, a reset button is provided on a master control panel 126 which when depressed supplies a control signal over the conductor 882 and through a buffer amplifier 884 to one input of a series of OR-gates 886, 888 and 890. This signal is applied to the IC 834 and has the effect of shorting the resistor 182 so that the relatively long time constant formed by this resistor and each of the capacitors 184 is shortened to permit this amplifier to recover quickly from overload. More particularly, the conductor 892 is connected to the conductor 836 through one of the switches 834 when a reset signal is produced so that the resistor 182 is shorted out. Since the resistor 182 is common to all channels, a single one of the switches 834 is able to accomplish this reset function. During normal operation it has been found that when an undesirably large injection signal is introduced into the capacitors 184 it causes an undesired deflection of the recording pens in the individual recording channels. In order to illustrate how this charge injection voltage comes out, reference may be had to FIG. 19A wherein a simplified diagram of the switching action relative to the capacitors 184 is shown, together with a charge compensation circuit of the present invention. More particularly, the capacitors 184 are individually connected to one of the semiconductor analog switches 870, 872 and 874, two of these switches being illustrated as the switches 870a and 870b in FIG. 19A. The other terminal of these switches is connected to the plus input of the amplifier 60 over the conductor 836. Due to the construction of the semiconductor analog switches 870a and 870b, stray capacitances 894 and 896 are present between the control terminal 898 of each switch and the input and output terminals of this switch. Furthermore, a relatively large control voltage which varies from plus six volts to minus six volts and controls opening and closing of the switch is applied sequentially to the control terminals 898 of the switches 870 during the twenty successive channel periods. This relatively large control voltage is coupled through the stray capacitances 894 and 896 to the capacitor 184 when the switch 870 is closed and discharges relatively slowly since the capacitor 184 is large as compared to the stray capacitance 894. When the switch 870a is opened approximately 35 microseconds later the stray capacitance 896 may discharge quickly since it remains connected to the resistor 182 and has a much shorter time constant since the capacitance 184 is not connected. However, the stray charge 894 must discharge through the resistor 182 at a relatively slow rate. Since the switch 870 is closed a relatively large number of times per second, the stray capacitance 894 functions to inject a relatively large offset potential into the capacitor 184 during periods when the switch 870 is closed. When the reset button is depressed and the resistor 182 shorted a lower value of offset voltage is developed across the capacitor 184. However, when the reset button is released and the resistor 182 is reconnected into the circuit a large value of offset voltage is produced but the time constant of the circuit is now substantially increased since the resistor 182 is in the circuit and an undesired offset potential is developed so that undesired deflections of the recording pens are produced in each channel.

In accordance with an important aspect of the present invention, a charge injection compensation system is provided to counteract the above-described offset potential produced in each channel when the reset button is released. More particularly, a series of semiconductor analog compensation switches 900, 902 and 904, which may comprise type 4051 IC's, are employed sequentially to apply compensation voltages which are produced at the arms of a series of individually adjustable compensation potentiometers 906 and through a common series compensation capacitor 908 to the common output conductor 836 of the switches 870, 872 and 874, a pair of the switches 900a and 900b on the IC 900 being shown in the simplified diagram in FIG. 19A. Each of the potentiometers 906 is connected between plus and minus supplies so that the arm of each potentiometer may be adjusted to provide an individual compensation voltage for each channel. Such an arrangement is necessary because the stray capacitances 894 and 896 associated with each of the switches 870, 872 and 874 may vary as much as fifty percent from switch to switch and hence require individual compensation voltages.

The common output of the switches 900, 902 and 904 is also connected through a resistor 910 to ground. The switches 900, 902 and 904 are actuated in synchronism with the switches 870, 872 and 874 which connect the capacitors 184 to the plus input of the amplifier 60. However, a slight delay is introduced in the actuation of the switches 900, 902 and 904 to insure that the capacitors 184 are connected into the circuit before the compensation charge injection signal is applied thereto. To this end, the series resistors 912, 914 and 916 and the shunt capacitors 918, 920 and 922 provide time delay networks between the outputs of the gates 876, 878 and 880 and the switches 900, 902 and 904.

The capacitor 908 is relatively small, in the order of fifty-one picofarads, so that it can transmit the rapidly changing step voltages produced at the arms of the individually adjusted potentiometers 906 to the input of the amplifier 60 during successive channel periods. Accordingly, as each one of the switches, such as the switch 870a is closed to connect the capacitor 184 to the plus input of the amplifier 60, a step voltage compensation signal is supplied from the arm of the potentiometer 906 through the switch 900a and differentiated across the capacitor 908 to compensate for the offset potential developed across the capacitor 184. The height of this step function compensation signal is determined by the setting of each of the potentiometers 906 and is adjusted for the particular value of stray capacitance 894 associated with a particular one of the switches 870. The compensation side of the capacitor 908 is normally held at ground potential through the resistor 910. However, when the switch 900a is closed, by an application of a control voltage to its control terminal 898a, the voltage on the capacitor 908 changes to that on the arm of the corresponding potentiometer 906. This voltage step appearing at the capacitor 908 provides a charge injection to the capacitor 184 which exactly balances the offset produced across this capacitor. When the switch 900a opens the reverse procedure obtains and a voltage step in the opposite direction of equal magnitude is produced, this coinciding with the opening of the corresponding switch 870a. As a result, the pen deflections due to reset transients can be held to less than five microvolts at maximum gain of the amplifier 60 with the compensation arrangement of the present invention. It should be noted that the variation in the gain of the amplifier by selecting some fraction of the output voltage to drive the feedback resistor 188 does change the feedback ratio and hence does affect the d.c. rejection of the amplifier 60 though only by a small percentage which is then calculated into the value of the feedback divider.

In the amplifier 60 the single time constant resistor 182 is employed for all channels and the time constant resistor is varied on an individual channel basis only in the input of the third amplifier 62. This is done so that the increased switching transients which are produced when both the resistor and the capacitor of the time constant circuit are switched on the individual channel basis will be done at a point after the gain of the second amplifier 60. However, in order to simplify the present specification, the circuitry required to switch the time constant resistor, which is employed in the multiplier 62, is shown in FIGS. 18 to 20 of the drawings. In other respects, the amplifier 62 is similar to the arrangement shown in FIGS. 18 to 20 except that in amplifier 62 no override control of the forward and feedback gain of the amplifier is shown. Accordingly, in amplifier 62 the AND/OR selector 856 and its associated circuitry can be eliminated and the master control panel employed directly to control the switches 190 and 198 over the conductors GS1, GS2, GS3 and GS5.

Considering now the circuitry required in amplifier 62 to change the value of the time constant resistor 182 on an individual channel basis, an AND/OR selector 924 is provided which has two inputs MT1 and MT2 from the master control panel 126 which permit the manual selection of different time constant resistors 200 and 202 which may be added in series with the resistor 182 through the switches 834 to the output conductor 836. In addition, the AND/OR selector 924 is provided with two inputs IT1 and IT2 which may be controlled from the microporcessor 254 through the override RAM 268. A control signal TO from the override RAM 268 controls the AND/OR selector 924 so that selection of the time constant resistor value on an individual channel basis may be accomplished through the microprocessor 254 by shifting control of the switches 834 to the input conductor IT1 and IT2. The output of the AND/OR selector 924 is supplied to the other input of the OR-gates 886, 888 and 890 so that the switches 834 may be selectively controlled on an individual channel basis to alter the value of the time constant resistor in the amplifier 62.

Referring now to FIG. 22 wherein the details of the master control panel 126 are shown, a signal from the imbalance oscillator 162 is supplied through the imbalance push button 930 and through the potentiometer 932 to the top of the voltage divider network comprising the series resistors 934-948 to ground. A rotary switch 950 is employed selectively to connect a point on the voltage divider 934-948 to the output conductor 128 so that an a.c. imbalance signal can be supplied through the cable 52 to the amplifier 746 in the head box 50. Accordingly, when the imbalance button 930 is depressed, an imbalance signal is supplied through the isolating resistors 168 to the patient electrodes 56 so as to perform an imbalance test as described in detail heretofore.

When the common signal path is to be calibrated a calibration button 952 is depressed. When this occurs a six-volt regulated voltage, which is produced across the Zener diode 953, is supplied through the switch section 954a of a mode switch 954, the button 952 and a potentiometer 956 to the upper end of the voltage divider 934-948. Accordingly, a d.c. calibration signal is supplied over the conductor 158 to the input of the amplifier 746 in the head box 50, it being noted that the same voltage divider 934-948 is employed for both the imbalance and calibration operations.

The master control panel 126 also includes a reset button 958 which when depressed provides a five-volt signal to a pull down resistor 964 connected to conductor 882. Accordingly, when the reset button 958 is depressed, a positive signal is supplied over the conductor 882 to the buffer amplifiers 884 in the amplifiers 60 and 62, respectively, to short the time constant resistors in the input of each of these amplifiers, as described in detail heretofore.

The master control panel 126 also includes a programmable rotary switch 970 which is employed to select a particular one of the montages which is stored in the EAROM 252. More particularly, the switch 970 develops a digital signal on the output conductors 972, 974, 976 and 978 which is supplied through the preset selector 264 as the higher order bits to the AND/OR selector 260 so as to select a particular one of the montages stored in the EAROM 252.

The master control panel 126 also includes a master sensitivity switch 866 which is a programmable rotary switch providing a digital signal on the output conductors GS1, GS2, GS3 and GS5 which is supplied to the amplifier 62 to control the gain of this amplifier on an overall, non-channel charging basis.

In order to control the value of the time constant resistors in the amplifier 62 a two-section rotary switch 980 is provided on the master control panel 126 which provides a digital signal on the output conductors MT1 and MT2 which is supplied to the AND/OR selector 924 in the amplifier 62. With this arrangement, the time constant of the third amplifier 62 can be varied on a master, non-channel basis by actuation of the switch 980 to the four positions indicated.

As discussed generally heretofore, the master control panel 126 is provided with facilities for changing the value of the series resistors 230, 232 in the input of the demultiplexer 74. To this end a two-section rotary switch 982 is provided which functions to produce a digital signal on the output conductors 984 and 986 which are employed in the demultiplexer 74 to control selection of the resistors 230, 232 as will be described in more detail hereinafter.

The mode switch 954 is provided with a second section 954b which controls the application of power to the chart motor when the switch 954 is in the chart, calibrate or run positions.

The mode switch 954 is also provided with a third section 954e which is employed to energize the power amplifiers which actuate the galvanometer pen motors 80 in the run and calibrate positions of the mode switch 954.

Referring now to FIG. 21 wherein the details of the channel selectable 30-Hz filter 64 are shown the filter 64 comprises three sections, one of which is shown in detail in FIG. 21, to provide an overall attenuation through the three sections of 60 db. for signals above thirty cycles. Furthermore, this filter is selectable on an individual channel basis from the microprocessor 254 through the override RAM 268 so that if the operator desires to attenuate signals above thirty cycles for a particular channel without affecting the other channels he may do so.

The first section 1010 of the filter 64 comprises a series resistor 1012 which is connected to the plus input of a buffer amplifier 1014. A series of capacitors 1016 are provided for each of the twenty channel periods which are connected to the plus input of the amplifier 1014 through the semiconductor analog switches 1018, 1020 and 1022, which may comprise type 4051 IC's. These 4051 switches are controlled through the buffer 1014 from the clock control 146 which supplies the timing signals on the conductors 1, 2, 4, 8 and 16. The clock control also provides an EA2 signal to the NAND-gate 1036 so that the 4051 switches are disabled during alternate frames, as described in detail heretofore in connection with the amplifier 60. The lower order bit lines from the buffer 1024 control the switches 1018, 1020 and 1022 directly and selection between these IC's is accomplished through the logic including the OR-gates 1026, 1028, 1030 and the inverters 1032 and 1034.

In order to control the filter 64 on an individual channel basis, the EA2 signal which is generated in the clock board is supplied as one input to a NAND-gate 1036 to the other input of which is supplied the 30-Hz control signal from the override RAM 268. Accordingly, the microprocessor 254, or the operator through the keyboard 258, may select particular ones of the twenty channels in which the 30-Hz filter 64 is to be effective. Each of the filter sections, such as the section 1010 provides an attenuation of −20 db/decade from a 30-Hz signal frequency so that a total of −60 db/decade of attenuation is provided by the filter 64. In this connection it should be noted that since there is no amplification following the switching of the capacitors 1016 into the circuit, the charge compensation system employed in the inputs of the amplifiers 60 and 62 and described in detail heretofore in connection with FIG. 19A, is not required for each section of the filter 64.

Referring now to FIG. 24, wherein the details of the polarity reversing switches 68 and demodulation amplifier 66 are shown, it will be recalled from the general description of the system that the MOD signal on the conductor 120 introduces a four-channel component which reverses in polarity for alternate channel frames. This component must be removed prior to the demultiplexing operation since otherwise the signals in successive four-channel increments would alternate polarity. At the same time, it is desirable to introduce an alternate channel polarity reversing signal so that the individual galvanometer pen motors for alternate channels may be arranged with their field structures in opposite directions, as discussed generally heretofore. To this end, the signal from the output of the 30-Hz filter 64 is applied to the input terminal 1040 which is connected to one input of the polarity reversing switches 1042 and 1044. The switch 1042 is connected through the resistor 1046 to the minus input of the amplifier 1047 and the switch 1044 is connected to the plus input of the amplifier 1047. A second set of polarity reversing switches 1048 and 1050 are also provided, one terminal of which is connected to ground. The switch 1048 is connected through the resistor 1052 to the bottom end of the resistor 1046 and the switch 1050 is connected to the plus input of the amplifier 66. A pair of opppositely polarized switching wave forms are applied to the terminals 1054 and 1056, these wave forms having both alternate channel and four-channel reversing components, as discussed in more detail hereinafter. The amplifier 1047 is arranged so that during one four-channel period the signal is supplied to the positive input of the amplifier 1047 and resistor 1052 is grounded so that the amplifier has a gain of plus two. For the opposite polarity of the switching wave forms the amplifier 66 has a gain of minus two. As a result the four-channel component of the MOD signal on the conductor 120 is removed from the output of the amplifier 1047 and the polarity of alternate channels is reversed while providing a gain of two through the amplifier 66. More particularly, the signal on the conductor 1054 controls the switches 1042 and 1050. When these switches are closed the plus input of the amplifier 1047 is grounded, the signal is applied through the switch 1042 and the resistor 1046 to the minus input of the amplifier 1047, and a feedback signal is also supplied to this input through the resistor 1058. When the switches 1042 and 1050 are open and the switches 1048 and 1044 are closed, the signal is supplied through the switch 1044 to the plus input of the amplifier 1047 and a feedback signal is applied through the resistor 1058 to the minus input while the resistors 1046 and 1052 are connected in series to ground through the switch 1048.

The output of the amplifier 66 is supplied to a voltage limiter indicated generally at 72 (FIG. 24) which functions to limit the amplitude of the signal voltages supplied to the demultiplexer 74 to a predetermined maximum value of approximately 1.5 volts so that none of the recording channels 78 and galvanometer pen motors 80 is overloaded. The limiter 72 comprises the elements 1059 which may each be a type 2N4062.

Output of the voltage limiter 72 is supplied to the fifth amplifier 70 (FIG. 25). The amplifier 70 does not provide any additional gain for the electrode pair signal voltage but does provide additional d.c. component or base line suppression in its input circuit, in a manner similar to that described in detail heretofore in connection with the amplifiers 60 and 62. This further d.c. component suppression is necessary because of the fact that while the amplifier 62 is effective to remove most of the d.c. components in the individual channel voltages supplied to its input, since the amplifier 62 may operate at the very high gain of 150, any slight d.c. components which remain between channels is amplified through the amplifier 62 and hence must be removed in the input of the amplifier 70. Furthermore, any drift in the third amplifier 62, due to temperature or power supply variations will also cause variations in the d.c. components of different channels which must be removed. More particularly, operational amplifier 1061 is provided which is operated at a fixed gain of one and the signal from the output of the voltage limiter 72 is supplied through the resistor 176b to the minus input of the amplifier 1061.

The capacitors 184b are sequentially connected to the plus input of the amplifier 1061 through the switches 1063, 1065 and 1067, which may comprise type 4051 IC's. The output of the voltage divider network 178b, 180b, is supplied through the time constant resistor 182b to the plus input of the amplifier 1061. The switch 1069 is employed to selectively short the resistor 182b under the control of the reset pulse on the conductor 882 which is supplied through the squaring amplifier 1071 to the switches 1069. When the reset button is depressed the resistor 182 is shorted and when this button is released and the resistor 182 re-inserted into the circuit offset potentials are produced across the capacitors 184b due to the stray capacitances of the 4051 switches 1063, 1065 and 1067, as described in detail heretofore in connection with amplifier 60. However, since the amplifier 70 does not itself provide additional gain, a common charge injection compensation system may be employed for all twenty channels. More particularly, the EA3 signal, which controls the individual switches 1063, 1065 and 1067 through the OR-gates 1073, 1075 and 1077 is also supplied through a buffer 1079, a delay network 1081, and a further buffer 1083 to a potentiometer 1085 which is connected from the output of the buffer 1083 to system ground. A charge injection capacitor 908a is connected to the arm of the potentiometer 1085 and functions to inject a charge into each of the capacitors 184b just slightly after each capacitor has been connected to the plus input of the amplifier 1061. However, the charge injected for each channel will be the same and will be dependent upon the setting of the potentiometer 1085. By employing the EA3 wave form as a source of charge injection potential, no additional charge injection is made through the capacitor 908A during alternate channel frames which the capacitors 184b are disconnected from the amplifier 1061. The decoder 1080, which may comprise a 74C42 IC, is controlled from the 8 and 16 clock lines to control selection of the banks of switches 1063, 1065 and 1067 through the OR-gates 1073, 1075 and 1077. It should be noted that the feedback resistor 188b and the resistor 176G have the same values so that the operational amplifier 1061 has a fixed gain of one, the switches 190 and 198 in detail in connection with the amplifier 60 are not required in the amplifier 70.

The output of the amplifier 70 is supplied through a potentiometer 1062 and resistor 1064 to one semiconductor analog switch on the 4051 IC 1066. Additional high frequency filter resistors 1068, 1070 and 1072 may be selected by different ones of the switches 1066, the common output of these switches on the conductor 1069 being supplied to the common input of the demultiplexing switches 1074, 1076 and 1078 which are employed selectively to connect the common signal path to the sampling capacitors 76 which are individual to each of the twenty channels of the EEG system. The switches 1066 are controlled from the master control panel 126 over the conductors 984 and 986 so that the operator may select a particular value of series resistor for the high frequency filtering which will take place in each channel. More specifically the selected series resistor, such as the resistor 1064, will function with each of the sampling capacitors 76 during successive channel periods to provide a high frequency filter which will attenuate undesired high frequencies and prevent them from entering the individual recording channels 78. The demultiplexing switches 1074, 1076 and 1078 are controlled from the decoder 1080, through the OR-gates 1091, 1093 and 1095. The OR-gates have as their second input the EA4 wave form the start of which is delayed relative to the wave forms EA, EA1, EA2 and EA3 so that switching in earlier stages is completed before the capacitors 76 are connected. Accordingly, during alternate frames the capacitors 76 are sequentially connected to the common series high frequency filter resistor, such as the resistor 1064.

Referring now to FIGS. 27 to 29, wherein the details of the clock control 146 are shown, a phase lock loop chip 1082, which may comprise a type 4046 IC, is employed to establish a sampling frequency of 86.4 KHz on the output conductor 1084. A choice of 86.4 KHz has been found to minimize interference from 60-cycle pickup on the power lines. The IC 1082 includes an oscillator whose frequency may be controlled by means of the potentiometer 1086 and the counters 1088, 1090, 1092 and 1094 are employed to provide an approximately 60-cycle component which is fed back over the conductor 1096 to the phase detector in the IC 1082 where it is compared with a signal from the 60-cycle power line. The counter 1088 divides by a factor of 16. The counter 1090 divides by a factor of five or six under the control of the switch 1087 and AND-gate 1089. The counter 1092 divides by a factor of nine and the counter 1094 by a factor of two.

Sixty-cycle power signals from the power transformer of the EEG system are coupled through input filters comprising the series resistors 1098 and the shunt capacitors 1100, through Schmidt inverters 1102 and differentiation networks comprising the series capacitor 1104 and shunt resistor 1106 to the two inputs of a NAND-gate 1108 the output of which is supplied to a divide by two flip-flop 1110 the Q output of which is supplied to the phase detector on the chip 1082.

The 86.4 KHz signal on the conductor 1084 is supplied through an inverter 1112 to the series connected JK flip-flops 1114 and 1116 which collectively divide the input signal by a factor of three, a third flip-flop 1118 functioning to divide the output by an additional factor of 2. The enabling signals for the system are derived from these flip-flops. In order that the clock scan signals will not be applied to a particular circuit before its enabling signal, a delay of approximately two microseconds is provided by the network 1120, 1122, the output of this network being supplied to a counter 1124 which develops the 1, 2, 4 and 8 clock signals. An additional flip-flop 1126 is employed to develop the 16 clock signal and the flip-flop 1128 develops a signal on the conductor 1130 which is employed to develop the EA signals. More particularly, the signal on the conductor 1130 is supplied to the AND-gates 1132, 1134, 1136, 1138 and 1140 which are employed to develop the signals EA, EA1, EA2, EA3 and EA4, respectively. The flip-flops 1114, 1116 and 1118, with two additional flip-flops 1142 and 1144, the OR-gates 1146, 1148, 1150, 1152 and the AND-gates 1154 and 1156 providing the other inputs to the AND-gates 1132, 1134, 1136, 1138 and 1140. An AND-gate 1158 is employed to develop the IN2 signal which is supplied to the EAROM 252 as a timing signal to allow the microprocessor 254 to control the EAROM 252 only in timed relation to the clock control 146.

The opposite polarity output from the flip-flop 1128 is supplied to the flip-flops 1160 and 1162, through the differentiation network 1164, 1166, the Q output of the flip-flop 1160 providing the 4-channel polarity reversing MOD signal on the conductor 120. The #1 clock line controls the flip-flop 1162 and is also supplied as one input to a NAND-gate 1160 which also receives the Q output of 1168. A NAND-gate 1170 receives the #1 output, through the inverter 1176 and also receives the Q output of 1160. The outputs of 1168 and 1170 are combined in the NAND-gate 1172 and supplied through the inverter 1174 to the switching conductor 1054, and through the inverter 1175 to the switching conductor 1056. These switching waveforms thus include components which vary at channel frequency (#1 line) and at a 4-channel rate signal from flip-flop 1128, and are employed to control the demodulation amplifier 66, as described generally heretofore.

In FIG. 30 the enabling wave forms EA, EB, EA1, EA2, EA3 and EA4 are shown in relation to the output wave form 1180 of the phase lock loop chip 1082. The IN2 wave form 1182 is also shwon in this figure. Also, a portion of the #1 scan line wave form 1184 is shown in this figure to illustrate the two-microsecond delay provided by the network 1120, 1122.

In FIG. 31 the clock scan line wave forms #1, #2, #4, #8 and #16 are shown, it being noted that twenty reversals of the #1 wave form 1184 comprise one 20-channel frame. In addition, the switching wave forms 1186 which are developed on the conductor 1054 and 1056 are shown in this figure. The EA and EA4 wave forms are also repeated in this figure to illustrate the disabling function of the EA and EB wave forms during alternate frames. Also, the wave form 1188 on the conductor 1130 is shown in this figure.

The series of thirteen fast clock pulses 1190 which occur at a 2 MHz rate and are supplied over the conductor 92 to the shift register in the control logic 88 at the start of each channel period, is also shown in relation to a portion of the EB wave form in FIG. 31. In this connection it is pointed out that the EB wave form repeats each frame and is not disabling for alternate frames, as are the EA, EA1, EA2, EA3 and EA4 wave forms. More particularly, the EB wave form is taken directly from the output of the flip-flop 1118 whereas the EA series of wave forms are controlled by the wave form 1188 on the conductor 1130. This means that the switches 84 and 86 in the head box 50 are controlled each channel period of each frame to connect selected electrode pairs to the output of the amplifier 58. However, the EA series of wave forms, such as the EA wave form which controls the switches 186 in the input of the second amplifier 60, prevent the switches 186 from closing during alternate frames so that no capacitor 184 is connected to the plus input of the amplifier 60 during alternate frames. When no capacitor 184 is connected to the plus input of the amplifier 60 both inputs of this amplifier follow the signal on the cable 174 from the previous amplifier 58 so that during alternate frames the output of the amplifier 60 is essentially zero. Similar operation is provided in the amplifiers 60 and 70. It will be recalled that elimination of alternate frames is required because of the 4-channel component of the MOD signal which reverses the polarity of each channel during alternate frames. If the capacitors 184, 184a and 184b were connected into the circuit each frame the polarity of the d.c. component of each electrode pair signal would reverse each frame so that each capacitor could not be charged to a level proportional to the d.c. component and base line suppression would not be achieved.

While there have been illustrated and described various embodiments of the present invention, it will be apparent that various changes and modifications thereof will occur to those skilled in the art. It is intended in the appended claims to cover all such changes and modifications as fall within the true spirit and scope of the present invention.

What is claimed as new and desired to be secured by Letters Patent of the United States is:

1. In an EEG system, a plurality of patient electrodes, a portable head box adapted to be placed near the patient to be tested, a multi-channel recording apparatus located remotely from said head box, a multi-conductor transmission link connecting said head box and said recording apparatus; said head box having (i) a plurality of input terminals individually corresponding to said plurality of patient electrodes, (ii) an output terminal coupled to said link and having (iii) a ground point that is electrically isolated from said link and from said recording apparatus; control means in said head box for selectively connecting predetermined ones of said input terminals to said output terminal during each of successive time periods which recur in repetitive time position frames and thereby applying a multiplexed signal to said link, means in said recording apparatus for demultiplexing said multiplexed signal, and a plurality of low-pass input filters individually connected between said patient electrodes, said input terminals and said ground point.

2. The EEG system of claim 1, wherein each of said input filters passes the highest frequency brain wave signals of a patient connected to said electrodes but attenuates still higher frequencies so as to prevent undesired cross modulation components from being developed at said output terminal.

3. The EEG system of claim 1, wherein each of said input filters comprises a single series resistor and a single shunt capacitor.

4. The EEG system of claim 1, which includes a patient ground electrode, and means connecting said patient ground electrode to said isolated ground.

5. The EEG system of claim 4, which includes means for limiting the current which can flow between any of said plurality of electrodes and said patient ground electrode to a predetermined maximum value.

6. The EEG system of claim 5, wherein said current limiting means includes a single current limiting device connected between said patient ground electrode and said isolated ground.

7. In an EEG system, a plurality of patient electrodes, a portable head box adapted to be placed near the patient to be tested, a multi-channel recording apparatus located remotely from said head box, a multi-conductor transmission link connecting said head box and said recording apparatus, said head box having a plurality of input terminals individually corresponding to said plurality of patient electrodes and an output terminal coupled to predetermined conductors of said link, switch means in said head box for connecting selected ones of said input terminals to said output terminal during respective time periods which recur in repetitive time position frames, means in said recording apparatus for developing during each time position frame a sequence of multi-bit digital signals corresponding to said selected ones of said plurality of input terminals, a control terminal in said head box, said multi-bit digital signals being applied to said control terminal, in serial bit form, through said link, means in said head box connected to said control terminal for receiving said multi-bit digital signals for storage and use during respective time periods, means in said head box controlled by said stored digital signals for selectively actuating said switch means and thereby applying a multiplexed signal to said link, and means in the recording apparatus for demultiplexing said multiplexed signal.

8. The EEG system of claim 7, which includes means defining a ground which is electrically isolated from said recording apparatus, means connecting said receiving means to said isolated ground, and means electrically isolating said control terminal from said isolated ground.

9. The EEG system of claim 8, wherein said isolating means comprises an electro-optical isolator.

10. In an EEG system, a plurality of patient electrodes, a portable head box adapted to be placed near the patient to be tested, a multi-channel recording apparatus located remotely from said head box, a multi-conductor transmission link connecting said head box and said recording apparatus, said head box having a plurality of input terminals individually corresponding to said plurality of patient electrodes, a differential amplifier in said head box having at least two input terminals and an output terminal, means in said head box for selectively connecting one of said input terminals to one input of said differential amplifier and simultaneously connecting another of said input terminals to the other input of said differential amplifier during successive time periods which recur in repetitive time position frames, means defining a system ground, means defining an isolated ground in said head box which is electrically isolated from said system ground, coupling means for coupling said amplifier to said transmission link, said coupling means having an input section connected to said isolated ground and an output section connected to said system ground, means for connecting the output terminal of said differential amplifier to the input section of said coupling means, means for connecting the output section of said coupling means to said transmission link to supply a multiplexed signal to said recording apparatus over said link, and means in said recording apparatus for demultiplexing said multiplexed signal.

11. The EEG system of claim 10, wherein said coupling means includes a transformer having a first winding serving a the input section thereof and a second winding serving as the output section thereof.

12. The EEG system of claim 11, wherein said transformer includes a third winding, and means including said third winding for supplying a negative feedback signal to said differential amplifier to provide a high impedance at the inputs of said differential amplifier while isolating said second winding from said isolated ground.

13. The EEG system of claim 12, wherein said first and third windings are bifilar wound so that said differential amplifier has a relatively wide band width.

14. The EEG system of claim 13, wherein said second winding has relatively little capacitance with respect to said first and third windings, thereby to minimize the capacitance to said isolated ground.

15. The EEG system of claim 11, wherein said amplifier output terminal connecting means includes polarity reversing switching means for periodically reversing the polarity of the connection between said amplifier output terminal and said first winding and thereby preventing d.c. saturation of said transformer.

16. In an EEG system, a plurality of patient electrodes and a patient ground electrode, a portable head box adapted to be placed near the patient to be tested, a multi-channel recording apparatus located remotely from said head box, a multi-conductor transmission link connecting said head box and said recording apparatus, said head box having a plurality of input terminals individually corresponding to said electrodes, an output circuit, and a ground point that is electrically isolated from said recording apparatus, switching means in said head box for selectively connecting selected ones of said input terminals to said output circuit during successive time periods which recur in repetitive time position frames to supply a multiplexed signal to the recording apparatus through said link, means in said recording apparatus for demultiplexing said multiplexed signal, and means for limiting the current which can flow between said patient ground electrode and said ground point to a predetermined maximum value.

17. In an EEG system, a plurality of patient electrodes, an input circuit, means for sequentially connecting selected pairs of said electrodes to said input circuit during different time positions in repetitive time position frames, a differential amplifier for amplifying the electrode pair signal voltages sequentially connected to said input circuit and having first and second inputs, means connecting said signal voltages to said first differential amplifier input, a time constant resistor connected to said second input, a plurality of time constant capacitors one for each of said time periods, means for connecting different ones of said capacitors to said second input during said different time periods, means for supplying said signal voltages to said time constant resistor so that an offset potential is developed on each of said capacitors which substantially suppresses the d.c. component of each of said signal voltages, said means for connecting different ones of said capacitors to said second input comprising a plurality of semiconductor analog switches each having a control line and input and output lines which are electrically connected together when a control pulse of predetermined polarity is applied to said control line, each of said switches having stray capacitance between said control line and said input and output lines, means for sequentially applying control pulses to the control lines of said switches during said different time periods so that said capacitors are sequentially connected to said second input, and means for compensating for an undesired offset voltage developed on said capacitor due to coupling of said control pulses to said capacitor through said stray capacitance.

18. The EEG system of claim 17, wherein said compensating means comprises a charge injection capacitor common to said time constant capacitors, and switch means controlled by said control pulses for supplying a voltage of the opposite polarity from said offset voltage through said charge injection capacitor to the corresponding one of said time constant capacitors.

19. The EEG system of claim 18, which includes a series of adjustable voltage sources one for each of said time constant capacitors and sequentially connected thereto through said switch means.

20. In an EEG system, a plurality of patient electrodes, a differential amplifier having first and second inputs, means for selectively connecting a selected one of said electrodes to said first input and simultaneously connecting a selected one of said electrodes to said second input during each of successive time periods which recur in repetitive time position frames, recording means having a plurality of input channels, a capacitor connected to each of said input channels, and means for selectively connecting the output of said differential amplifier to each of said capacitors in sequence during said time periods, said selective connecting means including a resistor common to said capacitors and forming a low-pass filter with each of said capacitors during said time periods.

21. The EEG system of claim 20, which includes means for varying the value of said common resistor, thereby to vary the frequency characteristics of all of said low-pass filters.

22. In an EEG system, a plurality of patient electrodes, a differential amplifier having first and second inputs, means for selectively connecting a selected one of said electrodes to said first input and simultaneously connecting a selected one of said electrodes to said second input during each of successive time periods which recur in repetitive time position frames, recording means having a plurality of input channels, a capacitor connected to each of said input channels, and means including voltage limiter means for selectively connecting the output of said amplifier to each of said capacitors in sequence during said time periods, said selective connecting means including a resistor common to said capacitors and forming a low-pass filter with each of said capacitors during said time periods.

23. In an EEG system, a plurality of patient electrodes, a differential amplifier having first and second inputs, first switch means for connecting any one of said electrodes to said first input, second switch means for connecting any one of said electrodes to said second input, means for selectively controlling said first and second switch means to connect pairs of said electrodes to said first and second inputs during different time periods which recur in repetitive time position frames, an isolating transformer, and means for connecting the output of said differential amplifier to said isolating transformer, said connecting means including means for reversing the polarity of the output of said amplifier at a predetermined rate.

24. The EEG system of claim 23, which includes second amplifier means connected to the output of said isolating transformer, and means for reversing the polarity of the output of said second amplifier means at said predetermined rate.

25. In an EEG system, a plurality of patient electrodes, a differential amplifier having first and second inputs, first switch means for connecting any one of said electrodes to said first input, second switch means for connecting any one of said electrodes to said second input, means for selectively controlling said first and second switch means to connect pairs of said electrodes to said first and second inputs during different time periods which recur in repetitive time position frames, a transformer, polarity reversing switch means connected between the output of said differential amplifier and said transformer, means for generating a control signal which has the same polarity for a group of adjacent ones of said time periods in one time position frame but reverses in polarity for said group of time periods in a succeeding time position frame, and means for controlling said polarity reversing switch means in accordance with said control signal.

26. The EEG system of claim 25, which includes second amplifier means connected to the output of said transformer, and means for reversing the polarity of the output of said second amplifier means in accordance with said control signal.

27. In an EEG system, a plurality of patient electrodes, a differential amplifier having first and second inputs, means for sequentially supplying a series of electrode pair signal voltages to both said first and second inputs during different time periods which recur in repetitive time position frames, said signal voltages incuding a d.c. component and an a.c. brain wave component, a plurality of capacitors, means for connecting different ones of said capacitors to one of said first and second inputs during said time periods in a given time position frame, means operative when none of said capacitors is connected to said one input for causing the output of said amplifier to be substantially zero, and means for varying the closed loop gain of said differential amplifier while maintaining the loop gain thereof substantially constant.

28. The EEG system of claim 27, which includes means for concurrently adjusting the open loop gain of said amplifier to different values during different ones of said time periods.

29. The EEG system of claim 28, wherein said closed loop gain and said open loop gain are adjusted to maintain the loop gain of said amplifier substantially constant.

30. In an EEG system, a plurality of patient electrodes, a portable head box adapted to be placed near the patient to be tested, a multi-channel recording apparatus located remotely from said head box, a multi-conductor transmission link connecting said head box and said recording apparatus, said head box having a plurality of input terminals corresponding to said patient electrodes and having first amplifier means, means for sequentially connecting selected ones of said input terminals to said first amplifier means during sequential time periods which recur in respective time position frames whereby said amplifier means establishes a multiplexed analog signal including a.c. and d.c. components, a transformer for coupling said multiplexed signal to said transmission link, polarity reversing switching means for connecting said first amplifier means to said transformer, said switching means periodically reversing the polarity of the connection between said first amplifier means and said transformer to prevent d.c. saturation of said transformer, second amplifier means in said recording apparatus for receiving said multiplexed signal and for amplifying the a.c. components thereof while suppressing the d.c. components thereof, and means in said recording apparatus for demultiplexing the signal produced by the second amplifier means.

* * * * *